United States Patent
Ettinger et al.

(10) Patent No.: US 10,022,443 B2
(45) Date of Patent: Jul. 17, 2018

(54) ANTIBODIES SPECIFIC FOR IL-21 AND USES THEREOF

(71) Applicant: Boston Pharmaceuticals Inc., Cambridge, MA (US)

(72) Inventors: Catherine Ettinger, Gaithersburg, MD (US); Jodi Karnell, Gaithersburg, MD (US); Melissa Damschroder, Gaithersburg, MD (US); Partha Chowdhury, Gaithersburg, MD (US); Xiaodong Xiao, Gaithersburg, MD (US); Ping Tsui, Gaithersburg, MD (US); Reena Varkey, Gaithersburg, MD (US); Stacey Drabic, Gaithersburg, MD (US); Laura Carter, Ann Arbor, MI (US); Ronald Herbst, Gaithersburg, MD (US); Qun Du, Gaithersburg, MD (US); Brian Michael Naiman, Gaithersburg, MD (US)

(73) Assignee: Boston Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 15/305,093

(22) PCT Filed: Apr. 7, 2015

(86) PCT No.: PCT/US2015/024650
§ 371 (c)(1),
(2) Date: Oct. 18, 2016

(87) PCT Pub. No.: WO2015/157238
PCT Pub. Date: Oct. 15, 2015

(65) Prior Publication Data
US 2017/0173149 A1 Jun. 22, 2017

Related U.S. Application Data

(60) Provisional application No. 61/976,684, filed on Apr. 8, 2014.

(51) Int. Cl.
*A61K 39/395* (2006.01)
*C07K 16/24* (2006.01)
*G01N 33/53* (2006.01)
*A61K 39/00* (2006.01)

(52) U.S. Cl.
CPC ........ *A61K 39/3955* (2013.01); *C07K 16/244* (2013.01); *G01N 33/53* (2013.01); *A61K 2039/505* (2013.01); *A61K 2121/00* (2013.01)

(58) Field of Classification Search
None
See application file for complete search history.

(56) References Cited

U.S. PATENT DOCUMENTS

2009/0191214 A1    7/2009   Jaspers et al.

FOREIGN PATENT DOCUMENTS

| WO | WO 00/29447 A1 | 5/2000 |
|----|----|----|
| WO | WO 01/71005 A2 | 9/2001 |
| WO | WO 2009/111507 A1 | 9/2009 |
| WO | WO 2010/001585 A1 | 1/2010 |
| WO | WO 2011/047146 A2 | 4/2011 |
| WO | WO 2012/068540 A2 | 5/2012 |
| WO | WO 2015/142637 A1 | 9/2015 |

OTHER PUBLICATIONS

Jin et al., "Characterization of a murine-human chimeric antibody with specificity for the pre-S2 surface antigen of hepatitis B virus expresses in baculovirus-infected insect cells," Virus Research, 1995, 38:269-277.
Pollock et al., "Identification of mutant monoclonal antibodies with increased antigen binding," Proc. Natl. Acad. Sci, USA, Apr. 1988, 85:2298-2302.
Maurer et al., "Generation and characterization of human anti-human IL-21 neutralizing monoclonal antibodies," MAbs, Jan.-Feb. 2012, 4(1):69-83.

*Primary Examiner* — Dong Jiang
(74) *Attorney, Agent, or Firm* — Foley & Lardner LLP

(57) ABSTRACT

This disclosure provides IL-21 binding molecules, e.g., anti-IL-21 antibodies and antigen-binding fragments thereof. In certain aspects the anti-IL-21 antibodies and fragments thereof can be hybridoma-derived murine monoclonal antibodies, and humanized versions thereof. In certain aspects the binding molecules, e.g., anti-IL-21 antibodies and antigen-binding fragments thereof provided herein inhibit, suppress, or antagonize IL-21 activity. In addition, this disclosure provides compositions and methods for diagnosing and treating diseases or disorders, e.g., inflammatory, immune-mediated, or autoimmune diseases or disorders associated with IL-21-mediated signal transduction. In a particular embodiment, the disclosure provides methods for treating or preventing Graft-versus-host disease (GVHD) using IL-21 binding molecules, e.g., anti-IL-21 antibodies and antigen-binding fragments thereof.

17 Claims, 24 Drawing Sheets

FIG. 1A

VH Alignment:

```
             |---------FW1----------|--CDR1--|----FW2----|--------CDR2---------|
9F11      EVELVESGGGLVQPGGSMKLSCAASGFTFSDAWMDWVRQSPEKGLEWVAEIRSEADNHPTYYAESVKG
9F11-4    EVQLVESGGGLVQPGGSLRLSCAASGFTFSDAWMDWVRQAPGKGLEWVAEIRSEADNHPTYYAESVKG
9F11-6    EVQLVESGGGLVQPGGSLRLSCAASGFTFSDAWMDWVRQAPGKGLEWVAEIRSEADNHPTYYAESVKG
9F11-11   EVQLVESGGGLVQPGGSLRLSCAASGFTFSDAWMDWVRQAPGKGLEWVAEIRSEADNHPTYYAESVKG
```

VL Alignment:

```
             |---------FW1----------|---CDR1---|-----FW2-----|------CDR2------|
9F11      DIVLTQSPASLAVSLGQRATISCRASKSVSTYGYSYMHWYQQKPGQPPKLLIYLASNLESGVPARFSG
9F11-4    DIVMTQTPLSLSVTPGQPASISCRASKSVSTYGYSYMHWYLQKPGQPPQLLIYLASNLESGVPDRFSG
9F11-6    DIVMTQTPLSLSVTPGQPASISCRASKSVSTYGYSYMHWYLQKPGQPPQLLIYLASNLESGVPDRFSG
9F11-11   DIVLTQTPLSLSVTPGQPASISCRASKSVSTYGYSYMHWYLQKPGQPPQLLIYLASNLESGVPDRFSG
```

FIG. 1A Contd.

```
            ------FW3------  ---CDR3---  --FW4--
RFTISRDDSKSSVYLQMNSLRAEDSGIYYCTEYDYEGFVHWGQGTLVTVSA
RFTISRDDSKNSLYLQMNSLKTEDTAVYYCTEYDYEGFVHWGQGTLVTVSS
RFTISRDDSKNSVYLQMNSLKTEDTAVYYCTEYDYEGFVHWGQGTLVTVSS
RFTISRDDSKNSLYLQMNSLKTEDTAVYYCTEYDYEGFVHWGQGTLVTVSS

------FW3------  ---CDR3---  --FW4--
SGSGTDFTLNIHPVEEEDAATYYCQHSRELPLTFGAGTKLELK
SGSGTDFTLKISRVEAEDVGVYYCQHSRELPLTFGQGTKLEIK
SGSGTDFTLKISRVEAEDVGVYYCQHSRELPLTFGQGTKLEIK
SGSGTDFTLKISRVEAEDVGVYYCQHSRELPLTFGQGTKLEIK
```

FIG. 1B

VL Alignment:

```
                    -----FW1---------- ------CDR1------- ----FW2---- --------CDR2---------
19E3VL-murine   DIQLTQTTSSLSASLGDRVTISCRASQDISNFLNWYQQTPDGTVKLLIYYTSRLHSGVPSRFSGSG
19E3VL-K1       DIQLTQSPSSLSASVGDRVTITCRASQDISNFLNWYQQKPGKAPKLLIYYTSRLHSGVPSRFSGSG
19E3VL-K2       DIQLTQSPSSLSASVGDRVTITCRASQDISNFLNWYQQKPGKAVKLLIYYTSRLHSGVPSRFSGSG
```

VH Alignment:

```
                    -----FW1---------- ---CDR1--- ----FW2---- ------------CDR2-------------
19E3VH-murine   QVQLQQPGSELVMPGASVKMSCKASGYIFTDYWMHWVKQRPGQGLEWIGTIDPSDNYTIYSQNFKG
19E3VH-Ha       QVQLVQSGAEVKKPGASVKVSCKASGYTFTDYWMHWVRQAPGQGLEWMGTIDPSDNYTIYSQNFKG
19E3VH-Hb       QVQLQQPGSELVMPGASVKMSCKASGYIFTDYWMHWVRQAPGQGLEWMGTIDPSDNYTIYSQNFKG
19E3VH-Hc       QVQLVQSGAEVKKPGASVKVSCKASGYTFTDYWMHWVRQAPGQGLEWMGTIDPSDNYTIYSQNFKG
```

FIG. 1B Contd.

```
------FW3------  ---CDR3--- ---FW4---
SGTDYSLTITSNLEQEDIATYFCQQGHTLPRTFGGGTKLEIK
SGTDYTLTITSSLQPEDFATYYCQQGHTLPRTFGGGTKVEIK
SGTDYTLTITSSLQPEDFATYFCQQGHTLPRTFGGGTKVEIK

------FW3------  ---CDR3--- ---FW4---
KATLTVDESSSTAYMLLSSLTSEDSAVYFCARYGFAMDYWGQGTSVTVSS
RVTMTRDTSTSTVYMELSSLRSEDTAVYYCARYGFAMDYWGQGTLVTVSS
RVTMTRDTSTSTVYMELSSLRSEDTAVYYCARYGFAMDYWGQGTLVTVSS
KATLTVDESSSTAYMLLSSLTSEDSAVYFCARYGFAMDYWGQGTLVTVSS
```

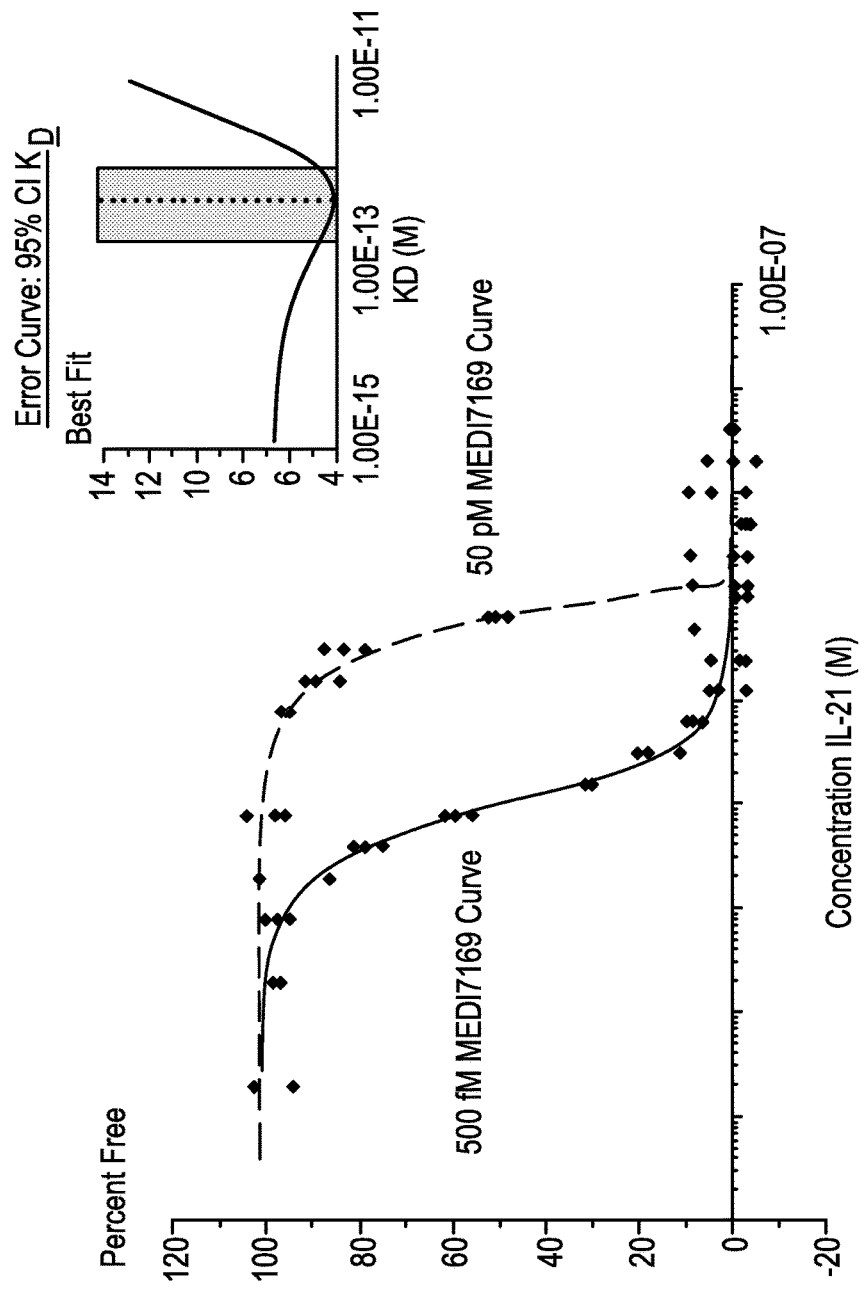

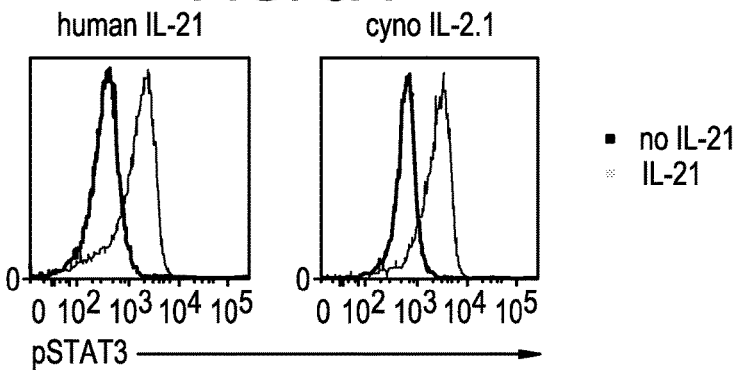
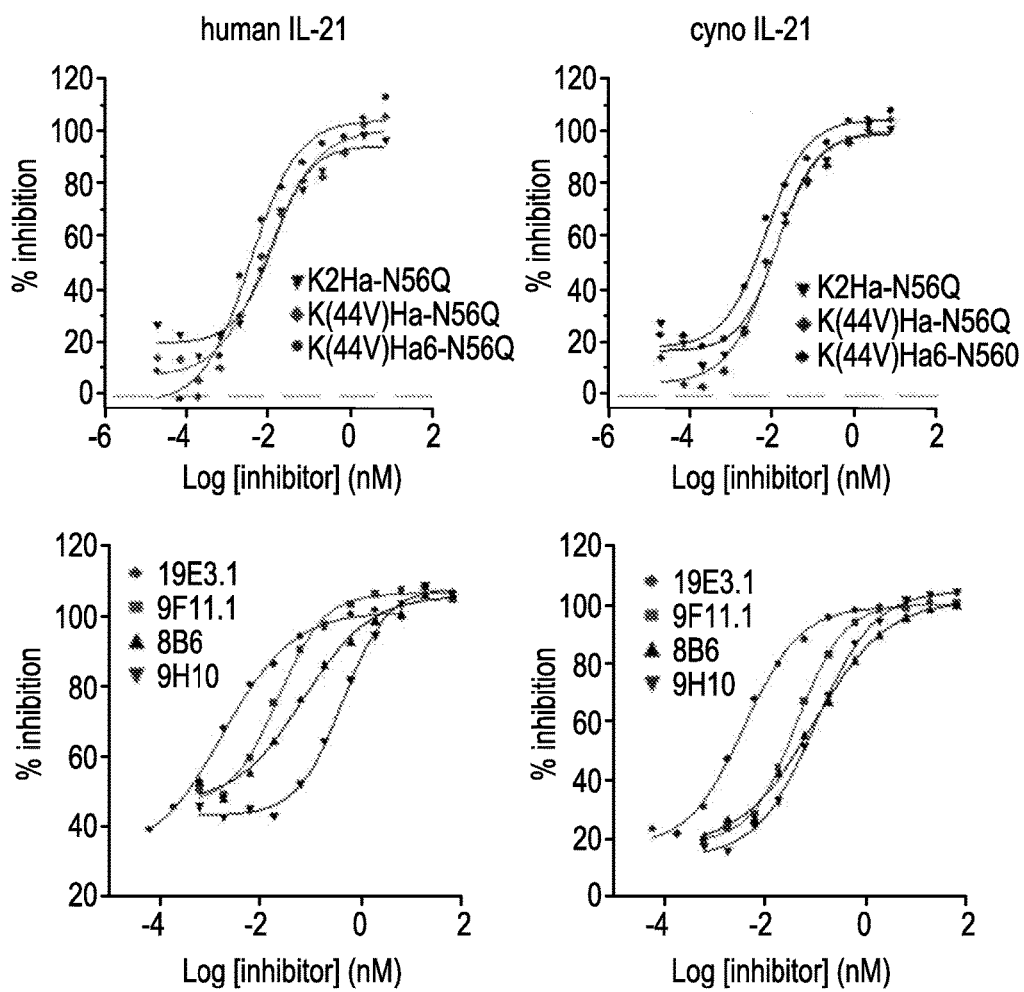

human IL-21 cyno IL-21

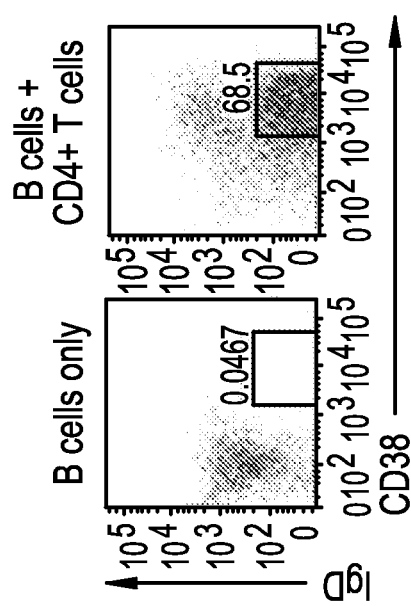

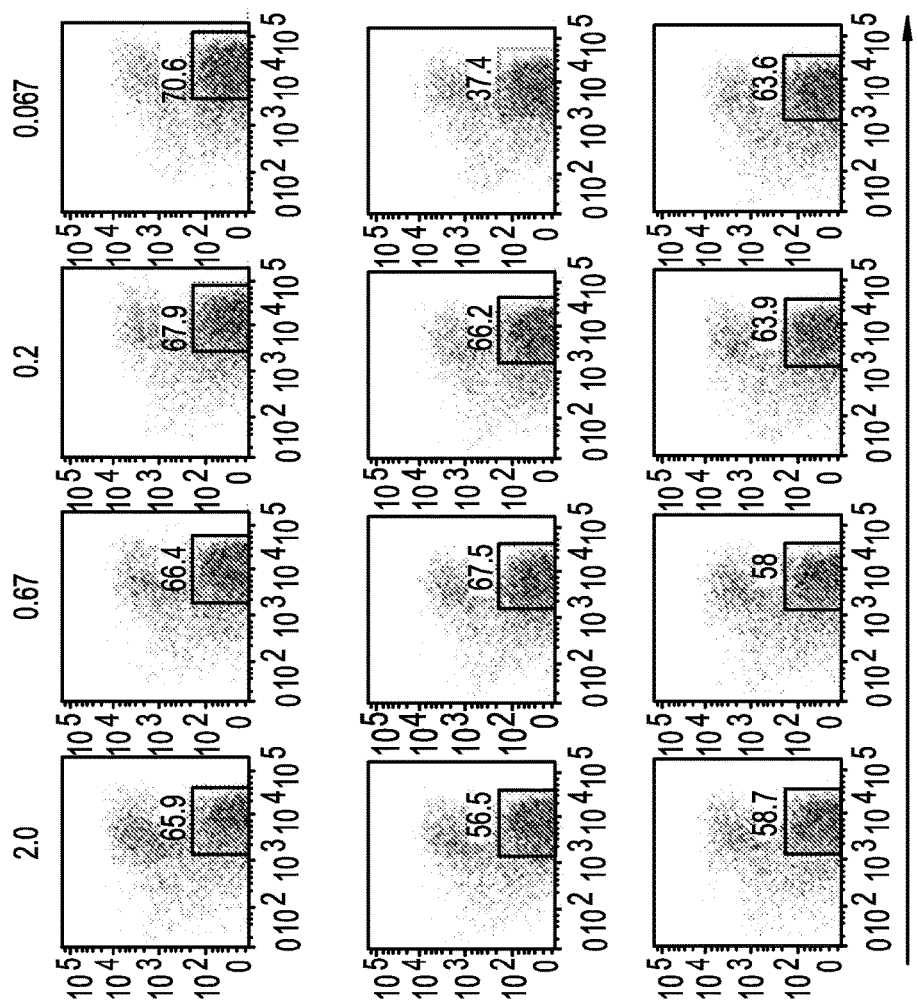

FIG. 6C
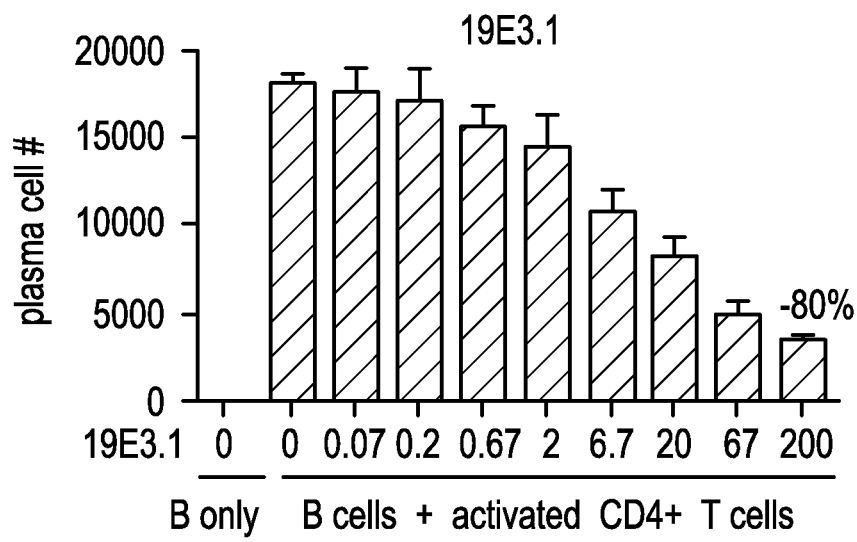
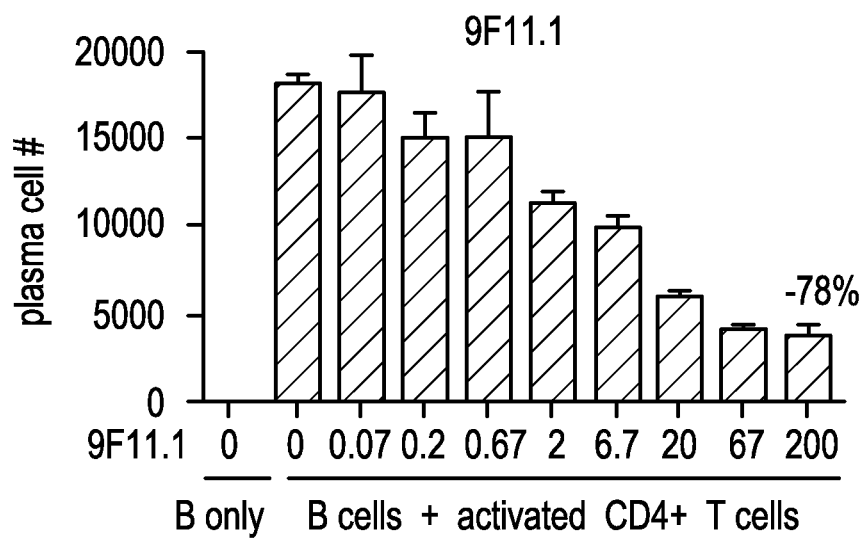

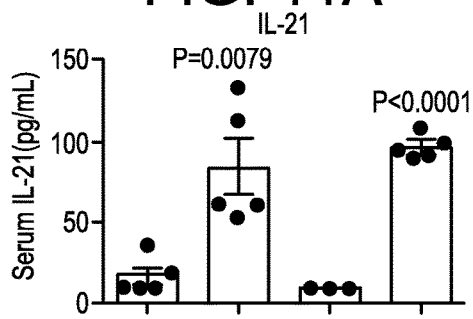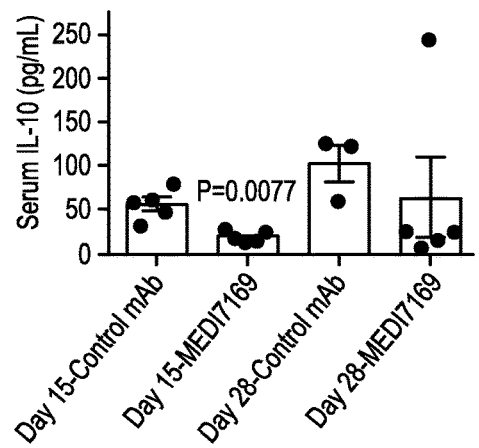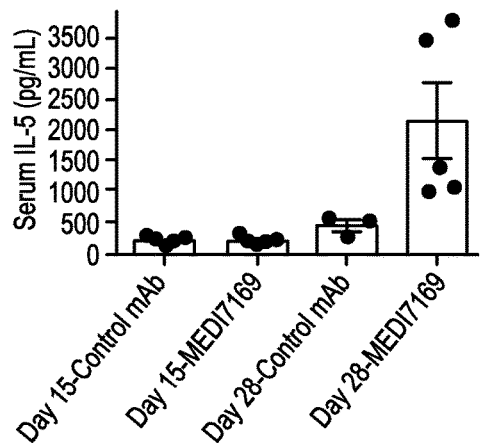

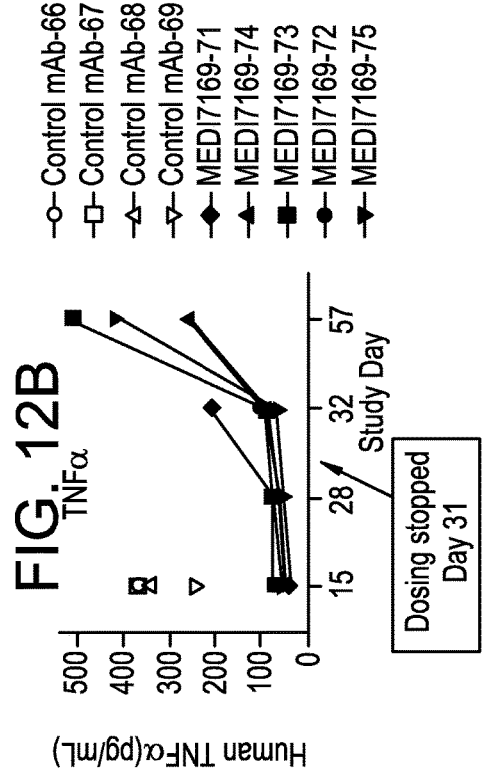
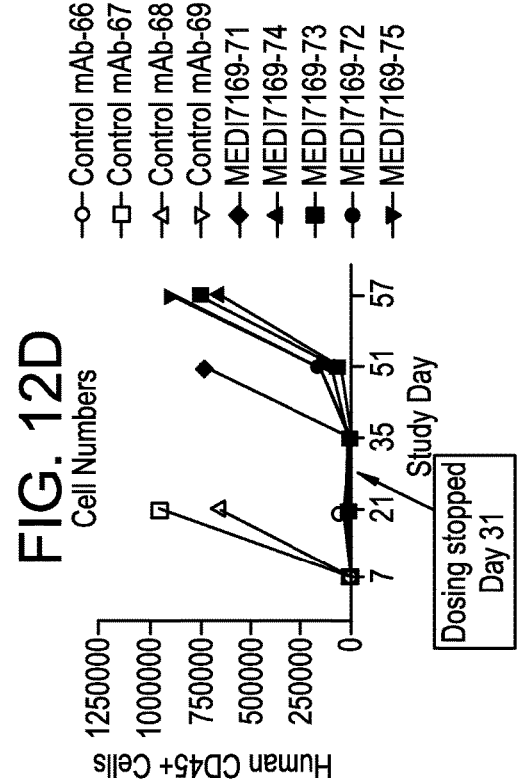
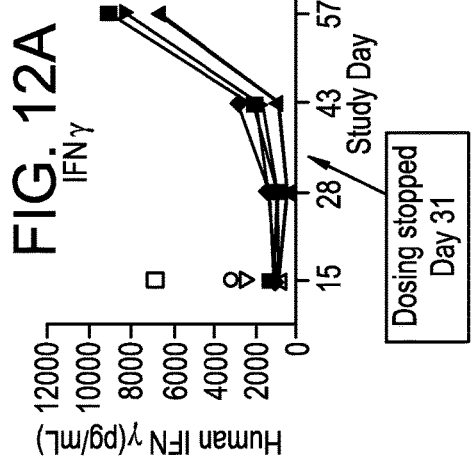
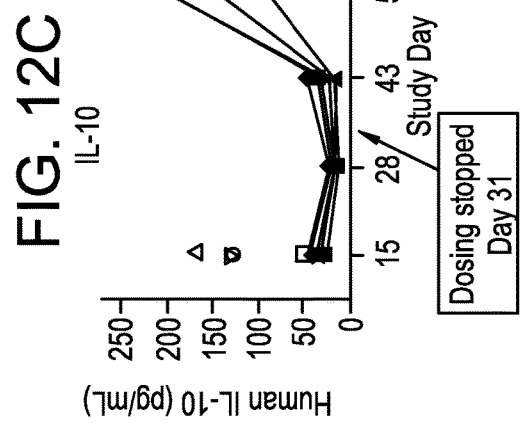

SEQUENCE LISTING

```
<160> NUMBER OF SEQ ID NOS: 67

<210> SEQ ID NO 1
<211> LENGTH: 564
<212> TYPE: DNA
<213> ORGANISM: Homo sapiens

<400> SEQUENCE: 1
ctgaagtgaa aacgagacca aggtccagct ctactgttgg tacttatgag atccagtcct      60
ggcaacatgg agaggattgt catctgtctg atggtcatct tcttggggac actggtccac     120
aaatcaagct cccaaggtca agatcgccac atgattagaa tgcgtcaact tatagatatt     180
gttgatcagc tgaaaaatta tgtgaatgac ttggtccctg aatttctgcc agctccagaa     240
gatgtagaga caaactgtga gtggtcagct ttttcctgtt ttcagaaggc ccaactaaag     300
tcagcaaata caggaaacaa tgaaggata atcaatgtat caattaaaaa gctgaagagg     360
aaaccacctt ccacaaatgc agggagaaga cagaaacaca gactaacatg cccttcatgt     420
gattcttatg agaaaaaacc acccaaagaa ttcctagaaa gattcaaatc acttctccaa     480
aagatgattc atcagcatct gtcctctaga acacacggaa gtgaagattc ctgaggatct     540
```
aacttgcagt tggacattgt taca                                             564

<210> SEQ ID NO 2
<211> LENGTH: 161
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Glu
        115                 120                 125

Lys Lys Pro Pro Lys Glu Phe Leu Glu Arg Phe Lys Ser Leu Leu Gln
    130                 135                 140

Lys Met Ile His Gln His Leu Ser Ser Arg Thr His Gly Ser Glu Asp
145                 150                 155                 160

Ser

<210> SEQ ID NO 3
<211> LENGTH: 489
<212> TYPE: DNA
<213> ORGANISM: Macaca fascicularis

<400> SEQUENCE: 3
atgagatcca gtcctggcaa catggagagg atagtcatct gtctgatggt catcttcttg       60
gggacactgg tccacaaatc aagctcccaa ggtcaagatc gccacatgat tagaatgcgt      120
caacttatag atattgttga tcagctgaaa aattatgtga atgacttgga ccctgaattt      180
ctgccagctc cagaagatgt agagacaaac tgtgagtggt cagctatttc ctgttttcag      240
aaggcccaac taaagtcagc aaatacagga acaatgaaa ggataatcaa tttatcaatt       300
aaaaagctga gaggaaatc accttccaca ggtgcagaga gaagcagaa acacagacta        360 acatgcccttt catgtgattc ttatgagaaa aaaccaccca agaattcct agaaagattc      420 aaatcacttc tccaaaagat gattcatcag catctgtcct ctagaacaca tggaagtgaa      480
gattcctga                                                             489

<210> SEQ ID NO 4
<211> LENGTH: 162
<212> TYPE: PRT
<213> ORGANISM: Macaca fascicularis

<400> SEQUENCE: 4

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Asp Pro Glu Phe Leu Pro Ala Pro
    50                  55                  60

Glu Asp Val Glu Thr Asn Cys Glu Trp Ser Ala Ile Ser Cys Phe Gln
65                  70                  75                  80

Lys Ala Gln Leu Lys Ser Ala Asn Thr Gly Asn Asn Glu Arg Ile Ile
                85                  90                  95

Asn Leu Ser Ile Lys Lys Leu Lys Arg Lys Ser Pro Ser Thr Gly Ala
            100                 105                 110

Glu Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 5
<211> LENGTH: 357
<212> TYPE: DNA
<213> ORGANISM: Mus sp.

<400> SEQUENCE: 5
gaagtggagc ttgtggagtc tggaggaggc ttggtgcaac ctggaggatc catgaaactc      60
tcttgtgctg cctctggatt cactttagt gacgcctgga tggactgggt ccgccagtct     120
ccagagaagg ggcttgagtg ggttgctgaa attagaagcg aagctgataa tcatccaaca     180
tactatgctg agtctgtgaa agggaggttc accatctcaa gagatgattc caaaagtagt     240
gtctacctgc aaatgaacag cttaagagct gaagacagtg gcatttatta ctgtactgaa     300
tatgattacg agggggtttgt acactggggc caggggacgc tggtcactgt ctctgca      357

<210> SEQ ID NO 6
<211> LENGTH: 116
<212> TYPE: PRT
<213> ORGANISM: Mus sp.

<400> SEQUENCE: 6

Gln Val Gln Leu Gln Gln Pro Gly Ser Glu Leu Val Met Pro Gly Ala
1               5                   10                  15

Ser Val Lys Met Ser Cys Lys Ala Ser Gly Tyr Ile Phe Thr Asp Tyr
            20                  25                  30

Trp Met His Trp Val Lys Gln Arg Pro Gly Gln Gly Leu Glu Trp Ile
        35                  40                  45

Gly Thr Ile Asp Pro Ser Asp Asn Tyr Thr Ile Tyr Ser Gln Asn Phe
    50                  55                  60

Lys Gly Lys Ala Thr Leu Thr Val Asp Glu Ser Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Tyr Gly Phe Ala Met Asp Tyr Trp Gly Gln Gly Thr Ser Val
            100                 105                 110

Thr Val Ser Ser

<210> SEQ ID NO 7
<211> LENGTH: 5
<212> TYPE: PRT
<213> ORGANISM: Mus sp.

<400> SEQUENCE: 7

Asp Tyr Trp Met His
1               5

<210> SEQ ID NO 8
<211> LENGTH: 17
<212> TYPE: PRT
<213> ORGANISM: Mus sp.

<400> SEQUENCE: 8

Thr Ile Asp Pro Ser Asp Asn Tyr Thr Ile Tyr Ser Gln Asn Phe Lys
1               5                   10                  15

Gly

<210> SEQ ID NO 9
<211> LENGTH: 7
<212> TYPE: PRT
<213> ORGANISM: Mus sp.

<400> SEQUENCE: 9

Tyr Gly Phe Ala Met Asp Tyr
1               5

<210> SEQ ID NO 10
<211> LENGTH: 321
<212> TYPE: DNA
<213> ORGANISM: Mus sp.

<400> SEQUENCE: 10
gatatccagc tgacacagac tacatcctcc ctgtctgcct ctctgggaga cagagtcacc    60
atcagttgca gggcaagtca ggacattagc aattttttaa actggtatca gcagacacca   120
gatggaactg ttaaactcct gatctactac acatcaagat tacactcagg agtcccatca   180
aggttcagtg cagtgggtc tggaacagat tattctctca ccattagcaa cctggagcaa    240
gaagatattg ccacttactt ttgccaacag ggtcatacgc ttcctcggac gttcggtgga   300
ggcaccaagc tggaaatcaa a                                             321

<210> SEQ ID NO 11
<211> LENGTH: 107
<212> TYPE: PRT
<213> ORGANISM: Mus sp.

<400> SEQUENCE: 11

Asp Ile Gln Leu Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
                20                  25                  30

Leu Asn Trp Tyr Gln Gln Thr Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

```
Glu Asp Ile Ala Thr Tyr Phe Cys Gln Gln Gly His Thr Leu Pro Arg
                85                  90                  95

Thr Phe Gly Gly Gly Thr Lys Leu Glu Ile Lys
            100                 105

<210> SEQ ID NO 12
<211> LENGTH: 11
<212> TYPE: PRT
<213> ORGANISM: Mus sp.

<400> SEQUENCE: 12

Arg Ala Ser Gln Asp Ile Ser Asn Phe Leu Asn
1               5                   10

<210> SEQ ID NO 13
<211> LENGTH: 7
<212> TYPE: PRT
<213> ORGANISM: Mus sp.

<400> SEQUENCE: 13

Tyr Thr Ser Arg Leu His Ser
1               5

<210> SEQ ID NO 14
<211> LENGTH: 9
<212> TYPE: PRT
<213> ORGANISM: Mus sp.

<400> SEQUENCE: 14

Gln Gln Gly His Thr Leu Pro Arg Thr
1               5

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: K2Ha-N56Q
      synthetic humanized VH region sequence

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met His Trp Val Arg Gln Ala Pro Gly Gln Gly Leu Glu Trp Met
            35                  40                  45

Gly Thr Ile Asp Pro Ser Asp Gln Tyr Thr Ile Tyr Ser Gln Asn Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Phe Ala Met Asp Tyr Trp Gly Gln Gly Thr Leu Val
                100                 105                 110

Thr Val Ser Ser
            115

<210> SEQ ID NO 16
<211> LENGTH: 446
<212> TYPE: PRT
```

<213> ORGANISM: Artificial Sequence
<220> FEATURE:
<223> OTHER INFORMATION: Description of Artificial Sequence: K2Ha-N56Q
    synthetic humanized VH + human CH region sequence

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Thr Ile Asp Pro Ser Asp Gln Tyr Thr Ile Tyr Ser Gln Asn Phe
50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Tyr Gly Phe Ala Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Tyr Ile Thr Arg Glu Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445
```

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: K2Ha-N56Q
      synthetic humanized VH region sequence

<400> SEQUENCE: 17

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Arg
                85                  90                  95

Thr Phe Gly Gly Gly Thr Lys Val Glu Ile Lys
            100                 105
```

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: K2Ha-N56Q
      synthetic humanized VL + human CL region sequence

<400> SEQUENCE: 18

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: K44VHa-N56Q
      synthetic humanized VH region sequence

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Thr Ile Asp Pro Ser Asp Gln Tyr Thr Ile Tyr Ser Gln Asn Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Phe Ala Met Asp Tyr Trp Gly Gln Gly Thr Leu Val
            100                 105                 110

Thr Val Ser Ser
        115
```

<210> SEQ ID NO 20
<211> LENGTH: 446
<212> TYPE: PRT
<213> ORGANISM: Artificial Sequence
<220> FEATURE:
<223> OTHER INFORMATION: Description of Artificial Sequence: K44VHa-N56Q
      synthetic humanized VH + human CH region sequence

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Met His Trp Val Arg Gln Ala Pro Gly Gln Gly Leu Glu Trp Met
        35                  40                  45

Gly Thr Ile Asp Pro Ser Asp Gln Tyr Thr Ile Tyr Ser Gln Asn Phe
    50                  55                  60

Lys Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                    85                  90                  95

Ala Arg Tyr Gly Phe Ala Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: K44VHa-N56Q
      synthetic humanized VL region sequence

<400> SEQUENCE: 21
```

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly His Thr Leu Pro Arg
                85                  90                  95

Thr Phe Gly Gly Gly Thr Lys Val Glu Ile Lys
            100                 105
```

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: K44VHa-N56Q
      synthetic humanized VL + human CL region sequence

<400> SEQUENCE: 22

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly His Thr Leu Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 23
<211> LENGTH: 116
<212> TYPE: PRT

-continued

```
<213> ORGANISM: Artificial Sequence
<220> FEATURE:
<223> OTHER INFORMATION: Description of Artificial Sequence:
      K44VHa-6N56Q synthetic humanized VH region sequence

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met His Trp Val Arg Gln Ala Pro Gly Gln Gly Leu Glu Trp Met
            35                  40                  45

Gly Thr Ile Asp Pro Ser Asp Gln Tyr Thr Ile Tyr Ser Gln Asn Phe
        50                  55                  60

Lys Gly Arg Val Thr Met Thr Val Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Phe Ala Met Asp Tyr Trp Gly Gln Gly Thr Leu Val
            100                 105                 110

Thr Val Ser Ser
            115

<210> SEQ ID NO 24
<211> LENGTH: 446
<212> TYPE: PRT
<213> ORGANISM: Artificial Sequence
<220> FEATURE:
<223> OTHER INFORMATION: Description of Artificial Sequence:
      K44VHa-6N56Q synthetic humanized VH + human CH region sequence

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met His Trp Val Arg Gln Ala Pro Gly Gln Gly Leu Glu Trp Met
            35                  40                  45

Gly Thr Ile Asp Pro Ser Asp Gln Tyr Thr Ile Tyr Ser Gln Asn Phe
        50                  55                  60

Lys Gly Arg Val Thr Met Thr Val Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Phe Ala Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
                195                 200                 205
Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence:
      K44VHa-6N56Q synthetic humanized VL region sequence

<400> SEQUENCE: 25

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly His Thr Leu Pro Arg
                85                  90                  95

Thr Phe Gly Gly Gly Thr Lys Val Glu Ile Lys
            100                 105
```

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence:
    K44VHa-6N56Q synthetic humanized VL + human CL region sequence

<400> SEQUENCE: 26

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly His Thr Leu Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 357
<212> TYPE: DNA
<213> ORGANISM: Mus sp.

<400> SEQUENCE: 27
gaagtggagc ttgtggagtc tggaggaggc ttggtgcaac ctggaggatc catgaaactc        60
tcttgtgctg cctctggatt cactttagt gacgcctgga tggactgggt ccgccagtct       120
ccagagaagg ggcttgagtg ggttgctgaa attagaagcg aagctgataa tcatccaaca       180
tactatgctg agtctgtgaa agggaggttc accatctcaa gagatgattc caaaagtagt       240
gtctacctgc aaatgaacag cttaagagct gaagacagtg gcatttatta ctgtactgaa       300
tatgattacg aggggtttgt acactggggc caggggacgc tggtcactgt ctctgca         357

<210> SEQ ID NO 28
<211> LENGTH: 119
<212> TYPE: PRT
<213> ORGANISM: Mus sp.

<400> SEQUENCE: 28

Glu Val Glu Leu Val Glu Ser Gly Gly Gly Leu Val Gln Pro Gly Gly
1               5                   10                  15
Ser Met Lys Leu Ser Cys Ala Ala Ser Gly Phe Thr Phe Ser Asp Ala
            20                  25                  30
Trp Met Asp Trp Val Arg Gln Ser Pro Glu Lys Gly Leu Glu Trp Val
        35                  40                  45
Ala Glu Ile Arg Ser Glu Ala Asp Asn His Pro Thr Tyr Tyr Ala Glu
    50                  55                  60
Ser Val Lys Gly Arg Phe Thr Ile Ser Arg Asp Asp Ser Lys Ser Ser
65                  70                  75                  80
Val Tyr Leu Gln Met Asn Ser Leu Arg Ala Glu Asp Ser Gly Ile Tyr
                85                  90                  95
Tyr Cys Thr Glu Tyr Asp Tyr Glu Gly Phe Val His Trp Gly Gln Gly
            100                 105                 110
Thr Leu Val Thr Val Ser Ala
        115

<210> SEQ ID NO 29
<211> LENGTH: 5
<212> TYPE: PRT
<213> ORGANISM: Mus sp.

<400> SEQUENCE: 29

Asp Ala Trp Met Asp
1               5

<210> SEQ ID NO 30
<211> LENGTH: 19
<212> TYPE: PRT
<213> ORGANISM: Mus sp.

<400> SEQUENCE: 30

Glu Ile Arg Ser Glu Ala Asp Asn His Pro Thr Tyr Tyr Ala Glu Ser
1               5                   10                  15
Val Lys Gly

<210> SEQ ID NO 31
<211> LENGTH: 8
<212> TYPE: PRT
<213> ORGANISM: Mus sp.

<400> SEQUENCE: 31

Tyr Asp Tyr Glu Gly Phe Val His
1               5

<210> SEQ ID NO 32
<211> LENGTH: 333
<212> TYPE: DNA
<213> ORGANISM: Mus sp.

<400> SEQUENCE: 32
gacattgtgc tgacacagtc tcctgcttca ctagctgtat ctctggggca gagggccacc      60
atctcatgca gggccagcaa aagtgtcagt acatatggct atagttatat gcactggtac     120
caacagaaac caggacagcc acccaaactc ctcatctatc ttgcatccaa cctagaatct     180
ggggtccctg ccaggttcag tgcagtggga tctgggacag acttcaccct caacatccat     240
cctgtggagg aggaggatgc tgcaacctat tactgtcaac acagtaggga gcttccgctc     300
acgttcggtg ctgggaccaa gctggagctg aag                              333

<210> SEQ ID NO 33
<211> LENGTH: 111
<212> TYPE: PRT
<213> ORGANISM: Mus sp.

<400> SEQUENCE: 33

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Tyr
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 34
<211> LENGTH: 15
<212> TYPE: PRT
<213> ORGANISM: Mus sp.

<400> SEQUENCE: 34

Arg Ala Ser Lys Ser Val Ser Thr Tyr Gly Tyr Ser Tyr Met His
1               5                   10                  15

<210> SEQ ID NO 35
<211> LENGTH: 7
<212> TYPE: PRT
<213> ORGANISM: Mus sp.

<400> SEQUENCE: 35

Leu Ala Ser Asn Leu Glu Ser
1               5

<210> SEQ ID NO 36
<211> LENGTH: 9
<212> TYPE: PRT
<213> ORGANISM: Mus sp.

<400> SEQUENCE: 36

Gln His Ser Arg Glu Leu Pro Leu Thr
1               5

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Hu-9F11
      VH-4, VH-11 synthetic humanized VH region sequence

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala

```
                    20                  25                  30

Trp Met Asp Trp Val Arg Gln Ala Pro Gly Lys Gly Leu Glu Trp Val
            35                  40                  45

Ala Glu Ile Arg Ser Glu Ala Asp Asn His Pro Thr Tyr Tyr Ala Glu
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Thr Glu Tyr Asp Tyr Glu Gly Phe Val His Trp Gly Gln Gly
                100                 105                 110

Thr Leu Val Thr Val Ser Ser
            115

<210> SEQ ID NO 38
<211> LENGTH: 119
<212> TYPE: PRT
<213> ORGANISM: Artificial Sequence
<220> FEATURE:
<223> OTHER INFORMATION: Description of Artificial Sequence: Hu-9F11
      VH-6 synthetic humanized VH region sequence

<400> SEQUENCE: 38

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
            35                  40                  45

Ala Glu Ile Arg Ser Glu Ala Asp Asn His Pro Thr Tyr Tyr Ala Glu
 50                  55                  60

Ser Val Lys Gly Arg Phe Thr Ile Ser Arg Asp Asp Ser Lys Asn Ser
 65                  70                  75                  80

Val Tyr Leu Gln Met Asn Ser Leu Lys Thr Glu Asp Thr Ala Val Tyr
                85                  90                  95

Tyr Cys Thr Glu Tyr Asp Tyr Glu Gly Phe Val His Trp Gly Gln Gly
                100                 105                 110

Thr Leu Val Thr Val Ser Ser
            115

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Hu-9F11 VL,
      VL-4, VL-6 synthetic humanized VL region sequence

<400> SEQUENCE: 39

Asp Ile Val Met Thr Gln Thr Pro Leu Ser Leu Ser Val Thr Pro Gly
 1               5                  10                  15

Gln Pro Ala Ser Ile Ser Cys Arg Ala Ser Lys Ser Val Ser Thr Tyr
            20                  25                  30

Gly Tyr Ser Tyr Met His Trp Tyr Leu Gln Lys Pro Gly Gln Pro Pro
            35                  40                  45

Gln Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Lys Ile Ser
```

```
                65                  70                  75                  80
Arg Val Glu Ala Glu Asp Val Gly Val Tyr Tyr Cys Gln His Ser Arg
                    85                  90                  95

Glu Leu Pro Leu Thr Phe Gly Gln Gly Thr Lys Leu Glu Ile Lys
                100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Hu-9F11
      VL-11 synthetic humanized VL region sequence

<400> SEQUENCE: 40

Asp Ile Val Leu Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Tyr
                20                  25                  30

Gly Tyr Ser Tyr Met His Trp Tyr Leu Gln Lys Pro Gly Gln Pro Pro
            35                  40                  45

Gln Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                    85                  90                  95

Glu Leu Pro Leu Thr Phe Gly Gln Gly Thr Lys Leu Glu Ile Lys
                100                 105                 110

<210> SEQ ID NO 41
<211> LENGTH: 363
<212> TYPE: DNA
<213> ORGANISM: Mus sp.

<400> SEQUENCE: 41
gaagtgcagc tggtggagtc tgggggaggc tcagtgaagc tggagggtc cctgaaactc       60 tcctgtgcag cctctggact cactttcagt cactattaca tgtattgggt tcgccagacg      120
ccggaaaaga ggctggagtg ggtcgcaatc attagtgatg gtggtgatta cacccactac      180
tcagacagtg tgaaggggcg attcaccatc tccagagaca tgccaagaa caacctgtac       240 ctacaaatga gcagtctgca gtctgaggac acagccatgt attactgtgc aggagattac      300
ggatatggtt acgaggggtg gtttgcttac tggggccaag gactctggt cactgtctct       360 aca                                                                    363

<210> SEQ ID NO 42
<211> LENGTH: 121
<212> TYPE: PRT
<213> ORGANISM: Mus sp.

<400> SEQUENCE: 42

Glu Val Gln Leu Val Glu Ser Gly Gly Gly Ser Val Lys Pro Gly Gly
1               5                   10                  15

Ser Leu Lys Leu Ser Cys Ala Ala Ser Gly Leu Thr Phe Ser His Tyr
                20                  25                  30

Tyr Met Tyr Trp Val Arg Gln Thr Pro Glu Lys Arg Leu Glu Trp Val
            35                  40                  45
```

```
Ala Ile Ile Ser Asp Gly Gly Asp Tyr Thr His Tyr Ser Asp Ser Val
        50                  55                  60

Lys Gly Arg Phe Thr Ile Ser Arg Asp Asn Ala Lys Asn Asn Leu Tyr
 65                  70                  75                  80

Leu Gln Met Ser Ser Leu Gln Ser Glu Asp Thr Ala Met Tyr Tyr Cys
                 85                  90                  95

Ala Gly Asp Tyr Gly Tyr Gly Tyr Glu Gly Trp Phe Ala Tyr Trp Gly
               100                 105                 110

Gln Gly Thr Leu Val Thr Val Ser Thr
            115                 120
```

<210> SEQ ID NO 43
<211> LENGTH: 5
<212> TYPE: PRT
<213> ORGANISM: Mus sp.

<400> SEQUENCE: 43

```
His Tyr Tyr Met Tyr
 1               5
```

<210> SEQ ID NO 44
<211> LENGTH: 17
<212> TYPE: PRT
<213> ORGANISM: Mus sp.

<400> SEQUENCE: 44

```
Ile Ile Ser Asp Gly Gly Asp Tyr Thr His Tyr Ser Asp Ser Val Lys
 1               5                  10                  15

Gly
```

<210> SEQ ID NO 45
<211> LENGTH: 12
<212> TYPE: PRT
<213> ORGANISM: Mus sp.

<400> SEQUENCE: 45

```
Asp Tyr Gly Tyr Gly Tyr Glu Gly Trp Phe Ala Tyr
 1               5                  10
```

<210> SEQ ID NO 46
<211> LENGTH: 321
<212> TYPE: DNA
<213> ORGANISM: Mus sp.

<400> SEQUENCE: 46

```
gacattgtga tgacccagtc tcaaaaattc atgtccacat cagtaggaga cagggtcagc    60
gtcacctgca aggccagtca gaatgtggat acttatgtag cctggtatca acagaaacca   120
gggcaatctc ctaaagcact gatttattcg acatcctatc ggtacagtgg agtccctgat   180
cgcttcacag gcagtggatc tgggacagat ttcactctca ccatcagtaa tgtgcagtct   240
gaagacttgg cagagtattt ctgtcagcaa tataacagct atccgtggac gttcggtgga   300
ggcactaagc tggaaatcaa a                                            321
```

<210> SEQ ID NO 47
<211> LENGTH: 107
<212> TYPE: PRT
<213> ORGANISM: Mus sp.

<400> SEQUENCE: 47

```
Asp Ile Val Met Thr Gln Ser Gln Lys Phe Met Ser Thr Ser Val Gly
```

```
              1               5                  10                  15
Asp Arg Val Ser Val Thr Cys Lys Ala Ser Gln Asn Val Asp Thr Tyr
                    20                  25                  30

Val Ala Trp Tyr Gln Gln Lys Pro Gly Gln Ser Pro Lys Ala Leu Ile
            35                  40                  45

Tyr Ser Thr Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Trp
                85                  90                  95

Thr Phe Gly Gly Gly Thr Lys Leu Glu Ile Lys
                100                 105

<210> SEQ ID NO 48
<211> LENGTH: 11
<212> TYPE: PRT
<213> ORGANISM: Mus sp.

<400> SEQUENCE: 48

Lys Ala Ser Gln Asn Val Asp Thr Tyr Val Ala
1               5                   10

<210> SEQ ID NO 49
<211> LENGTH: 7
<212> TYPE: PRT
<213> ORGANISM: Mus sp.

<400> SEQUENCE: 49

Ser Thr Ser Tyr Arg Tyr Ser
1               5

<210> SEQ ID NO 50
<211> LENGTH: 9
<212> TYPE: PRT
<213> ORGANISM: Mus sp.

<400> SEQUENCE: 50

Gln Gln Tyr Asn Ser Tyr Pro Trp Thr
1               5

<210> SEQ ID NO 51
<211> LENGTH: 360
<212> TYPE: DNA
<213> ORGANISM: Mus sp.

<400> SEQUENCE: 51
gaggtccagc tgcaacagtt tggagctgag gtggtgaagc ctggggcttc agtgaagatg    60
tcctgcaagg cttctggcta cacattcact gactacaaca tgaactgggt gaagcagagc   120
catgaaaaga gccttgagtg gattggagat attcatccta gtttcatag tactaactac    180 aaccagaaat tcaagggaaa ggccacattg actatagaca cgtcctccag cacagcctac   240
atggagctcc gcaacctgac atctgaggac actgcagtct attactgtgc acgagttggt   300
aactacgttt actttgttat ggactactgg ggtcaaggaa cctcagtcac cgtctcctca   360

<210> SEQ ID NO 52
<211> LENGTH: 120
<212> TYPE: PRT
<213> ORGANISM: Mus sp.
```

<400> SEQUENCE: 52

Glu Val Gln Leu Gln Gln Phe Gly Ala Glu Val Val Lys Pro Gly Ala
1               5                   10                  15

Ser Val Lys Met Ser Cys Lys Ala Ser Gly Tyr Thr Phe Thr Asp Tyr
            20                  25                  30

Asn Met Asn Trp Val Lys Gln Ser His Glu Lys Ser Leu Glu Trp Ile
        35                  40                  45

Gly Asp Ile His Pro Lys Phe His Ser Thr Asn Tyr Asn Gln Lys Phe
    50                  55                  60

Lys Gly Lys Ala Thr Leu Thr Ile Asp Thr Ser Ser Ser Thr Ala Tyr
65                  70                  75                  80

Met Glu Leu Arg Asn Leu Thr Ser Glu Asp Thr Ala Val Tyr Tyr Cys
                85                  90                  95

Ala Arg Val Gly Asn Tyr Val Tyr Phe Val Met Asp Tyr Trp Gly Gln
            100                 105                 110

Gly Thr Ser Val Thr Val Ser Ser
        115                 120

<210> SEQ ID NO 53
<211> LENGTH: 5
<212> TYPE: PRT
<213> ORGANISM: Mus sp.

<400> SEQUENCE: 53

Asp Tyr Asn Met Asn
1               5

<210> SEQ ID NO 54
<211> LENGTH: 10
<212> TYPE: PRT
<213> ORGANISM: Mus sp.

<400> SEQUENCE: 54

Asp Tyr Asn Met Asn Asp Tyr Asn Met Asn
1               5                   10

<210> SEQ ID NO 55
<211> LENGTH: 11
<212> TYPE: PRT
<213> ORGANISM: Mus sp.

<400> SEQUENCE: 55

Val Gly Asn Tyr Val Tyr Phe Val Met Asp Tyr
1               5                   10

<210> SEQ ID NO 56
<211> LENGTH: 321
<212> TYPE: DNA
<213> ORGANISM: Mus sp.

<400> SEQUENCE: 56

```
agtattgtga tgacccagac tcccaaattc ctgcttgtat cagcaggaga cagggttact    60
ataacctgca aggccagtca gagtgtgagt aatgatgtag cttggtacca acagaagcca   120
gggcagtctc ctaaactcct gatatactat gcatccaatc gctacactgg agtccctgat   180
cgcttcagtg gcagtggata tgggacggat ttcactttca ccatcagcac tgtgcaggct   240
gaagacctgg cagtttattt ctgtcagcag gattatacct ctccgtggac gttcggtgga   300
ggcaccaagc tggaaatcaa a                                             321
```

<210> SEQ ID NO 57
<211> LENGTH: 107
<212> TYPE: PRT
<213> ORGANISM: Mus sp.

<400> SEQUENCE: 57

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Lys
            100                 105

<210> SEQ ID NO 58
<211> LENGTH: 11
<212> TYPE: PRT
<213> ORGANISM: Mus sp.

<400> SEQUENCE: 58

Lys Ala Ser Gln Ser Val Ser Asn Asp Val Ala
1               5                   10

<210> SEQ ID NO 59
<211> LENGTH: 7
<212> TYPE: PRT
<213> ORGANISM: Mus sp.

<400> SEQUENCE: 59

Tyr Ala Ser Asn Arg Tyr Thr
1               5

<210> SEQ ID NO 60
<211> LENGTH: 9
<212> TYPE: PRT
<213> ORGANISM: Mus sp.

<400> SEQUENCE: 60

Gln Gln Asp Tyr Thr Ser Pro Trp Thr
1               5

<210> SEQ ID NO 61
<211> LENGTH: 116
<212> TYPE: PRT
<213> ORGANISM: Artificial Sequence
<220> FEATURE:
<223> OTHER INFORMATION: Description of Artificial Sequence: Synthetic
      humanized version of 19E3 VH sequence

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

```
Trp Met His Trp Val Arg Gln Ala Pro Gly Gln Gly Leu Glu Trp Met
            35                  40                  45

Gly Thr Ile Asp Pro Ser Asp Asn Tyr Thr Ile Tyr Ser Gln Asn Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Tyr Gly Phe Ala Met Asp Tyr Trp Gly Gln Gly Thr Leu Val
                100                 105                 110

Thr Val Ser Ser
        115

<210> SEQ ID NO 62
<211> LENGTH: 116
<212> TYPE: PRT
<213> ORGANISM: Artificial Sequence
<220> FEATURE:
<223> OTHER INFORMATION: Description of Artificial Sequence: Synthetic
      humanized version of 19E3 VH sequence

<400> SEQUENCE: 62

Gln Val Gln Leu Gln Gln Pro Gly Ser Glu Leu Val Met Pro Gly Ala
 1               5                  10                  15

Ser Val Lys Met Ser Cys Lys Ala Ser Gly Tyr Ile Phe Thr Asp Tyr
                20                  25                  30

Trp Met His Trp Val Arg Gln Ala Pro Gly Gln Gly Leu Glu Trp Met
            35                  40                  45

Gly Thr Ile Asp Pro Ser Asp Asn Tyr Thr Ile Tyr Ser Gln Asn Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Tyr Gly Phe Ala Met Asp Tyr Trp Gly Gln Gly Thr Leu Val
                100                 105                 110

Thr Val Ser Ser
        115

<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      humanized version of 19E3 VH sequence

<400> SEQUENCE: 63

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Trp Met His Trp Val Arg Gln Ala Pro Gly Gln Gly Leu Glu Trp Met
            35                  40                  45

Gly Thr Ile Asp Pro Ser Asp Asn Tyr Thr Ile Tyr Ser Gln Asn Phe
 50                  55                  60

Lys Gly Lys Ala Thr Leu Thr Val Asp Glu Ser Ser Ser Thr Ala Tyr
 65                  70                  75                  80
```

```
Met Leu Leu Ser Ser Leu Thr Ser Glu Asp Ser Ala Val Tyr Phe Cys
                85                  90                  95

Ala Arg Tyr Gly Phe Ala Met Asp Tyr Trp Gly Gln Gly Thr Leu Val
            100                 105                 110

Thr Val Ser Ser
        115

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized version of 19E3 VL sequence

<400> SEQUENCE: 64

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly His Thr Leu Pro Arg
                85                  90                  95

Thr Phe Gly Gly Gly Thr Lys Val Glu Ile Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized version of 19E3 VL sequence

<400> SEQUENCE: 65

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Arg
                85                  90                  95

Thr Phe Gly Gly Gly Thr Lys Val Glu Ile Lys
            100                 105

<210> SEQ ID NO 66
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 66

Thr Ile Asp Pro Ser Asp Gln Tyr Thr Ile Tyr Ser Gln Asn Phe Lys
1               5                   10                  15

Gly

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 67

His His His His His His
1               5
```

ANTIBODIES SPECIFIC FOR IL-21 AND USES THEREOF

RELATED APPLICATIONS

This application is a national stage filing under 35 U.S.C. § 371 of International Application No. PCT/US2015/024650, filed on Apr. 7, 2015, which claims the benefit of priority of U.S. Provisional Patent Application No. 61/976,684, filed Apr. 8, 2014, the contents of which are hereby incorporated by reference in its entireties. International Application No. PCT/US2015/024650 was published under PCT Article 21(2) in English.

REFERENCE TO SEQUENCE LISTING SUBMITTED ELECTRONICALLY

The content of the electronically submitted sequence listing in ASCII text file (Name: 113065-0118_SL.txt; Size: 56,495 bytes; and Date of Creation: Jan. 27, 2017) is incorporated herein by reference in its entirety.

BACKGROUND

This disclosure provides compositions that specifically bind to IL-21 and methods for the use of such compositions, e.g., for the treatment or prevention of an inflammatory or autoimmune disease or disorder.

IL-21 belongs to a family of cytokines that includes IL-2, IL-4, IL-7, IL-9 and IL-15, all of which bind to private (or shared) receptors in complex with the common cytokine receptor gamma-chain (γc). Most cytokines in this family are critically important for both the maintenance and function of T cells, B cells, and NK cells. The receptor for IL-21 is widely distributed on lympho-hematopoietic and non-hematopoietic cells, and IL-21 plays many roles.

For example, engagement of IL-21R by IL-21 leads to activation of several signaling pathways, including the Jak/STAT pathway (Davis, I D, et al., (2007) *Clin Cancer Res* 13, 3630-3636; Fuqua, C F, et al., (2008) *Cytokine* 44, 101-107; Habib, T, et al., (2002) *Biochemistry* 41, 8725-8731). More specifically, IL-21 activates STAT1, STAT3 and STAT5, indicated by increased phosphorylation of these molecules within the cell (Asao, H, et al., (2001) *J Immunol* 167, 1-5; Diehl, S A, et al., (2008) *J Immunol* 180, 4805-4815; Scheeren, F A, et al., (2008) *Blood* 111, 4706-4715; Zeng, R, et al., (2007) *Blood* 109, 4135-4142). Activation of STAT3 in particular has been shown to play a critical role in regulating human B cell responses to IL-21 (Avery, D T, et al., (2008) *J Immunol* 181, 1767-1779; Avery, D T, et al., *J Exp Med* 207, 155-171).

Moreover, IL-21 contributes to maintenance and function of CD8+ memory T cells, and NK cells, promotes the generation of Th17 and T follicular helper (Tfh) cells in the mouse (and perhaps human), and inhibits regulatory T cells (Treg) cell generation. IL-21 has been shown to modulate the activity of NK cells including effects on their maturation growth and cytolytic activity (Spolski, R, and Leonard, W J, (2008) *Curr Opin Immunol* 20, 295-301). Additionally, IL-21 has been shown to promote IFNγ production by both primary NK cells as well as the human NK cell line, NK-92 (Kasaian, M T, et al., (2002) *Immunity* 16, 559-569; Strengell, M, et al., (2003) *J Immunol* 170, 5464-5469). IL-21 also has a variety of effects on non-hematopoietic cells, such as stromal cells where it induces inflammation through matrix metalloproteinase (MMP) release (Monteleone et al., (2006) *Gut* 55, 1774-1780).

One principal non-redundant role of IL-21 is the promotion of B cell activation, differentiation or death during humoral immune responses. The effect of IL-21 on human B cells has been extensively studied. IL-21 has a profound impact on B cell survival, activation, and proliferation as well as on the differentiation of B cells into Ig secreting plasma cells (PCs) (Avery, D T, et al., (2008) *J Immunol* 181, 1767-1779; Avery, D T, et al., *J Exp Med* 207, 155-171); Bryant, V L, et al., (2007) *J Immunol* 179, 8180-8190; Ettinger, R, et al., (2005) *J Immunol* 175, 7867-7879; Parrish-Novak, J, et al., (2000) *Nature* 408, 57-63; Pene, J, et al., (2004) *J Immunol* 172, 5154-5157). Furthermore, increased IL-21 production is characteristic of certain autoimmune diseases and is likely to contribute to autoantibody production as well as pathologic features of autoimmune disease. Activation of B cells in vivo can be driven by interactions with activated T cells that express costimulatory molecules such as CD40L and produce B cell tropic cytokines such as IL-21.

Overexpression of IL-21 is a feature of many inflammatory, immune-mediated, or autoimmune diseases or disorders, and is likely to be an important driver of autoantibody production as well as pathologic features of autoimmune disease (Nakou et al., (2013) *Clin. Exp. Rheumatol.* 31, 172-179). The critical role of IL-21 in promoting humoral immune responses makes it an important focus of potential therapeutic interventions in conditions characterized by over-production of both IL-21 and pathogenic autoantibodies (Dolff et al., (2011) *Arthritis Res. Ther.* 13, R157; Kang et al., (2011) *Arthritis Res. Ther.* 13, R179; McGuire et al., (2011) *Immunity* 34, 602-615; Liu et al., (2012) *Arthritis Res. Ther.* 14, R255; Terrier et al., (2012) *Arthritis Rheum.* 64, 2001-2011; Li Q et al., (2013) *PLoS One* 8, e68145; Li Y et al., (2014) *Neurol. Sci.* 35, 29-34). Neutralization of IL-21 in settings of autoimmunity is therefore expected to impact several cell populations believed to be involved in the pathogenesis of immune-mediated disease. Such diseases or disorders include, without limitation, vasculitis, e.g., Anti-neutrophil cytoplasm antibodies (ANCA) or giant cell arteritis (GCA) vasculitis, Sjögren's syndrome, inflammatory bowel disease, Pemphigus vulgaris, lupus nephritis, psoriasis, thyroiditis, Type I Diabetes, Idiopathic thrombocytopenic purpura (ITP), Ankylosing spondylitis, Multiple sclerosis, systemic lupus erythematosus, rheumatoid arthritis, Crohn's disease Myasthenia Gravis and Graft-versus-host disease (GVHD).

Anti-neutrophil cytoplasm antibodies (ANCA)-associated vasculitis (AAV) pathogenesis is typified by major autoantibodies to proteinase 3 (PR3) and myeloperoxidase (MPO). IL-21-producing CD4+ T cells are expanded in the blood (Abdulahad et al., (2013) *Arth Res & Ther* 15:R70). Elevated IL-21 is present in AAV serum relative to healthy controls, and exogenous IL-21 induces ANCA auto-antibody secretion in vitro from PBMCs isolated from AAV patients in vitro. AAV is made up of Granulomatosis with polyangiitis, formerly Wegener's granulomatosis, (GPA), eosinophilic granulomatosis with polyangiitis, also known as the Churg-Strauss syndrome (CSS) and microscopic polyangiitis (MPA). They are usually lumped together but epidemiologically the prevalence and distribution is different. Current treatments include corticosteroids, biological, e.g., rituximab, immunosuppressive drugs, antibiotics, or plasmapheresis, but the prognosis for patients remains poor. There remains an unmet need to find treatments for AAV.

Sjögren's syndrome (SS) is an autoimmune disease characterized by autoantibodies such as rheumatoid factor (RF) as well as autoantibodies to several nuclear antigens such as Ro/La. SS is the second most prevalent autoimmune condition after RA. There are at least 1 million primary Sjögren's patients in the US, of which 90% are female. SS affects salivary glands, causing, e.g., dry mouth and eyes. Additionally, SS may affect other organs of the body, including the kidneys, blood vessels, lungs, liver, pancreas, peripheral nervous system and brain and is associated with other autoimmune diseases such as lupus and rheumatoid arthritis. Highly elevated serum IL-21 levels correlate with increased IgG1 and the presence of autoantibodies (Kang, 2011). Elevated IL-21 and IL-21R levels can be found in ectopic follicles of salivary gland (Kang, 2011). Moreover, IL-21 is known to play a direct role in NK cell activation and cytotoxicity. Increased numbers of tissue-resident NK cells that overexpress the activating receptor NKp30 are found in salivary glands of primary Sjögren's syndrome patients, and correlate with focus score (Rusakiewicz et al., (2013) *Sci. Transl. Med.* 5, 195ra96). These NK cells are implicated in the pathogenesis of disease through direct NK cell-stromal cell cross talk resulting in tissue damage. IL-21 and its receptor are also expressed on salivary gland infiltrates (Kang, 2011), and IL-21 producing memory CCR9+CD4+ Tfh cells have been reported to be expanded in the circulation of most SS patients (McGuire, 2011). In addition, an increased level of Tfh cells in patients with elevated IL-21 is associated with extraglandular manifestations (Szabo et al., (2013) *Clinical Immunol* 147, 95-104). Preclinical animal models have demonstrated benefit from IL-21 inhibition (Liu et al. (2012) *J Oral Pathol Med*). There is no cure for SS; current treatments are of limited efficacy and none can be considered disease-modifying. Mild to moderate disease is treated symptomatically by over the counter medications. Severe disease is currently treated with hydroxychloroquine, steroids, methotrexate, azathioprine, or off-label rituximab. There remains an unmet need to find effective treatments for SS.

Neutralization of IL-21 has potential utility in several indications, including primary SS and vasculitis (Kang, 2011; Bae et al., (2012) *Allergy Asthma Immunol Res.* 4, 351-356; Terrier, 2012; Abdulahad, 2013; Szabo, 2013).

The effect of IL-21 on graft-vs-host disease (GVHD) has been extensively studied. When delivered by a hydrodynamic gene system, IL-21 has been shown to greatly accelerate human to mouse xenogeneic GVHD and found to increase B cells, plasma cells and immunoglobulin (Wu et al., (2013) *Protein Cell* 4, 863-871). Conversely, blockade of IL-21 in this system was reported to decrease gastrointestinal track injury, splenic Th1 cytokines, and protect from lethality (Hippen et al., (2012) *Blood* 119, 619-628). Moreover, protection from GVHD was reported to be dependent on the generation of Tregs (Hippen et al., 2012).

This disclosure provides compositions that specifically bind to IL-21, and methods for the use of such compositions, e.g., for the treatment or prevention of an inflammatory, immune-mediated, or autoimmune disease or disorder.

In a particular aspect, this disclosure provides for the treatment or prevention of GVHD using a composition comprising an antibody or fragment thereof that specifically binds to IL-21. For instance, it has been shown in a xenogeneic mouse model of GVHD that an anti-IL-21 composition blocks de novo-produced human IL-21. This composition potently inhibits GVHD-induced wasting disease and lethality when given both prophylactically, as well as therapeutically.

BRIEF SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

The disclosure provides IL-21 binding molecules, e.g., anti-IL-21 antibodies or antigen-binding fragments thereof, e.g., monoclonal antibodies capable of inhibiting interaction of IL-21 and its receptor, and inhibiting IL-21 activity.

In some instances, an isolated binding molecule or antigen-binding fragment thereof which specifically binds to an epitope of IL-21, wherein the binding molecule specifically binds to the same IL-21 epitope as an antibody or antigen-binding fragment thereof comprises the heavy chain variable region (VH) and light chain variable region (VL) of 19E3, 9F11, 8B6, or 9H10.

In some instances, an isolated binding molecule or antigen-binding fragment thereof which specifically binds to IL-21, and competitively inhibits IL-21 binding by an antibody or antigen-binding fragment thereof comprises the VH and VL of 19E3, 9F11, 8B6, or 9H10. In some instances, the VH and VL of 19E3 comprise SEQ ID NOs: 6 and 11, respectively, the VH and VL of 9F11 comprise SEQ ID NOs: 28 and 33, respectively, the VH and VL of 8B6 comprise SEQ ID NOs: 42 and 47, respectively, and the VH and VL of 9H10 comprise SEQ ID NOs: 52 and 57, respectively.

In some instances, an isolated binding molecule or antigen-binding fragment thereof which specifically binds to IL-21 comprises an antibody VL, wherein the VL comprises VL-CDR1, VL-CDR2, and VL-CDR3 amino acid sequences identical to, or identical except for four, three, two, or one amino acid substitutions in one or more of the VL-CDRS to: SEQ ID NOs: 12, 13, and 14, SEQ ID NOs: 34, 35, and 36, SEQ ID NOs: 48, 49, and 50, or SEQ ID NOs: 58, 59, and 60, respectively.

In some instances, an isolated binding molecule or antigen-binding fragment thereof which specifically binds to IL-21 comprises an antibody VH, wherein the VH comprises VH-CDR1, VH-CDR2, and VH-CDR3 amino acid sequences identical to, or identical except for four, three, two, or one amino acid substitutions in one or more of the VH-CDRS to: SEQ ID NOs: 7, 8, and 9, SEQ ID NOs: 29, 30, and 31, SEQ ID NOs: 43, 44, and 45, or SEQ ID NOs: 53, 54, and 55, respectively.

In some instances, an isolated binding molecule or antigen-binding fragment thereof which specifically binds to IL-21 comprises an antibody VL, wherein the VL comprises an amino acid sequence at least 85%, 90%, 95%, or 100% identical to a reference amino acid sequence selected from the group consisting of SEQ ID NO: 11, SEQ ID NO: 17, SEQ ID NO: 21, SEQ ID NO: 25, SEQ ID NO: 33, SEQ ID NO: 39, SEQ ID NO: 40, SEQ ID NO: 47, and SEQ ID NO: 57.

In some instances, an isolated binding molecule or antigen-binding fragment thereof which specifically binds to IL-21 comprises an antibody VH, wherein the VH comprises an amino acid sequence at least 85%, 90%, 95%, or 100% identical to a reference amino acid sequence selected from the group consisting of SEQ ID NO: 6, SEQ ID NO: 15, SEQ ID NO: 19, SEQ ID NO: 23, SEQ ID NO: 28, SEQ ID NO: 37, SEQ ID NO: 38, SEQ ID NO: 42 and SEQ ID NO: 52.

In some instances, the binding molecule or fragment thereof comprises an antibody or antigen-binding fragment thereof.

In some instances, an isolated antibody or antigen-binding fragment thereof which specifically binds to IL-21 comprises a VL and a VH comprising VL-CDR1, VL-CRD2, VL-CDR3, VH-CDR1, VH-CDR2, and VH-CDR3 amino acid sequences identical or identical except for four, three, two, or one amino acid substitutions in one or more CDRs to: SEQ ID NOs: 12, 13, 14, 7, 8, and 9, SEQ ID NOs: 34, 35, 36, 29, 30, and 31, SEQ ID NOs: 48, 49, 50, 43, 44, and 45, or SEQ ID NOs: 58, 59, 60, 53, 54, and 55, respectively.

In some instances, an isolated antibody or antigen-binding fragment thereof which specifically binds to IL-21, wherein the antibody or antigen-binding fragment comprises a VH and a VL, wherein the VH and VL comprise, respectively, amino acid sequences at least 85%, 90%, 95%, or 100% identical to reference amino acid sequences selected from the group consisting of SEQ ID NO: 6 and SEQ ID NO: 11, SEQ ID NO: 15 and SEQ ID NO: 17, SEQ ID NO: 19 and SEQ ID NO: 21, SEQ ID NO: 23 and SEQ ID NO: 25, SEQ ID NO: 28 and SEQ ID NO: 33, SEQ ID NO: 37 and SEQ ID NO: 39, SEQ ID NO: 38 and SEQ ID NO: 39, SEQ ID NO: 37 and 40, SEQ ID NO: 42 and SEQ ID NO: 47, and SEQ ID NO: 52 and SEQ ID NO: 57, respectively.

In some instances, the antibody or antigen-binding fragment comprises a VH and a VL, wherein the VH comprises the amino acid sequence SEQ ID NO: 19 and the VL comprises the amino acid sequence SEQ ID NO: 21. In some instances, the antibody or antigen-binding fragment thereof comprises a heavy chain constant region or fragment thereof. In some instances, the heavy chain constant region or fragment thereof is an IgG constant region. In some instances, the IgG constant domain comprises one or more amino acid substitutions relative to a wild-type IgG constant domain wherein the modified IgG has an increased half-life compared to the half-life of an IgG having the wild-type IgG constant domain. In some instances, the IgG constant domain comprises one or more amino acid substitutions of amino acid residues at positions 251-257, 285-290, 308-314, 385-389, and 428-436, wherein the amino acid position numbering is according to the EU index as set forth in Kabat. In some instances, at least one IgG constant domain amino acid substitution is selected from the group consisting of:

(a) substitution of the amino acid at Kabat position 252 with Tyrosine (Y), Phenylalanine (F), Tryptophan (W), or Threonine (T),
(b) substitution of the amino acid at Kabat position 254 with Threonine (T),
(c) substitution of the amino acid at Kabat position 256 with Serine (S), Arginine (R), Glutamine (Q), Glutamic acid (E), Aspartic acid (D), or Threonine (T),
(d) substitution of the amino acid at Kabat position 257 with Leucine (L),
(e) substitution of the amino acid at Kabat position 309 with Proline (P),
(f) substitution of the amino acid at Kabat position 311 with Serine (S),
(g) substitution of the amino acid at Kabat position 428 with Threonine (T), Leucine (L), Phenylalanine (F), or Serine (S),
(h) substitution of the amino acid at Kabat position 433 with Arginine (R), Serine (S), Isoleucine (I), Proline (P), or Glutamine (Q),
(i) substitution of the amino acid at Kabat position 434 with Tryptophan (W), Methionine (M), Serine (S), Histidine (H), Phenylalanine (F), or Tyrosine, and
(j) a combination of two or more of the substitutions.

In some instances, the human IgG constant domain comprises amino acid substitutions relative to a wild-type human IgG constant domain at Kabat positions 252, 254, and 256, wherein
(a) the amino acid at Kabat position 252 is substituted with Tyrosine (Y),
(b) the amino acid at Kabat position 254 is substituted with Threonine (T), and
(c) the amino acid at Kabat position 256 is substituted with Glutamic acid (E).

In some instances, the human IgG constant domain is a human IgG1 constant domain.

In some instances, the heavy chain comprises the amino acid sequence SEQ ID NO: 16, SEQ ID NO: 20, or SEQ ID NO: 24. In some instances, the light chain constant region is selected from the group consisting of a human kappa constant region and a human lambda constant region. In some instances, the light chain constant region is a human kappa constant region. In some instances, the heavy chain and light chain comprise the amino acid sequences SEQ ID NO: 16 and SEQ ID NO: 18, SEQ ID NO: 20 and SEQ ID NO: 22, or SEQ ID NO: 24 and SEQ ID NO: 26, respectively.

In some instances, the antibody or antigen-binding fragment thereof is a murine antibody, a humanized antibody, a chimeric antibody, a monoclonal antibody, a polyclonal antibody, a recombinant antibody, a multispecific antibody, or an antigen-binding fragment thereof. In some instances, the antigen-binding fragment is Fv, Fab, F(ab')2, Fab', dsFv, scFv, and sc(Fv)2.

In some instances, the antibody or antigen-binding fragment thereof can bind to human IL-21 and cynomolgus (cyno) monkey IL-21.

In some instances, the antibody or fragment thereof does not specifically bind to human IL-2, IL-4, IL-7, IL-9, or IL-15.

In some instances, the antibody or fragment thereof inhibits IL-21 binding to the IL-21 receptor.

In some instances, the antibody or fragment thereof is an antagonist of IL-21 activity.

In some instances, the antibody or fragment thereof can inhibit IL-21-mediated phosphorylation of STAT3 in human peripheral blood mononuclear cells (PBMC).

In some instances, the antibody or fragment thereof can inhibit human and cynomolgus monkey IL-21-mediated phosphorylation of STAT3 in human peripheral blood mononuclear cells (PBMC)

In some instances, the antibody or fragment thereof can inhibit IL-21-mediated interferon-gamma (IFN-γ) production by NK cells.

In some instances, the antibody or fragment thereof can inhibit human and cynomolgus monkey IL-21-mediated interferon-gamma (IFN-γ) production by NK cells. In some instances, the NK cells are cultured NK-92 cells.

In some instances, the antibody or fragment thereof can inhibit IL-21-mediated B-cell differentiation into plasma cells.

In some instances, the antibody or fragment thereof can inhibit human and cynomolgus monkey IL-21-mediated differentiation of stimulated B cells into plasma cells.

In some instances, the antibody or fragment thereof can inhibit CD4+ T cell-activated B cell differentiation into plasma cells.

In some instances, the antibody or antigen-binding fragment thereof specifically binds human IL-21 with an affinity characterized by a dissociation constant ($K_D$) of about 100 pM to about 0.1 pM as measured on a Kinetic Exclusion Assay (KinExA) 3000 platform.

In some instances, the antibody or antigen-binding fragment thereof specifically binds cynomolgus monkey IL-21 with an affinity characterized by a dissociation constant ($K_D$) of about 100 pM to about 0.1 pM as measured on a Kinetic Exclusion Assay (KinExA) 3000 platform.

In some instances, the antibody or antigen-binding fragment thereof wherein the $K_D$ for human IL-21 is about 0.515 pM and the $K_D$ for cynomolgus monkey IL-21 is about 0.352 pM.

In some instances, the antibody or fragment thereof is conjugated to an agent selected from the group consisting of an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), and a combination of two or more of any said agents.

In some instances, a composition comprises the antibody or fragment thereof as described herein, and a carrier. Preferably, the carrier is a pharmaceutically acceptable carrier.

In some instances, an isolated polynucleotide comprises a nucleic acid encoding an antibody VL, wherein the VL comprises VL-CDR1, VL-CDR2, and VL-CDR3 amino acid sequences identical to, or identical except for four, three, two, or one amino acid substitutions in one or more of the VL-CDRS to: SEQ ID NOs: 12, 13, and 14, SEQ ID NOs: 34, 35 and 36, SEQ ID NOs: 48, 49, and 50, or SEQ ID NOs: 58, 59, and 60, respectively.

In some instances, an isolated polynucleotide comprises a nucleic acid encoding an antibody VH, wherein the VH comprises VH-CDR1, VH-CDR2, and VH-CDR3 amino acid sequences identical to, or identical except for four, three, two, or one amino acid substitutions in one or more of the VH-CDRS to: SEQ ID NOs: 7, 8, and 9, SEQ ID NOs: 29, 30 and 31, SEQ ID NOs: 43, 44, and 45, or SEQ ID NOs: 53, 54, and 55, respectively.

In some instances, an isolated polynucleotide comprises a nucleic acid encoding an antibody VL, wherein the VL comprises an amino acid sequence at least 85%, 90%, 95%, or 100% identical to a reference amino acid sequence selected from the group consisting of SEQ ID NO: 11, SEQ ID NO: 17, SEQ ID NO: 21, SEQ ID NO: 25, SEQ ID NO: 33, SEQ ID NO: 39, SEQ ID NO: 40, SEQ ID NO: 47, and SEQ ID NO: 57. In some instances, an isolated polynucleotide comprises a nucleic acid encoding an antibody VH, wherein the VH comprises an amino acid sequence at least 85%, 90%, 95%, or 100% identical to a reference amino acid sequence selected from the group consisting of SEQ ID NO: 6, SEQ ID NO: 15, SEQ ID NO: 19, SEQ ID NO: 23, SEQ ID NO: 28, SEQ ID NO: 37, SEQ ID NO: 38, SEQ ID NO: 42 and SEQ ID NO: 52.

In some instances, the polynucleotide described herein comprises a nucleic acid that encodes an antibody or antigen-binding fragment thereof comprising the VH or the VL described herein that can specifically bind to IL-21. In some instances, the antibody or antigen-binding fragment thereof specifically binds to the same epitope as an antibody or antigen-binding fragment thereof comprising the VH and VL of 19E3, 9F11, 8B6, or 9H10.

In some instances, the polynucleotide described herein comprises a nucleic acid that encodes an antibody or antigen-binding fragment thereof comprising the VH or the VL can bind to human and cynomolgus monkey IL-21.

In some instances, a vector comprising the polynucleotide described herein is provided.

In some instances, a composition comprising the polynucleotide described herein or the vector described herein is provided.

In some instances, a polynucleotide or a combination of polynucleotides encoding the binding molecule or antigen-binding fragment thereof as described herein is provided.

In some instances, a polynucleotide or combination of polynucleotides encoding the antibody or antigen-binding fragment thereof described herein is provided.

In some instances, a composition comprises a polynucleotide that comprises a nucleic acid encoding a VH, and a polynucleotide that comprises a nucleic acid encoding a VL, wherein the VL and VH comprise VL-CDR1, VL-CRD2, VL-CDR3, VH-CDR1, VH-CDR2, and VH-CDR3 amino acid sequences identical or identical except for four, three, two, or one amino acid substitutions in one or more CDRs to: SEQ ID NOs: 12, 13, 14, 7, 8, and 9, SEQ ID NOs: 34, 35, 36, 29, 30, and 31, SEQ ID NOs: 48, 49, 50, 43, 44, and 45, or SEQ ID NOs: 58, 59, 60, 53, 54, and 55, respectively.

In some instances, a composition comprises a polynucleotide that comprises a nucleic acid encoding a VH, and a polynucleotide that comprises a nucleic acid encoding a VL, wherein the VL and VH comprise, respectively, amino acid sequences at least 85%, 90%, 95%, or 100% identical to reference amino acid sequences selected from the group consisting of SEQ ID NO: 6 and SEQ ID NO: 11, SEQ ID NO: 15 and SEQ ID NO: 17, SEQ ID NO: 19 and SEQ ID NO: 21, SEQ ID NO: 23 and SEQ ID NO: 25, SEQ ID NO: 28 and SEQ ID NO: 33, SEQ ID NO: 37 and SEQ ID NO: 39, SEQ ID NO: 38 and SEQ ID NO: 39, SEQ ID NO: 37 and 40, SEQ ID NO: 42 and SEQ ID NO: 47, and SEQ ID NO: 52 and SEQ ID NO: 57, respectively.

In some instances, the VH and VL are encoded by nucleic acid sequences at least 85%, 90%, 95%, or 100% identical to reference nucleic acid sequences selected from the group consisting SEQ ID NO:5 and SEQ ID NO:10, SEQ ID NO:27 and SEQ ID NO:32, SEQ ID NO: 41 and SEQ ID NO:46, or SEQ ID NO: 51 and SEQ ID NO:56, respectively.

In some instances, the polynucleotide comprising a nucleic acid encoding a VH and the polynucleotide comprising a nucleic acid encoding a VL are in the same vector. In some instances, the vector as described herein is provided.

In some instances, the polynucleotide comprising a nucleic acid encoding a VH and the polynucleotide comprising a nucleic acid encoding a VL are in different vectors. In some instances, the vectors as described herein are provided.

In some instances, the compositions as described herein include an antibody or antigen-binding fragment thereof that comprises said VH and said VL which can specifically bind to IL-21. In some instances, the antibody or antigen-binding fragment thereof comprising the VH or the VL can bind to human and cynomolgus monkey IL-21. In some instances, the antibody or antigen-binding fragment thereof can specifically bind to the same epitope as an antibody or antigen-binding fragment thereof comprising the VH and VL of 19E3, 9F11, 8B6, or 9H10.

In some instances, host cells comprising polynucleotides as described herein, the compositions as described herein, or the vector or vectors as described herein are provided.

In some instances, a method of making the antibody or antigen-binding fragment as described herein comprises (a) culturing the cell as described herein; and (b) isolating the antibody or antigen-binding fragment thereof.

In some instances, a diagnostic reagent or a kit comprising the antibody or antigen-binding fragment described herein is provided.

In some instances, a method for decreasing IL-21-induced phosphorylation of STAT3 in an IL-21R-expressing cell, includes contacting the cell with the binding molecule or antigen-binding fragment thereof as described herein, the antibody or antigen-binding fragment thereof as described herein or the composition as described herein.

In some instances, a method for decreasing IL-21-mediated IFN γ production by an NK cell, includes contacting the NK cell with the binding molecule or antigen-binding fragment thereof as described herein, the antibody or antigen-binding fragment thereof as described herein or the composition as described herein.

In some instances, a method for decreasing IL-21-mediated differentiation of naïve or memory B cells into plasma cells, includes contacting naïve or memory B cells with the binding molecule or antigen-binding fragment thereof as described herein, the antibody or antigen-binding fragment thereof as described herein or the composition as described herein.

In some instances, the plasma cell differentiation is activated by CD4+ T cells.

In some instances, a method of treating an inflammatory, immune-mediated, or autoimmune disease or disorder in a subject, includes administering to a subject in need of treatment an effective amount of the binding molecule or antigen-binding fragment thereof as described herein, the antibody or antigen-binding fragment thereof as described herein or the composition as described herein.

In some instances, a method of preventing an inflammatory, immune-mediated, or autoimmune disease or disorder in a subject, includes administering to a subject susceptible to such disease or disorder an effective amount of the binding molecule or antigen-binding fragment thereof as described herein, the antibody or antigen-binding fragment thereof as described herein or the composition as described herein.

In some instances, the autoimmune disease is Sjögren's syndrome (SS), vasculitis (ANCA/GCA), systemic lupus erythematosis or lupus nephritis, rheumatoid arthritis (RA) Crohn's disease, myasthenia gravis, or any combination thereof.

In some instances, the immune-mediated disease or disorder is GVHD.

In some instances, the method of preventing GVHD includes reducing or eliminating the symptoms of GVHD.

In some instance, the symptoms of GVHD reduced or eliminated are rashes, blisters, nausea, loss of appetite, vomiting, early fullness after eating, diarrhea, abdominal discomfort, abdominal bloating, blood in the stool, jaundice, dark urine, upper abdominal discomfort, water weight gain (or swelling), arthritis-like symptoms, pain and stiffness, dry eyes, eye irritation, mouth sores, persistent cough, shortness of breath, difficulty breathing.

In some instances, a method for inhibiting weight loss due to GVHD, includes administering to a subject having GVHD or susceptible to GVHD, the binding molecule or antigen-binding fragment thereof as described herein, the antibody or antigen-binding fragment thereof as described herein or the composition as described herein.

In some instances, a method for reducing anemia due to GVHD, includes administering to a subject having GVHD or susceptible to GVHD, the binding molecule or antigen-binding fragment thereof as described herein, the antibody or antigen-binding fragment thereof as described herein or the composition as described herein.

In some instances, a method for inhibiting expansion of T cells, includes administering to a subject having GVHD or susceptible to GVHD, the binding molecule or antigen-binding fragment thereof as described herein, the antibody or antigen-binding fragment thereof as described herein or the composition as described herein.

In some instances, a method for reducing cytokines in a subject having GVHD or susceptible to GVHD, includes administering to the subject the binding molecule or antigen-binding fragment thereof as described herein, the antibody or antigen-binding fragment thereof as described herein or the composition as described herein.

In some instances, a method for detecting IL-21 expression levels in a sample includes (a) contacting said sample with the binding molecule or antigen-binding fragment thereof of as described herein, the antibody or antigen-binding fragment thereof as described herein or the composition as described herein and (b) detecting binding to IL-21 in said sample.

BRIEF DESCRIPTION OF THE DRAWINGS/FIGURES

FIG. 1A shows alignments of the variable regions of murine monoclonal antibody 9F11 (VH: SEQ ID NO:28, VL: SEQ ID NO:33) and three humanized variants (VH-4 and VH-11: SEQ ID NO:37, VH-6: SEQ ID NO:38, VL-4 and VL-6: SEQ ID NO:39, VL-11: SEQ ID NO:40). Residues that are different between human and murine in the framework regions are double underlined. The murine back mutations in the framework regions are bolded, and the CDR regions are underlined. FIG. 1B shows alignments of the variable regions of murine monoclonal antibody 19E3 (VH: SEQ ID NO:6, VL: SEQ ID NO:11) and three humanized VH variants (SEQ ID Nos 61, 62, and 63) and two humanized VL variants (SEQ ID NOs: 64 and 65). Residues that are different between human and murine in the framework regions are double underlined. The murine back mutations in the framework regions are bolded, and the CDR regions are underlined.

FIG. 2A and FIG. 2B show KinExA Dual Curve Fit of 500 fM and 50 pM concentrations of K44VHa-N56Q (MEDI7169) IgG in solution phase competition with human (FIG. 2A) and cynomolgus monkey (FIG. 2B) IL-21.

FIG. 3A shows the effect of human or cynomolgus monkey IL-21 on STAT3 phosphorylation of human PBMCs. FIG. 3B shows inhibition of human and cynomolgus monkey IL-21-induced upregulation of STAT3 phosphorylation of human PBMCs by anti-IL-21 antibodies K2Ha-N56Q (inverted triangles), K44VHa-N56Q (MEDI7169) (diamonds), and K44VHa6-N56Q (circles).

Figure 5A:
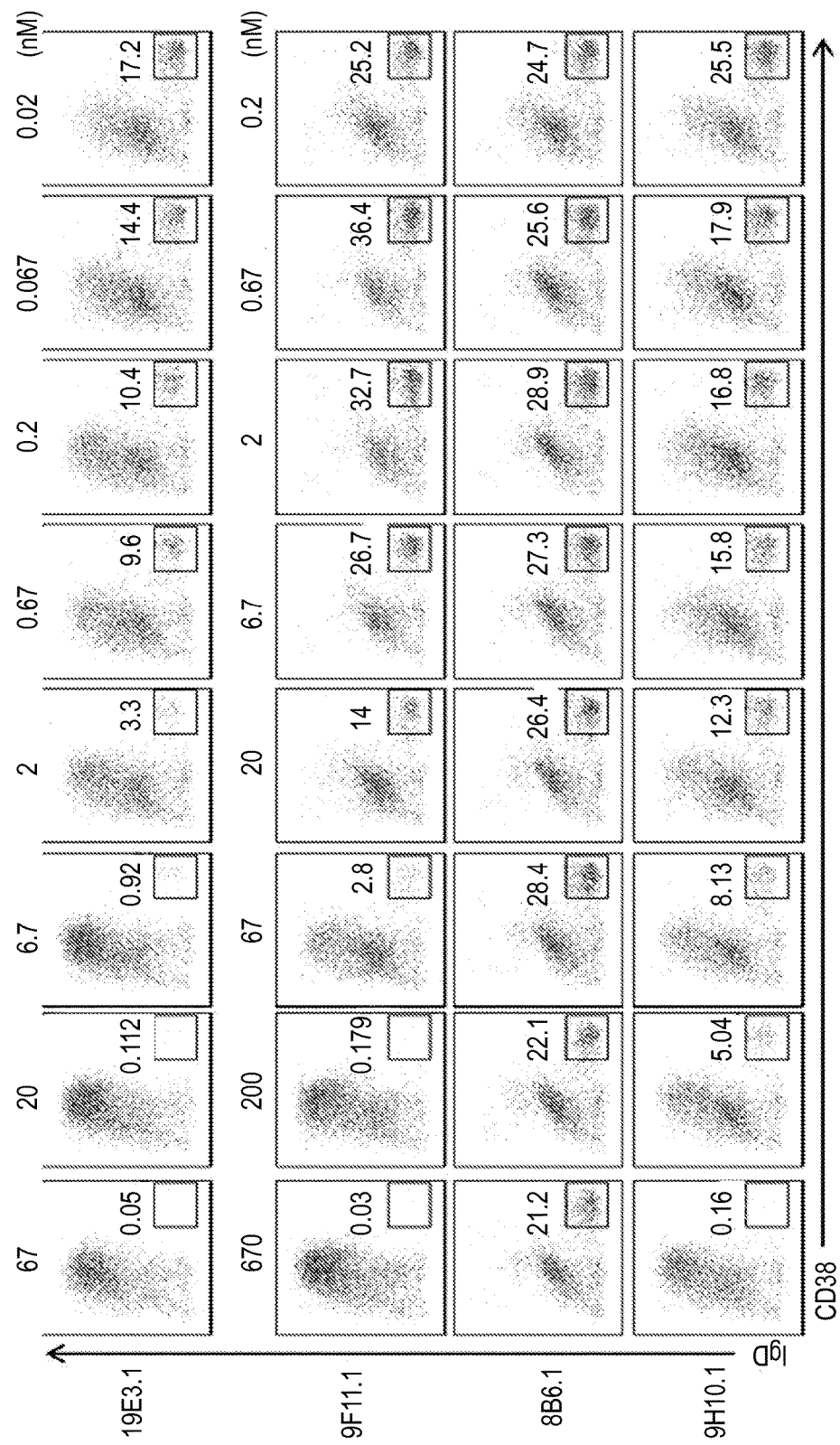
Figure 5B:
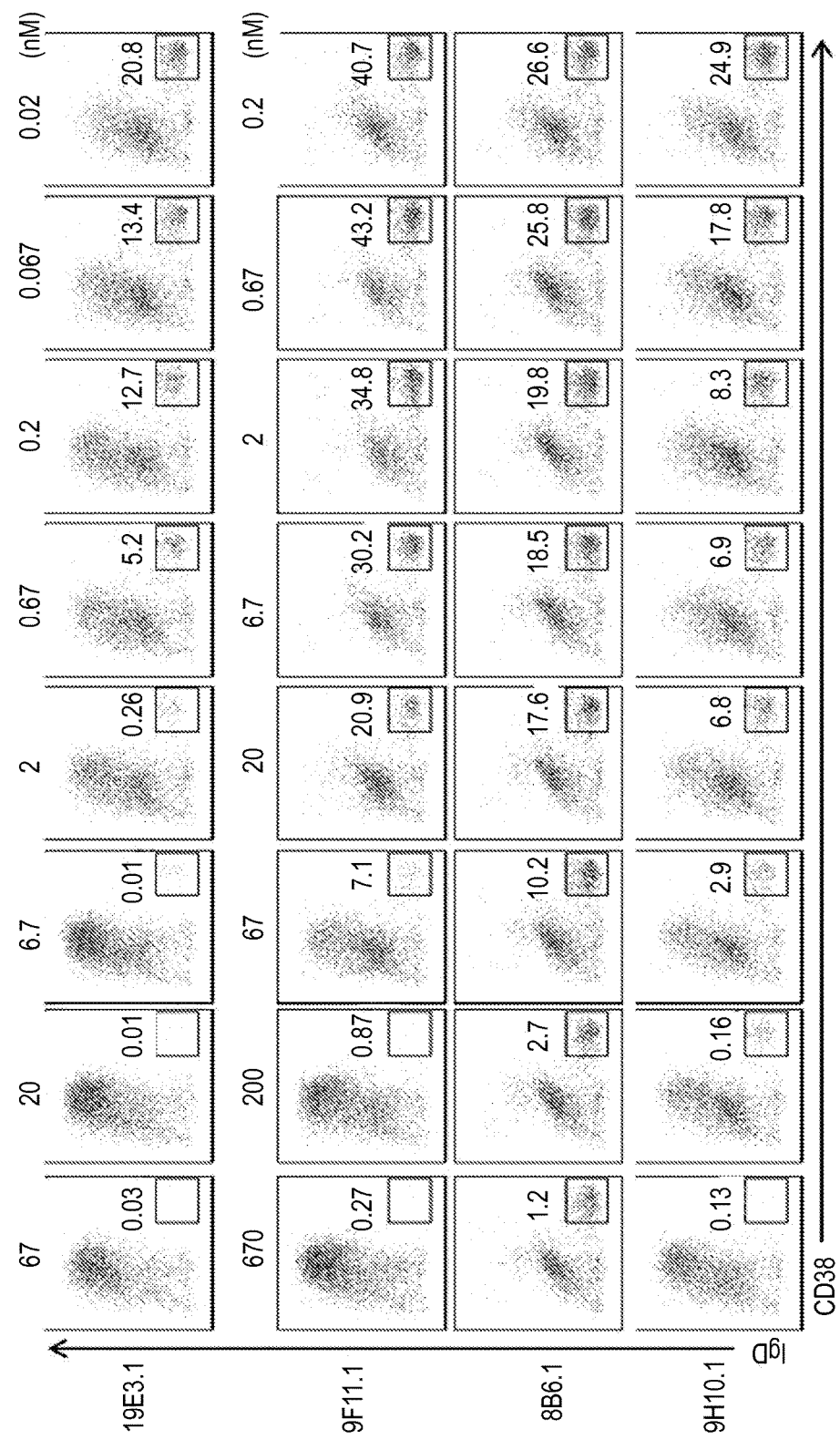
Figure 5C:
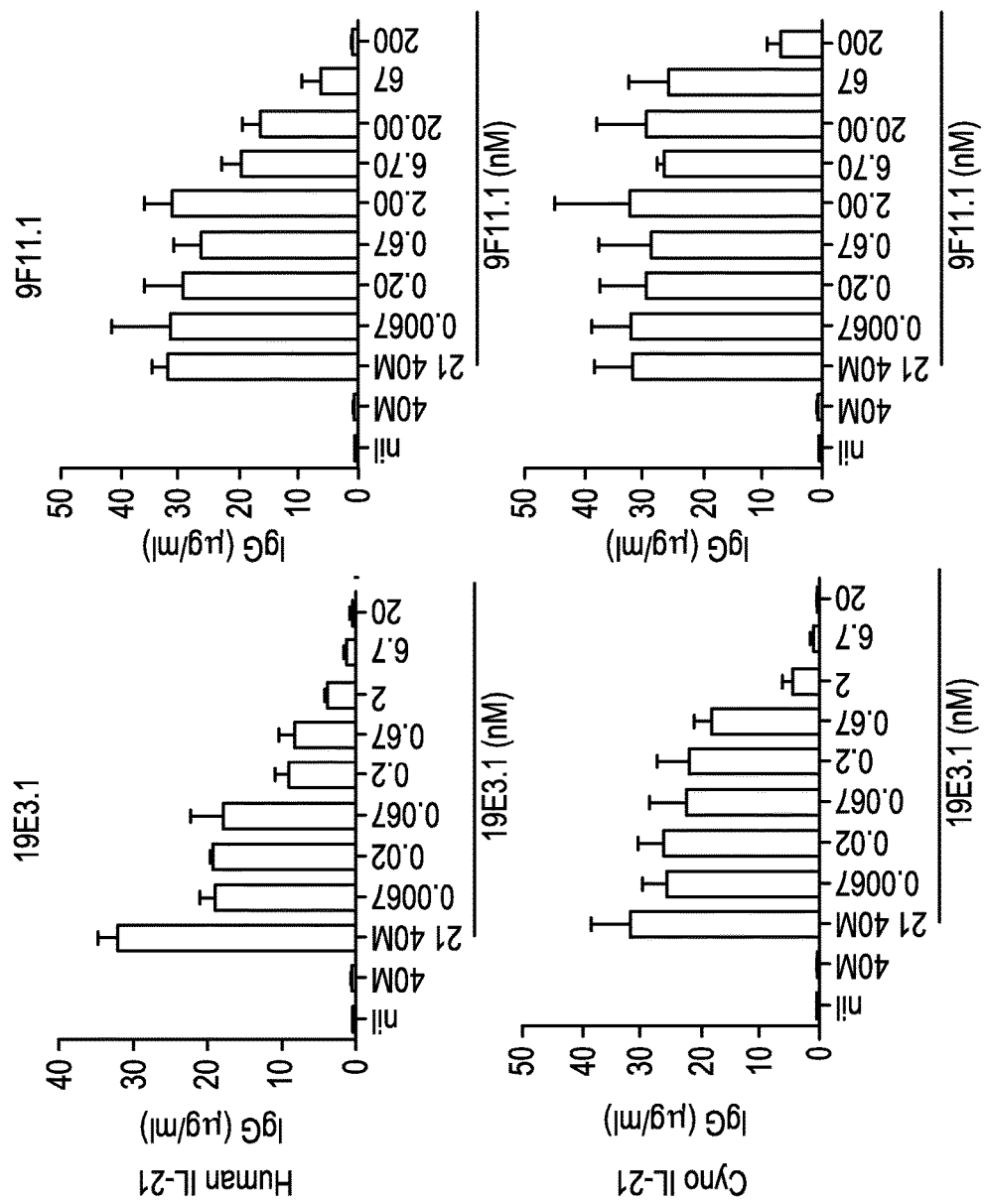

FIG. 5 shows the inhibition of IL-21-induced differentiation of human B cells into plasma cells by either human (FIG. 5A) or cynomologous monkey (FIG. 5B) IL-21. The graphs show reduction in the level of IgD$^-$ CD38$^{hi}$ PCs as compared to controls. FIG. 5C shows that under control conditions, stimulation with IL-21, anti-CD40 and anti-IgM resulted in Ig production in the range of 30-40 µg/ml by day 6, and 19E3.1 and 9F11.1 inhibited Ig production.

Figure 6B:
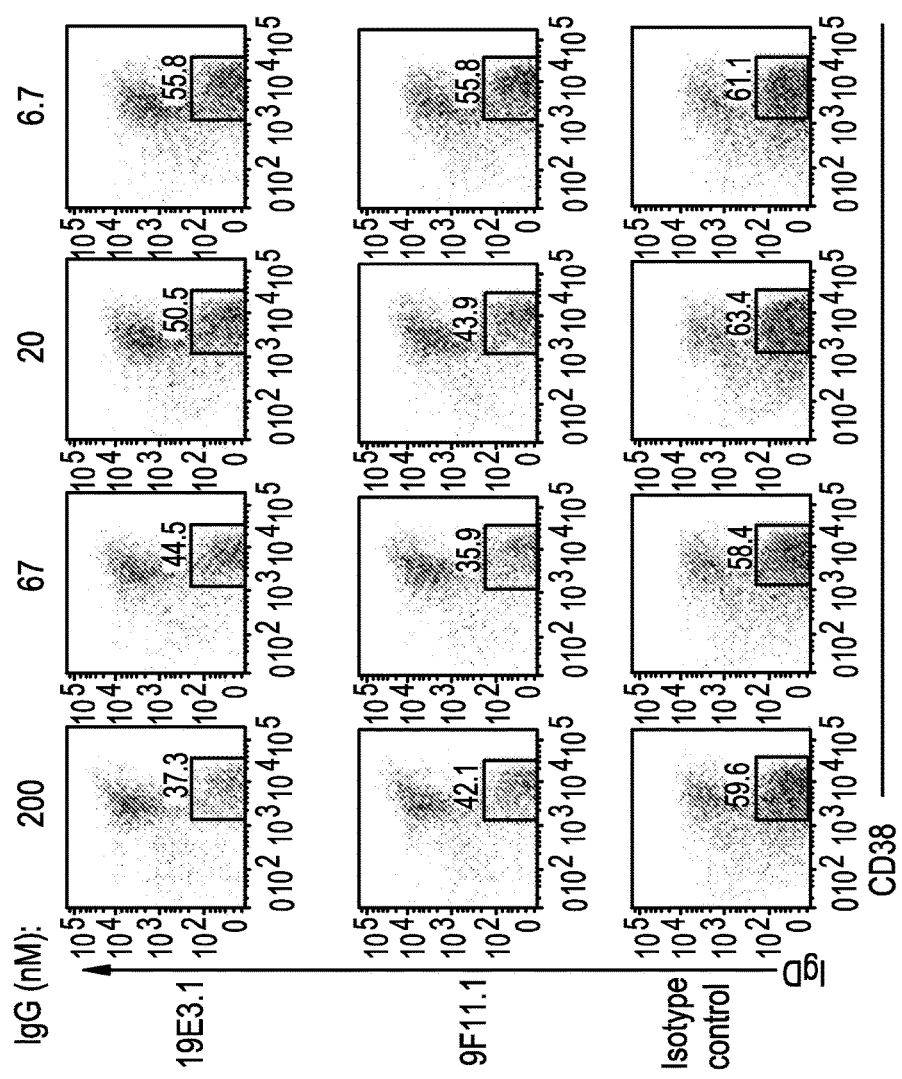

FIG. 6A shows that co-culture of B cells with activated CD4+ T cells resulted in the emergence of an IgD$^-$ CD38$^{hi}$ PC population, with 68.5% of the CD19+ cells expressing this PC phenotype by day 7. FIGS. 6B and 6C show inhibition of PC differentiation by the addition of 19E3.1 or 9F11.1.

Figure 7:
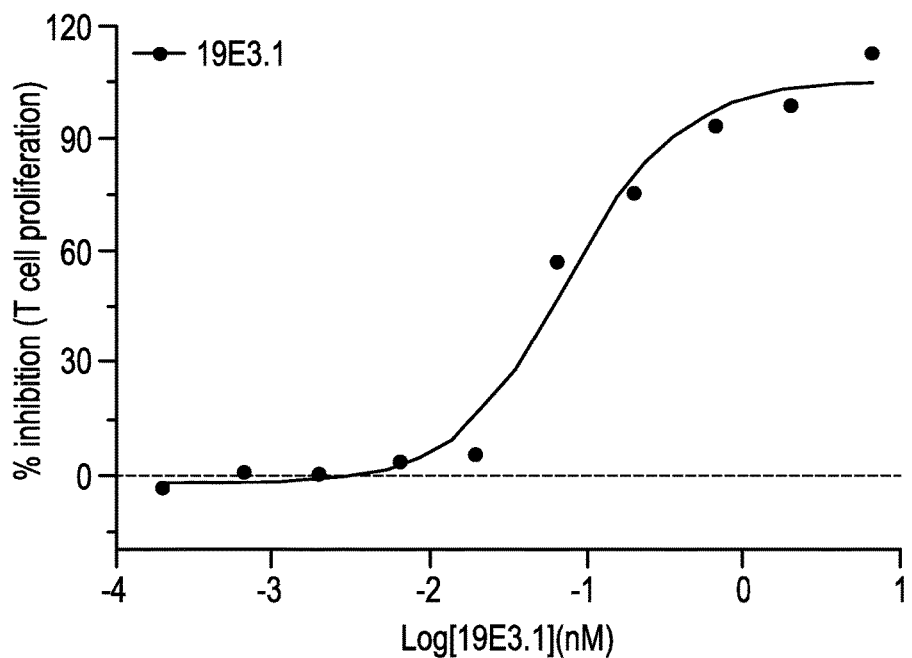

FIG. 7 shows that anti-IL21 antibody (19E3.1) blocks IL-21 induced T Cell expansion. Human T cells were stimulated with recombinant human IL-21 in combination with anti-CD3. Antibody 19E3.1 was added at the indicated concentrations and T-cell expansion was quantified on day four. All conditions were run in duplicate. The experiment was performed with two unique donors. One representative donor is shown.

FIG. 8 shows that K44VHa-N56Q (MEDI7169) blocks GVHD-induced wasting disease by limiting CD4+ T-cell expansion. Donor 1 PBMCs ($12.71 \times 10^6$) or Donor 2 PBMCs ($13.46 \times 10^6$) were transferred into NOD/SCID/γc mice on study Day 0. Mice received 200 μg of either Control mAb (FIG. 8A) or K44VHa-N56Q (FIG. 8B) given three times a week starting at Day −1. Mice were bled every other week and assessed by flow cytometry to determine the number, and phenotype of human CD45+ cells. FIG. 8C and FIG. 8D show the percentage of human CD45+ cells collected from mice receiving the Control mAB or K44VHa-N56Q, respectively, (from Day 21, Donor 1; n=3 Control mAb, n=5 K44VHa-N56Q). FIG. 8E and FIG. 8F show the percentage of CD4+ or CD8+ cells within the human CD45+ fraction in mice receiving the Control mAB or K44VHa-N56Q, respectively, (from Day 35, Donor 2; n=10 Control mAb+PBS vehicle/n=5 K44VHa-N56Q). All conditions stained 100 μL of blood and were collected on a flow cytometer for the same length of time, thus the number of events displayed is reflective of relative cell number. Average ±standard error of absolute numbers of human CD45+ cells collected from blood on Day 21 were for Donor 1, Control mAb, n=3 (729,111±113,899) versus K44VHa-N56Q, n=5 (39,104±5,159), P<0.0357. For Donor 2, Control mAb and PBS combined, n=10 (237,294±35,628) versus K44VHa-N56Q, n=5, (14,980±2,275) P=0.0007.

Figure 9:
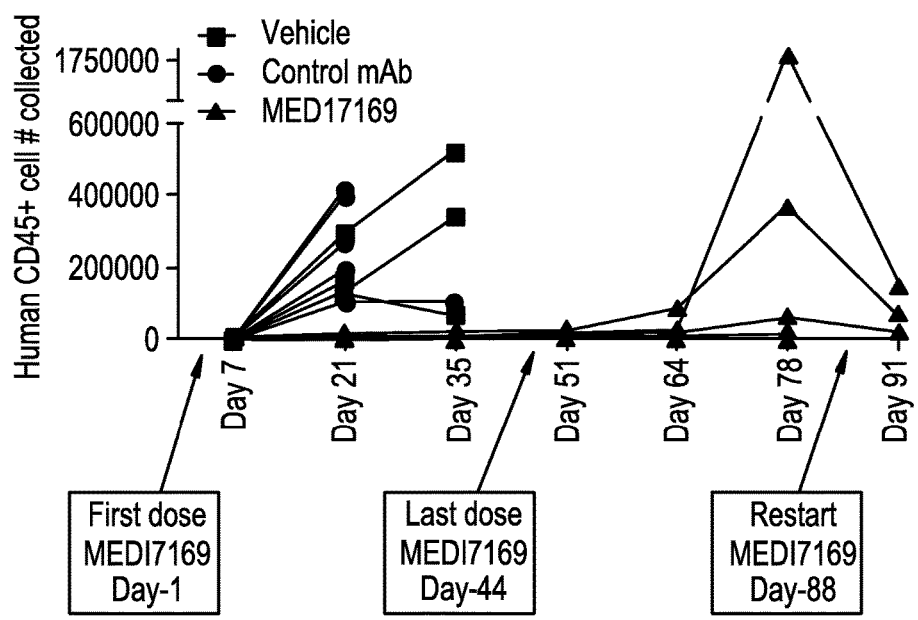

FIG. 9 shows that K44VHa-N56Q reversibly inhibits human cell expansion in recipient mice. Donor 2 PBMCs ($13.46 \times 10^6$) were transferred into NOD/SCID/γc mice on study Day 0. Mice received 200 μL of PBS vehicle (squares), or 200 μg of either K44VHa-N56Q (triangles) or Control mAb (circles) given three times a week starting at Day −1 until Day 44. Mice were bled every other week, and assessed by flow cytometry to determine the number of human CD45+ cells. Data indicates number of human cells collected. All conditions stained 100 μL of blood and the same volume was collected on a flow cytometer, thus the number of events displayed is reflective of relative cell number.

Figure 10A:
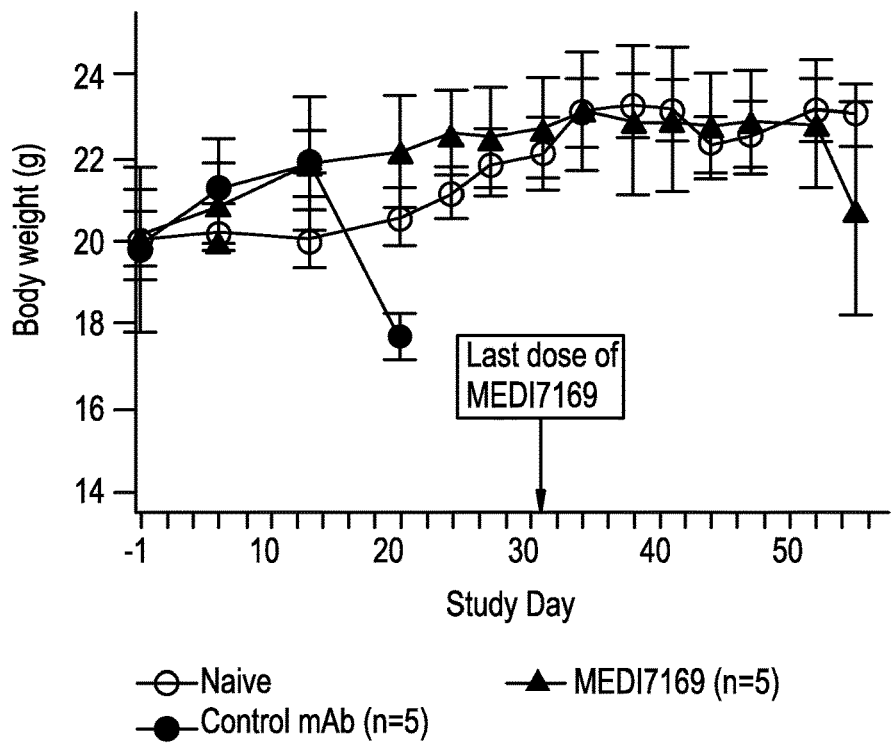
Figure 10B:
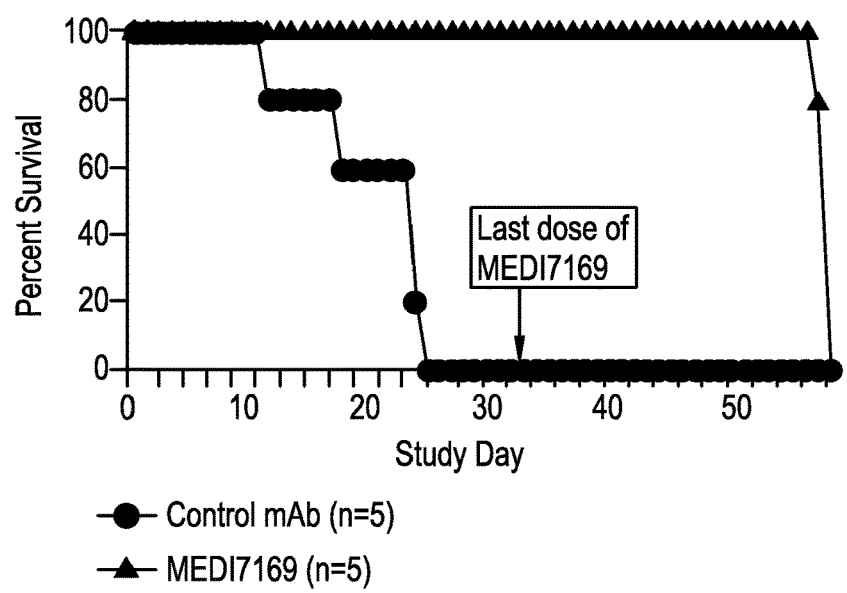

FIG. 10 shows that K44VHa-N56Q protects from GVHD-induced weight loss and death. Donor 1 PBMCs ($12.71 \times 10^6$) were transferred into NOD/SCID/γc mice on study Day 0 and mice were followed for body weight loss (FIG. 10A) and death (FIG. 10B). Either K44VHa-N56Q (triangles) or Control mAb (filled circles) was given three times a week at 200 μg/mouse starting at Day −1 until Day 31. Naive (open circles) animals received no human cells and no mAb. Percent survival represents when either the mice died or reached 20% body weight loss and were sacrificed. One of two independent experiments from two different Donor PBMCs is shown.

FIG. 11 shows inhibition of cell proliferation and cytokine production by K44VHa-N56Q. Donor 2 PBMCs ($13.46 \times 10^6$) were transferred into NOD/SCID/γc mice on study Day 0 and injected with either 200 μg of K44VHa-N56Q or Control mAb three times a week starting on Day −1. Mice were bled and the amount of cytokine in sera was evaluated for the presence of cytokines using the Millipore's MILLIPLEX MAP system human Th17 kit. Serum levels (pg/mL) are shown for IL-21 (FIG. 11A), interferon gamma (FIG. 11B), tumor necrosis factor alpha (FIG. 11C), IL-9 (FIG. 11D), granulocyte macrophage colony-stimulating factor (FIG. 11E), IL-10 (FIG. 11F), and IL-5 (FIG. 11G).

FIG. 12 shows that inhibition of cell proliferation and cytokine production by anti-IL-21 is reversible. Donor 1 PBMCs ($12.71 \times 10^6$) were transferred into NOD/SCID/γc mice a on Day 0 and injected with either 200 μg of K44VHa-N56Q (closed symbols) or Control mAb (open symbols) three times a week starting on Day −1 until Day 31, when the K44VHa-N56Q was stopped. Mice were bled on Days 15, 28, 43, and 57, and the amount of interferon gamma (FIG. 12A), tumor necrosis factor alpha (FIG. 12B), and IL-10 (FIG. 12C) in sera at these times points was determined using the Millipore's MILLIPLEX MAP system human Th17 kit. Mice were also bled on Days 7, 21, 35, 51, and 57, and the numbers of human CD45+ cells were determined (FIG. 12D). All mice that received control mAb died by study Day 28; thus, there is only one time point for cytokines for these animals.

Figure 13:
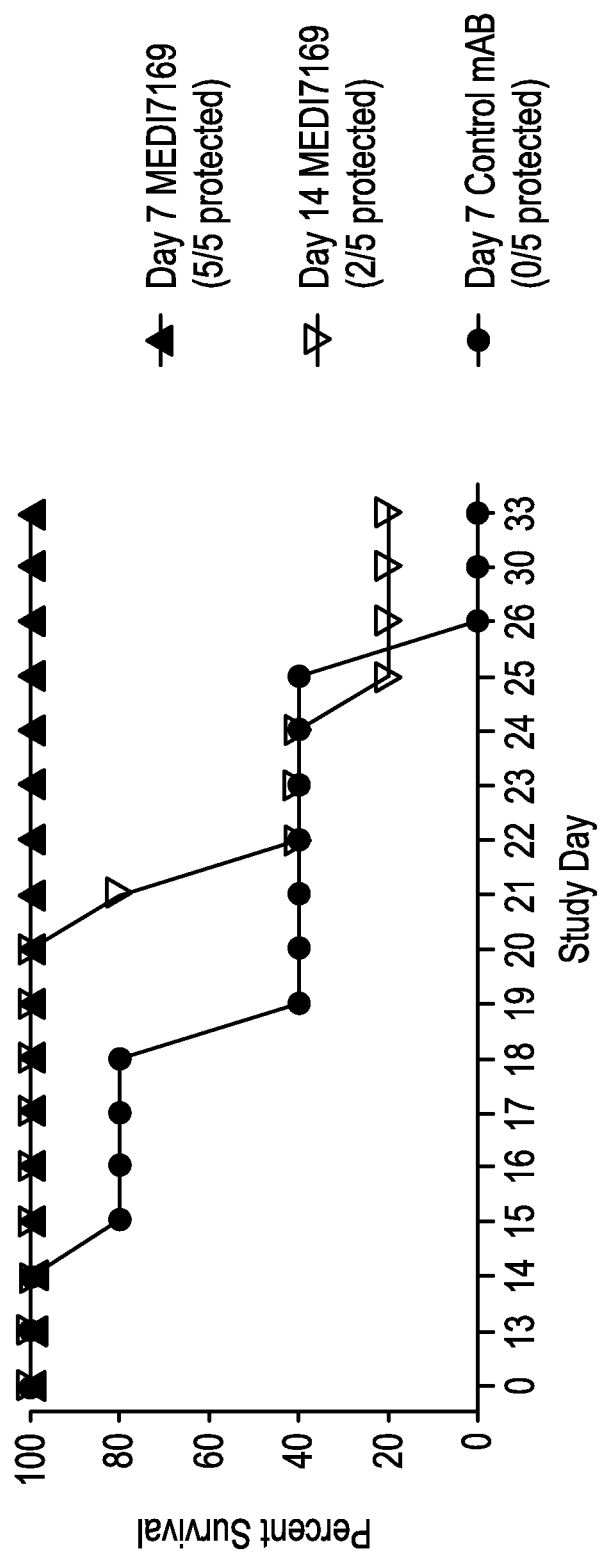
Figure 14A:
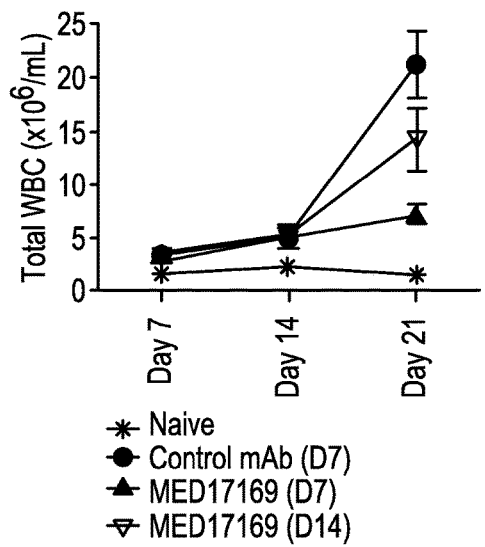
Figure 14B:
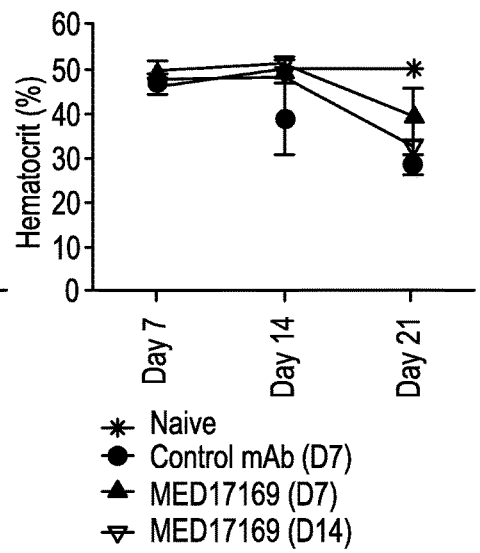
Figure 14C:
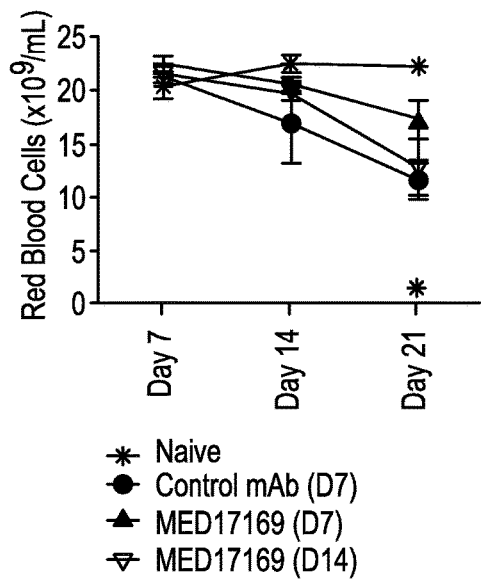
Figure 14D:
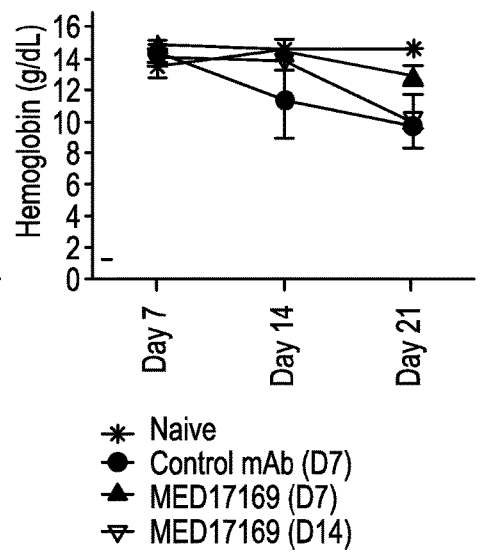

FIG. 13 shows that therapeutic K44VHa-N56Q protects subjects from GVHD. Donor 1 PBMCs ($12.0 \times 10^6$) were transferred into NOD/SCID/γc mice on study Day 0 and survival was monitored. Either Control mAb starting on study Day 7 (circles), K44VHa-N56Q starting on study Day 7 (triangles), or K44VHa-N56Q starting on study Day 14 (inverse triangles), were given three times a week at 200 μg/mouse. Mice were euthanized when they were determined to have lost 20% body weight or if the mouse was emaciated/moribund or otherwise in pain or distress. Death and humane euthanasia were used synonymously for the purposes of tracking survival.

FIG. 14 shows that K44VHa-N56Q can protect from GVHD-induced anemia. Mice were injected and treated as described for FIG. 13. Mice were naïve, i.e., given no cells (asterisks), or given human PBMC's followed by Control mAb starting on study Day 7 (circles), K44VHa-N56Q starting on study Day 7 (triangles), or K44VHa-N56Q starting on study Day 14 (inverse triangles), given three times a week at 200 μg/mouse. Heparinized whole blood samples collected from retro-orbital sinus were diluted 1:10 prior to analysis with an automated hematology analyzer (Sysmex XT-2000iv). The resulting total white blood cell (FIG. 14A) and red blood cell counts (FIG. 14C), hematocrit (FIG. 14B), and hemoglobin (FIG. 14D) values were multiplied by a dilution factor of ten.

DETAILED DESCRIPTION OF THE INVENTION

The present invention provides molecules and antigen-binding fragments thereof that bind to IL-21. In some embodiments, such molecules are antibodies and antigen-binding fragments thereof that specifically bind to IL-21. Related polynucleotides, compositions comprising the anti-IL-21 antibodies or antigen-binding fragments thereof, and methods of making the anti-IL-21 antibodies and antigen-binding fragments are also provided. Methods of using the novel anti-IL-21 antibodies, such as methods of treating inflammatory, immune-mediated, or autoimmune disease or disorders in a subject and diagnostic uses, are further provided.

In order that the present invention can be more readily understood, certain terms are first defined. Additional definitions are set forth throughout the detailed description.

I. Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" is to be taken as specific disclosure of each of the two specified features or components with or without the other. Thus, the term and/or" as used in a phrase such as "A and/or B" is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

The term "IL-21" refers to the cytokine interleukin-21, and/or active fragments thereof. IL-21 binds to the IL-21 receptor on various different cells of the immune system, inducing signal transduction in those cells as described elsewhere herein. IL-21 has been characterized in most common animal model systems. The cDNA and amino acid sequences of human IL-21 can be found, e.g., at GenBank Accession Numbers BC066260.1 (SEQ ID NO:1) and AAH69124.1 (SEQ ID NO:2). The cDNA and amino acid sequences of cynomolgus monkey (*Macaca fascicularis*) IL-21 can be found, e.g., as SEQ ID NOs: 3 (SEQ ID NO:3) and 4 (SEQ ID NO:4) of US Patent Application Publication No. 2008-0267910 A1 (incorporated herein by reference in its entirety).

The terms "inhibit," "block," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect on the IL-21 signal transduction pathway, e.g., on signal transduction in a cell expressing the IL-21 receptor (IL-21R) in the presence of IL-21, (e.g., phosphorylation of STAT3, production of interferon-gamma IFN-γ in NK cells, B cell differentiation into plasma cells or inhibition of IL-21-driven proliferation of human naive CD4+ T-cells), the terms refer to the ability of an IL-21 binding molecule, e.g., an anti-IL-21 antibody or antigen-binding fragment thereof, to statistically significantly decrease the IL-21-induced signal transduction through IL-21R relative to the signal transduction in an untreated (control) cell. The cell which expresses IL-21R can be a naturally occurring cell or cell line (e.g., a T cell, a B cell, a natural killer (NK) cell, a dendritic cell or another type of lymphoid cell) or can be recombinantly produced by introducing a nucleic acid encoding IL-21R into a host cell. In one embodiment, the IL-21 binding molecule, e.g., an anti-IL-21 antibody or antigen-binding fragment thereof can inhibit IL-21-mediated signal transduction in an IL-21R-expressing cell by at least 10%, or at least 20%, or at least 30%, or at least 40%, or at least 50%, or at least 60%, or at least 70%, or at least 80%, or at least 90% or about 100%, as determined, for example, by flow cytometry, Western blotting, ELISA, or other assays as described in the Examples below.

The terms "antibody" or "immunoglobulin," as used interchangeably herein, include whole antibodies and any antigen-binding fragment or single chains thereof.

A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, C1. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include the hybridoma-produced murine monoclonal antibodies 19E3, 9F11, 8H10, and 8B6, humanized, affinity optimized, germlined and/or other versions of these antibodies, and serum half-life-optimized anti-IL-21 YTE antibodies (e.g., K44VHa-N56Q K44VHa6-N56Q, or K2Ha-N56Q).

The term "germlining" means that amino acids at specific positions in an antibody are mutated back to those in the germ line.

The term "antibody" can refer to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

A "blocking" antibody or an "antagonist" antibody is one that inhibits or reduces biological activity of the antigen it binds, such as IL-21. In certain aspects, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "IL-21 antibody" or "an antibody that binds to IL-21" or "anti-IL-21" refers to an antibody that is capable of binding IL-21 with sufficient affinity such that the antibody is useful as a therapeutic agent or diagnostic reagent in targeting IL-21. The extent of binding of an anti-IL-21 antibody to an unrelated, non-IL-21 protein is less than about 10% of the binding of the antibody to IL-21 as measured, e.g., by a radioimmunoassay (RIA), BIACORE® (using recombinant IL-21 as the analyte and antibody as the ligand, or vice versa), KINEXA®, or other binding assays known in the art. In certain embodiments, an antibody that binds to IL-21 has a dissociation constant ($K_D$) of ≤1 μM, ≤100 nM, ≤10 nM, ≤1 nM, ≤0.1 nM, ≤10 pM, ≤1 pM, or ≤0.1 pM.

The term "antigen-binding fragment" refers to a portion of an intact antibody and refers to the complementarity determining variable regions of an intact antibody. Fragments of a full-length antibody can be an antigen-binding fragment of an antibody. Examples of antibody fragments include, but are not limited to Fab, Fab', F(ab')2, and Fv fragments, linear antibodies, single chain antibodies (e.g., ScFvs), and multispecific antibodies formed from antibody fragments.

A "monoclonal antibody" (mAb) refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 ... 34 |
| | | | (Kabat Numbering) |
| H1 | H31-H35 | H26-H35 | H26-H32 |
| | | | (Chothia Numbering) |
| H2 | H50-H65 | H50-H58 | H52-H55 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. See Table 1.

IMGT (ImMunoGeneTics) also provides a numbering system for the immunoglobulin variable regions, including the CDRs. See e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., J. Biol. Chem. 281:23514-24 (2006); Robbie et al., (2013) Antimicrob. Agents Chemother. 57, 6147-6153). See also U.S. Pat. No. 7,083,784, which is hereby incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Potency" is normally expressed as an $IC_{50}$ value, in nM or pM unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art.

The fold improvement in potency for the antibodies or polypeptides of the invention as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition that is "isolated" is a polypeptide, antibody, polynucleotide, vector, cell, or composition that is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition that is isolated is substantially pure.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

The word "label" when used herein refers to a detectable compound or composition that is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition that is detectable.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for an inflammatory, immune-mediated, or autoimmune disease or disorder according to the methods provided herein if the patient shows, e.g., total, partial, or transient alleviation or elimination of symptoms associated with the disease or disorder.

"Prevent" or "prevention" refer to prophylactic or preventative measures that prevent and/or slow the development of a targeted pathologic condition or disorder. Thus, those in need of prevention include those prone to have or susceptible to the disorder. In certain embodiments, an inflammatory, immune-mediated, or autoimmune disease or disorder is successfully prevented according to the methods provided herein if the patient develops, e.g., transiently or permanently, fewer or less severe symptoms associated with the disease or disorder, or a later onset of symptoms associated with the disease or disorder, than a patient who has not been subject to the methods of the invention.

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and non-amino acids can interrupt it. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the IL-21 to which the polypeptide or antibody binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94:412-417 (1997)).

II. Anti-IL-21-Binding Molecules

The present invention provides IL-21 binding molecules, e.g., anti-IL-21 antibodies and antigen-binding fragments thereof that specifically bind IL-21. The full-length amino acid (aa) and nucleotide (nt) sequences for IL-21 are known in the art. See, e.g., GenBank Accession Nos. BC066260.1 (SEQ ID NO:1) and AAH69124.1 (SEQ ID NO:2), respectively, for human IL-21, or US Patent Application Publication No. 2008-0267910 A1 for cynomolgus monkey (*Macaca fasciculari*) IL-21 (SEQ ID NOs: 3 and 4, respectively). In some embodiments, IL-21 binding molecules, e.g., anti-IL-21 antibodies or antigen-binding fragments thereof provided herein are murine antibodies, humanized antibodies or human antibodies. In certain embodiments, the IL-21 binding molecules are antibodies or antigen-binding fragments thereof. In some embodiments, IL-21 binding molecules, e.g., anti-IL-21 antibodies or antigen-binding fragments thereof comprise a Fab, a Fab', a F(ab')$_2$, a Fd, a single chain Fv or scFv, a disulfide linked Fv, a V-NAR domain, an IgNar, an intrabody, an IgGΔCH2, a minibody, a F(ab')$_3$, a tetrabody, a triabody, a diabody, a single-domain antibody, DVD-Ig, Fcab, mAb$^2$, a (scFv)$_2$, or a scFv-Fc. In some embodiments, the antibody is of the IgG1 subtype and comprises the triple mutant YTE, as disclosed supra in the Definitions section. Certain anti-IL-21 antibodies or fragments thereof are provided in Table 2 in the examples section.

In certain aspects, this disclosure provides an IL-21 binding molecule or antigen-binding fragment thereof, e.g., an anti-IL-21 antibody or antigen-binding fragment thereof, which can specifically bind to the same IL-21 epitope as an antibody or antigen-binding fragment thereof comprising the heavy chain variable region (VH) and light chain variable region (VL) of 19E3, 9F11, 8B6, or 9H10. Also provide is an IL-21 binding molecule or antigen-binding fragment thereof, e.g., an anti-IL-21 antibody or antigen-binding fragment thereof, which can competitively inhibit, or can bind to IL-21 with a greater affinity than an antibody or antigen-binding fragment thereof comprising the VH and VL of 19E3, 9F11, 8B6, or 9H10. As provided herein, the VH and VL of 19E3 comprise SEQ ID NOs: 6 and 11, respectively, the VH and VL of 9F11 comprise SEQ ID NOs: 28 and 33, respectively, the VH and VL of 8B6 comprise SEQ ID NOs: 42 and 47, respectively, and the VH and VL of 9H10 comprise SEQ ID NOs: 52 and 57, respectively.

The disclosure further provides an IL-21 binding molecule or antigen-binding fragment, e.g., an anti-IL-21 antibody or antigen-binding fragment thereof, including an antibody VL region. In certain aspects the VL region includes one, two, or three VL-CDRs such as a VLCDR1 identical to, or identical except for eight, seven, six, five, four, three, two, or one amino acid substitutions to SEQ ID NO: 12, SEQ ID NO: 34, SEQ ID NO: 48, or SEQ ID NO: 58, a VLCDR2 identical to or identical except for eight, seven, six, five, four, three, two, or one amino acid substitutions to SEQ ID NO: 13, SEQ ID NO: 35, SEQ ID NO: 49, or SEQ ID NO: 59, or a VLCDR3 identical to or identical except for eight, seven, six, five, four, three, two, or one amino acid substitutions to SEQ ID NO: 14, SEQ ID NO: 36, SEQ ID NO: 50, or SEQ ID NO: 60. In certain aspects the VL region contains VL-CDR1, VL-CDR2, and VL-CDR3 amino acid sequences identical to, or identical except for eight, seven, six, five, four, three, two, or one amino acid substitutions in one or more of the VL-CDRS to: SEQ ID NOs: 12, 13, and 14, SEQ ID NOs: 34, 35, and 36, SEQ ID NOs: 48, 49, and 50, or SEQ ID NOs: 58, 59, and 60, respectively. In certain aspects, the VL region comprises an amino acid sequence at least 70%, 75%, 80%, 85%, 90%, 95%, or 100% identical to the reference amino acid sequence SEQ ID NO: 11, SEQ ID NO: 17, SEQ ID NO: 21, SEQ ID NO: 25, SEQ ID NO: 33, SEQ ID NO: 39, SEQ ID NO: 40, SEQ ID NO: 47, or SEQ ID NO: 57.

Further provided is a binding molecule or antigen-binding fragment thereof that specifically binds to IL-21, e.g., an anti-IL-21 antibody or antigen-binding fragment thereof including an antibody VH region. In certain aspects the VH region includes one, two, or three VH-CDRs such as a VHCDR1 identical to, or identical except for eight, seven, six, five, four, three, two, or one amino acid substitutions to SEQ ID NO: 7, SEQ ID NO: 29, SEQ ID NO: 43, or SEQ ID NO: 53, a VHCDR2 identical to or identical except for eight, seven, six, five, four, three, two, or one amino acid substitutions to SEQ ID NO: 8, SEQ ID NO: 30, SEQ ID NO: 44, or SEQ ID NO: 54, or a VHCDR3 identical to or identical except for eight, seven, six, five, four, three, two, or one amino acid substitutions to SEQ ID NO: 9, SEQ ID NO: 31, SEQ ID NO: 45, or SEQ ID NO: 55. In certain aspects the VH region contains VH-CDR1, VH-CDR2, and VH-CDR3 amino acid sequences identical to, or identical except for eight, seven, six, five, four, three, two, or one amino acid substitutions in one or more of the VH-CDRS to: SEQ ID NOs: 7, 8, and 9, SEQ ID NOs: 29, 30 and 31, SEQ ID NOs: 43, 44, and 45, or SEQ ID NOs: 53, 54, and 55, respectively. In certain aspects, the VH region comprises an amino acid sequence at least 70%, 75%, 80%, 85%, 90%, 95%, or 100% identical to the reference amino acid sequence SEQ ID NO: 6, SEQ ID NO: 15, SEQ ID NO: 19, SEQ ID NO: 23, SEQ ID NO: 28, SEQ ID NO: 37, SEQ ID NO: 38, SEQ ID NO: 42 or SEQ ID NO: 52.

In particular aspects, an IL-21 binding molecule provided herein comprises an anti-IL-21 antibody or antigen-binding fragment thereof. For example, the disclosure provides an isolated antibody or antigen-binding fragment thereof which specifically binds to IL-21 comprising a VL region and a VH region, where the VL and VH collectively contain VL-CDR1, VL-CRD2, VL-CDR3, VH-CDR1, VH-CDR2, and VH-CDR3 amino acid sequences identical or identical except for eight, seven, six, five, four, three, two, or one amino acid substitutions in one or more CDRs to: SEQ ID NOs: 12, 13, 14, 7, 8, and 9, SEQ ID NOs: 34, 35, 36, 29, 30, and 31, SEQ ID NOs: 48, 49, 50, 43, 44, and 45, or SEQ ID NOs: 58, 59, 60, 53, 54, and 55, respectively.

For example, the disclosure provides an isolated antibody or antigen-binding fragment thereof which specifically binds to IL-21 comprising a VH and a VL, where the VH and VL contain, respectively, amino acid sequences at least 70%, 75%, 80%, 85%, 90%, 95%, or 100% identical to reference amino acid sequences SEQ ID NO: 6 and SEQ ID NO: 11, SEQ ID NO: 15 and SEQ ID NO: 17, SEQ ID NO: 19 and SEQ ID NO: 21, SEQ ID NO: 23 and SEQ ID NO: 25, SEQ ID NO: 28 and SEQ ID NO: 33, SEQ ID NO: 37 and SEQ ID NO: 39, SEQ ID NO: 38 and SEQ ID NO: 39, SEQ ID NO: 37 and 40, SEQ ID NO: 42 and SEQ ID NO: 47, or SEQ ID NO: 52 and SEQ ID NO: 57, respectively.

In one aspect, the disclosure provides an anti-IL-21 antibody or antigen-binding fragment thereof comprising the VH and VL of K44VHa-N56Q, VH amino acid sequence SEQ ID NO: 19 and the VL amino acid sequence SEQ ID NO: 21.

An anti-IL-21 antibody or antigen-binding fragment thereof provided herein, e.g., as described above can be, e.g., a murine antibody, a humanized antibody, a chimeric antibody, a monoclonal antibody, a polyclonal antibody, a recombinant antibody, a multispecific antibody, or any combination thereof. An anti-IL-21 antibody antigen-binding fragment can be an Fv fragment, an Fab fragment, an F(ab')2 fragment, an Fab' fragment, a dsFv fragment, an scFv fragment, or an sc(Fv)2 fragment.

In one aspect, the disclosure provides an anti-IL-21 antibody or antigen-binding fragment thereof that can bind to IL-21 molecules across species, e.g., the antibody or fragment can bind to mouse IL-21, rat IL-21, rabbit, IL-21, human IL-21 and/or cynomolgus monkey IL-21. For example, the antibody or fragment can bind to human IL-21 and cynomolgus monkey IL-21. In a further example, the antibody or fragment can also bind to mouse IL-21.

The IL-21 receptor shares a common gamma chain with a number of other cytokine receptors, e.g., IL-2R, IL-4R, IL-7R, IL-9R, and IL-15R. In certain embodiments provided herein, an anti-IL-21 antibody or antigen binding fragment thereof can specifically bind to IL-21, e.g., human IL-21 and cynomolgus monkey IL-21, and mouse IL-21 but does not specifically bind to human IL-2, IL-4, IL-7, IL-9, or IL-15.

An anti-IL-21 antibody or antigen-binding fragment thereof provided herein, e.g., as described above, can include, in addition to a VH and a VL, a heavy chain constant region or fragment thereof. In certain aspects the heavy chain constant region is a human heavy chain constant region, e.g., a human IgG constant region, e.g., a human IgG1 constant region. As described elsewhere herein, in certain aspects a heavy chain constant region or fragment thereof, e.g., a human IgG constant region or fragment thereof, can include one or more amino acid substitutions relative to a wild-type IgG constant domain wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain aspects the IgG constant domain can contain one or more of a substitution of the amino acid at Kabat position 252 with Tyrosine (Y), Phenylalanine (F), Tryptophan (W), or Threonine (T), a substitution of the amino acid at Kabat position 254 with Threonine (T), a substitution of the amino acid at Kabat position 256 with Serine (S), Arginine (R), Glutamine (Q), Glutamic acid (E), Aspartic acid (D), or Threonine (T), a substitution of the amino acid at Kabat position 257 with Leucine (L), a substitution of the amino acid at Kabat position 309 with Proline (P), a substitution of the amino acid at Kabat position 311 with Serine (S), a substitution of the amino acid at Kabat position 428 with Threonine (T), Leucine (L), Phenylalanine (F), or Serine (S), a substitution of the amino acid at Kabat position 433 with Arginine (R), Serine (S), Isoleucine (I), Proline (P), or Glutamine (Q), or a substitution of the amino acid at Kabat position 434 with Tryptophan (W), Methionine (M), Serine (S), Histidine (H), Phenylalanine (F), or Tyrosine. More specifically, the IgG constant domain can contain amino acid substitutions relative to a wild-type human IgG constant domain including as substitution of the amino acid at Kabat position 252 with Tyrosine (Y), a substitution of the amino acid at Kabat position 254 with Threonine (T), and a substitution of the amino acid at Kabat position 256 with Glutamic acid (E).

This disclosure provides an anti-IL-21 antibody or antigen-binding fragment thereof where the heavy chain is a human IgG1 YTE mutant, e.g., the heavy chain can comprise a heavy chain amino acid sequence at least 70%, 75%, 80%, 85%, 90%, 95%, or 100% identical to the reference amino acid sequence SEQ ID NO: 16, SEQ ID NO: 20, or SEQ ID NO: 24.

An anti-IL-21 antibody or antigen-binding fragment thereof provided herein, e.g., as described above, can include, in addition to a VH and a VL, and optionally a heavy chain constant region or fragment thereof, a light chain constant region or fragment thereof. In certain aspects the light chain constant region is a kappa lambda light chain constant region, e.g., a human kappa constant region or a human lambda constant region. In a specific aspect, the light chain constant region is a human kappa constant region.

This disclosure provides an anti-IL-21 antibody or antigen-binding fragment thereof where the light chain contains a human kappa constant region, e.g., the light chain can comprise a light chain amino acid sequence at least 70%, 75%, 80%, 85%, 90%, 95%, or 100% identical to the reference amino acid sequence SEQ ID NO: 18, SEQ ID NO: 22, or SEQ ID NO: 26. In certain aspects the disclosure provides an anti-IL-21 antibody or antigen-binding fragment thereof comprising a human IgG1 YTE heavy chain and a human kappa light chain, where the antibody is composed of SEQ ID NO: 16 and SEQ ID NO: 18, SEQ ID NO: 20 and SEQ ID NO: 22, or SEQ ID NO: 24 and SEQ ID NO: 26, respectively, or any antigen-binding fragment thereof.

Anti-IL-21 antibodies or fragments thereof provided herein can have beneficial properties. For example, the antibody or fragment thereof can inhibit, suppress, or block IL-21 from binding to an IL-21 receptor, e.g., expressed on a T cell, a B cell, an NK cell, an NKT cell, or a dendritic cell, or expressed recombinantly in a non-lymphoid cell. As a further example, the antibody or fragment can inhibit human or cynomolgus IL-21 binding to the human or cynomolgus IL-21 receptor but does not inhibit binding of mouse IL-21 to mouse IL-21 receptor. Such an anti-IL-21 antibody or fragment thereof can further inhibit, suppress, or block various IL-21-mediated activities, i.e., the antibody or fragment can be an antagonist of IL-21 activity. In certain aspects, an anti-IL-21 antibody or fragment thereof provided herein can inhibit, suppress, or block IL-21-mediated phosphorylation in the Jak/STAT pathway, e.g., inhibit, suppress or block phosphorylation of STAT3, in IL-21R-expressing cells, e.g., in human peripheral blood mononuclear cells (PBMC).

In certain aspects, an anti-IL-21 antibody or fragment thereof provided herein can inhibit, suppress, or block IL-21-mediated interferon-gamma (IFN-γ) production by NK cells. Such inhibition can be from naturally-occurring NK cells, e.g., human NK cells, or cultured NK cells, e.g., NK-92 cells.

In particular aspects, an anti-IL-21 antibody or fragment thereof provided herein can inhibit, suppress, or block IL-21-mediated B cell activation, differentiation or death during a humoral immune response. For example, an anti-IL-21 antibody or fragment thereof provided herein can inhibit, suppress, or block IL-21-mediated B cell differentiation of stimulated B cells into plasma cells. Certain antibodies provided herein can inhibit, suppress or block human and cynomolgus monkey IL-21-mediated differentiation of stimulated B cells into plasma cells. In certain aspects, the B cells can be isolated B cells to which IL-21 is exogenously added. In other aspects the B cells can be in contact with, either naturally or through co-culture, activated CD4+ T cells that express IL-21. In other aspects the human B cells can be in contact with, either naturally or through co-culture, human activated CD4+ T cells that express IL-21.

In certain aspects, an antibody or antigen-binding fragment thereof as provided herein can bind to IL-21 with a binding affinity characterized by a dissociation constant ($K_D$) of about 100 pM to about 0.1 pM as measured on a Kinetic Exclusion Assay (KinExA) 3000 platform.

In certain aspects, an anti-IL-21 antibody or antigen-binding fragment thereof can specifically bind to IL-21, e.g., human IL-21 or cynomolgus monkey IL-21, and antigenic fragments thereof with a dissociation constant or $K_D$ of less than $10^{-6}$ M, or of less than $10^{-7}$ M, or of less than $10^{-8}$ M, or of less than $10^{-9}$ M, or of less than $10^{-10}$ M, or of less than $10^{-11}$ M, of less than $10^{-12}$ M, of less than $10^{-13}$ M, of less than $10^{-14}$ M, or of less than $10^{-15}$ M as measured, e.g., by KINEXA® or BIACORE®. In one aspect, the humanized anti-IL-21 antibody K44VHa-N56Q can bind to human IL-21 with a $K_D$ about 515 fM (515×$10^{-15}$ M) and cynomolgus monkey IL-21 with a $K_D$ of about 352 fM (352×$10^{-15}$ M) as measured by KINEXA®.

In another embodiment, an anti-IL-21 antibody or antigen-binding fragment thereof of the invention binds to IL-21 and/or antigenic fragments thereof with a $K_{off}$ of less than $1\times10^{-3}$ s$^{-1}$, or less than $2\times10^{-3}$ s$^{-1}$. In other embodiments, an anti-IL-21 antibody or antigen-binding fragment thereof binds to IL-21 and antigenic fragments thereof with a $K_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-1}$ s$^{-1}$, less than less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$ as measured, e.g., by KINEXA® or BIACORE®.

In another embodiment, an anti-IL-21 antibody or antigen-binding fragment thereof of the invention binds to IL-21 and/or antigenic fragments thereof with an association rate constant or kon rate of at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, or at least $10^8$ M$^{-1}$ s$^{-1}$, or at least $10^9$ M$^{-1}$ s$^{-1}$ as measured, e.g., by KINEXA® or BIACORE®.

As noted above, a VH and/or VL amino acid sequence can be, e.g., 85%, 90%, 95%, 96%, 97%, 98% or 99% similar to a sequence set forth herein, and/or comprise 1, 2, 3, 4, 5 or more substitutions, e.g., conservative substitutions relative to a sequence set forth herein. An IL-21 antibody having VH and VL regions having a certain percent similarity to a VH region or VL region, or having one or more substitutions, e.g., conservative substitutions can be obtained by mutagenesis (e.g., site-directed or PCR-mediated mutagenesis) of nucleic acid molecules encoding VH and/or VL regions described herein, followed by testing of the encoded altered antibody for binding to IL-21 and optionally testing for retained function using the functional assays described herein.

The affinity or avidity of an antibody for an antigen can be determined experimentally using any suitable method well known in the art, e.g., flow cytometry, enzyme-linked immunosorbant assay (ELISA), or radioimmunoassay (RIA), or kinetics (e.g., KINEXA® or BIACORE™ analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein.) The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art and such as the buffer described herein.

The disclosure further provides an anti-IL-21 antibody or fragment thereof as described above, where the antibody is conjugated to a heterologous agent. In certain aspects the agent can be an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), or a combination of two or more of any said agents. Heteroconjugate anti-IL-21 antibodies are discussed in more detail elsewhere herein.

In certain embodiments, the IL-21-binding molecule is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curt. Opin. Biotechnol., 17:653-658 (2006), Nygren, FEBS J., 275:2668-76 (2008), and Skerra, FEBS J., 275:

2677-83 (2008), each of which is incorporated by reference herein in its entirety. In certain embodiments, phage display technology can been used to identify/produce an IL-21-binding polypeptide. In certain embodiments, the polypeptide comprises a protein scaffold of a type selected from the group consisting of protein A, a lipocalin, a fibronectin domain, an ankyrin consensus repeat domain, and thioredoxin.

III. Binding Molecules that Bind to the Same Epitope as Anti-IL-21 Antibodies and Antigen-Binding Fragments Thereof of the Invention In certain embodiments this disclosure provides an IL-21-binding molecule, e.g., an anti-IL-21 antibody or antigen-binding fragment thereof that binds to the same epitope as do the various anti-IL-21 antibodies described herein. The term "epitope" as used herein refers to a target protein determinant capable of binding to an antibody of the invention. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. Such antibodies can be identified based on their ability to cross-compete (e.g., to competitively inhibit the binding of, in a statistically significant manner) with antibodies such as 19E3, 9F11, 9H10, or 8B6, in standard IL-21 binding or activity assays. Accordingly, in one embodiment, the invention provides anti-IL-21 antibodies and antigen-binding fragments thereof, e.g., monoclonal antibodies, that compete for binding to IL-21 with another anti-IL-21 antibody or antigen-binding fragment thereof of the invention, such as murine monoclonal antibodies 19E3, 9F11, 9H10, or 8B6, or humanized variants as disclosed herein. The ability of a test antibody to inhibit the binding of, e.g., 19E3, 9F11, 9H10, or 8B6 demonstrates that the test antibody can compete with that antibody for binding to IL-21; such an antibody can, according to non-limiting theory, bind to the same or a related (e.g., a structurally similar or spatially proximal) epitope on IL-21 as the anti-IL-21 antibody or antigen-binding fragment thereof with which it competes. In one embodiment, the anti-IL-21 antibody or antigen-binding fragment thereof that binds to the same epitope on IL-21 as, e.g., murine monoclonal antibodies 19E3, 9F11, 9H10, or 8B6.

IV. Activity of IL-21 Binding Molecules

In some embodiments, an IL-21-binding molecule, e.g., an anti-IL-21 antibody or antigen-binding fragment thereof can suppress IL-21-mediated signal transduction in IL-21R-expressing cells. For example, an IL-21-binding molecule, e.g., an anti-IL-21 antibody or antigen-binding fragment thereof can suppress IL-21-mediated phosphorylation of STAT3. In addition, an IL-21-binding molecule, e.g., an anti-IL-21 antibody or antigen-binding fragment thereof can suppress IFNγ production by NK cells. Moreover, an IL-21-binding molecule, e.g., an anti-IL-21 antibody or antigen-binding fragment thereof can inhibit differentiation of stimulated B cells into plasma cells.

In some embodiments, an IL-21-binding molecule, e.g., an anti-IL-21 antibody or antigen-binding fragment thereof can suppress IL-21-mediated phosphorylation of STAT3 in IL-21R-expressing cells (e.g., PBMCs) as measured by flow cytometry, with an $IC_{50}$ lower than about 500 pM, lower than about 350 pM, lower than about 250 pM, lower than about 150 pM, lower than about 100 pM, lower than about 75 pM, lower than about 60 pM, lower than about 50 pM, lower than about 40 pM, lower than about 30 pM, lower than about 20 pM, lower than about 15 pM, lower than about 10 pM, or lower than about 5 pM. In certain aspects, an IL-21-binding molecule, e.g., an anti-IL-21 antibody or antigen-binding fragment thereof can suppress human IL-21-mediated phosphorylation of STAT3 in IL-21R-expressing cells (e.g., PBMCs) as measured by flow cytometry, with an $IC_{50}$ of about 22 pM, about 19 pM, about 17 pM, about 14 pM, about 13 pM, about 12 pM, about 6 pM, about 5 pM, or about 3 pM. In certain aspects, an IL-21-binding molecule, e.g., an anti-IL-21 antibody or antigen-binding fragment thereof can suppress cynomolgus monkey IL-21-mediated phosphorylation of STAT3 in IL-21R-expressing cells (e.g., PBMCs) as measured by flow cytometry, with an $IC_{50}$ of about 52 pM, about 51 pM, about 46 pM, about 19 pM, about 16 pM, about 10 pM, or about 6 pM.

In some embodiments, an IL-21-binding molecule, e.g., an anti-IL-21 antibody or antigen-binding fragment thereof can suppress IL-21-mediated IFNγ production from NK cells as measured by the MSD human IFNγ single-plex assay with an $IC_{50}$ lower than about 100 pM, lower than about 400 pM, lower than about 100 pM, lower than about 75 pM, lower than about 60 pM, lower than about 50 pM, lower than about 40 pM, lower than about 30 pM, lower than about 20 pM, lower than about 15 pM, lower than about 10 pM, or lower than about 5 pM. In certain aspects, an IL-21-binding molecule, e.g., an anti-IL-21 antibody or antigen-binding fragment thereof can suppress human IL-21-mediated IFNγ production from NK-92 cell line as measured by the MSD human IFNγ single-plex assay with an $IC_{50}$ of about 99 pM, about 93 pM, about 55 pM, about 41 pM, or about 20 pM. In certain aspects, an IL-21-binding molecule, e.g., an anti-IL-21 antibody or antigen-binding fragment thereof can suppress cynomolgus monkey IL-21-mediated IFNγ production from NK-92 cell line as measured by the MSD human IFNγ single-plex assay with an $IC_{50}$ of about 83 pM, about 81 pM, about 60 pM, about 37 pM, or about 3 pM.

In some embodiments, an IL-21-binding molecule, e.g., an anti-IL-21 antibody or antigen-binding fragment thereof can suppress IL-21-mediated differentiation of stimulated B cells, e.g., naïve B cells and/or B memory cells stimulated with anti-CD40 and anti-IgM F(ab')2, into plasma cells, e.g., IgG producing plasma cells, as measured by flow cytometry or ELISA with an $IC_{50}$ lower than about 150 nM, lower than about 75 nM, lower than about 50 nM, lower than about 30 nM, lower than about 10 nM, lower than about 1,600 pM, lower than about 1,400 pM, lower than about 1000 pM, lower than about 800 pM, lower than about 700 pM, or lower than about 600 pM. In certain aspects, an IL-21-binding molecule, e.g., an anti-IL-21 antibody or antigen-binding fragment thereof can suppress human IL-21-mediated differentiation of stimulated B cells, e.g., naïve B cells and/or B memory cells simulated with anti-CD40 and anti-IgM F(ab')2, into plasma cells, e.g., IgG producing plasma cells, as measured by flow cytometry or ELISA with an $IC_{50}$ of about 115 nM, about 47 nM, about 1.5 nM, about 777 pM, about 618 pM, or about 573 pM. In certain aspects, an IL-21-binding molecule, e.g., an anti-IL-21 antibody or antigen-binding fragment thereof can suppress cynomolgus monkey IL-21-mediated differentiation of stimulated human B cells, e.g., naïve B cells and/or B memory cells simulated with anti-CD40 and anti-IgM F(ab')2, into plasma cells, e.g., IgG producing plasma cells, as measured by flow cytometry or ELISA with an $IC_{50}$ of about 74 nM, about 30 nM, about 9 nM, about 1.3 nM, about 1.0 nM, about 775 pM, or about 659 pM. In certain aspects, an IL-21-binding molecule, e.g., an anti-IL-21 antibody or antigen-binding fragment thereof can suppress cynomolgus monkey IL-21-mediated differentiation of stimulated B cells into plasma cells, but not human IL-21-mediated B cell differentiation into plasma cells.

In certain aspects an IL-21-binding molecule, e.g., an anti-IL-21 antibody or antigen-binding fragment thereof can suppress B cell differentiation into plasma cells driven by activated CD4+ T cells which produce co-stimulatory molecules such as CD40L and B cell tropic cytokines such as IL-21. In other aspects, an IL-21-binding molecule, e.g., an anti-IL-21 antibody or antigen-binding fragment thereof can inhibit IL-21-driven proliferation of human naive CD4+ T-cells.

V. Preparation of Anti-IL-21 Antibodies and Antigen-binding Fragments

Monoclonal anti-IL-21 antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively anti-IL-21 monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant anti-IL-21 monoclonal antibodies or antigen-binding fragments thereof of the desired species can be isolated from phage display libraries expressing CDRs of the desired species as described (McCafferty et al., 1990, Nature, 348:552-554; Clackson et al., 1991, Nature, 352: 624-628; and Marks et al., 1991, J. Mol. Biol., 222:581-597).

The polynucleotide(s) encoding an anti-IL-21 antibody or an antigen-binding fragment thereof can further be modified in a number of different manners using recombinant DNA technology to generate alternative antibodies. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In certain embodiments, the anti-IL-21 antibody or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373).

Also, the anti-IL-21 human antibody or antigen-binding fragment thereof can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227: 381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety).

Affinity maturation strategies and chain shuffling strategies (Marks et al., 1992, Bio/Technology 10:779-783, incorporated by reference in its entirety) are known in the art and can be employed to generate high affinity human antibodies or antigen-binding fragments thereof.

In some embodiments, an anti-IL-21 monoclonal antibody can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing IL-21 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen IL-21 and other favorable biological properties. To achieve this goal, humanized (or human) or engineered anti-IL-21 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as IL-21. In this way, framework (FW) residues can be selected and combined from the consensus and import sequences so that the desired antibody characteristic, such as increased affinity for the target antigen(s), is achieved.

Humanization, resurfacing or engineering of anti-IL-21 antibodies or antigen-binding fragments thereof of the present invention can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-IL-21 humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633, 425; and 5,661,016.

In certain embodiments an anti-IL-21 antibody fragment is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, anti-IL-21 antibody fragments are produced recombinantly. Fab, Fv, and scFv antibody fragments can all be expressed in and secreted from E. coli or other host cells, thus allowing the production of large amounts of these fragments. Such anti-IL-21 antibody fragments can also be isolated from the antibody phage libraries discussed above. The anti-IL-21 antibody fragments can also be linear antibodies as described in U.S. Pat. No. 5,641,870. Other techniques for the production of antibody fragments will be apparent to the skilled practitioner.

According to the present invention, techniques can be adapted for the production of single-chain antibodies specific to IL-21 (see, e.g., U.S. Pat. No. 4,946,778). In addition, methods can be adapted for the construction of Fab expression libraries (see, e.g., Huse et al., Science 246:1275-1281 (1989)) to allow rapid and effective identification of monoclonal Fab fragments with the desired specificity for IL-21, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

In certain aspects, an anti-IL-21 antibody or antigen-binding fragment thereof can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are known in the art.

Heteroconjugate anti-IL-21 antibodies and antigen-binding fragments thereof are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is contemplated that the heteroconjugate anti-IL-21 antibodies and antigen-binding fragments thereof can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

Modified anti-IL-21 antibodies or antigen-binding fragments thereof as provided herein can comprise any type of variable region that provides for the association of the antibody or polypeptide with IL-21. In this regard, the variable region can comprise or be derived from any type of mammal that can be induced to mount a humoral response and generate immunoglobulins against the desired antigen. As such, the variable region of an anti-IL-21 antibody or antigen-binding fragment thereof can be, for example, of human, murine, non-human primate (e.g., cynomolgus monkeys, macaques, etc.) or lupine origin. In some embodiments both the variable and constant regions of the modified anti-IL-21 antibodies or antigen-binding fragments thereof are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains of an anti-IL-21 antibody or antigen-binding fragment thereof are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified anti-IL-21 antibodies or antigen-binding fragments thereof of this invention will comprise antibodies (e.g., full-length antibodies or antigen-binding fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain can be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with an Fc receptor site on the antibody Fc region binding to a Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, an anti-IL-21 antibody or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody. In other cases it can be that constant region modifications, consistent with this invention, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well-known biochemical or molecular engineering techniques well within the purview of the skilled artisan.

In certain embodiments, an -IL-21 binding molecule that is an antibody or antigen-binding fragment thereof does not have one or more effector functions. For instance, in some embodiments, the antibody or antigen-binding fragment thereof has no antibody-dependent cellular cytoxicity (ADCC) activity and/or no complement-dependent cytoxicity (CDC) activity. In certain embodiments, the anti-IL-21 antibody or antigen-binding fragment thereof does not bind to an Fc receptor and/or complement factors. In certain embodiments, the antibody or antigen-binding fragment thereof has no effector function.

In certain embodiments, an anti-IL-21 antibody or antigen-binding fragment thereof can be engineered to fuse the CH3 domain directly to the hinge region of the respective modified antibodies or fragments thereof. In other constructs a peptide spacer can be inserted between the hinge region and the modified CH2 and/or CH3 domains. For example, compatible constructs can be expressed in which the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. Accordingly, in certain embodiments, any spacer added to the construct can be relatively non-immunogenic, or even omitted altogether, so as to maintain the desired biochemical qualities of the modified antibodies.

Besides the deletion of whole constant region domains, anti-IL-21 antibodies or antigen-binding fragments thereof provided herein can be modified by the partial deletion or substitution of a few or even a single amino acid in a constant region. For example, the mutation of a single amino acid in selected areas of the CH2 domain can be enough to substantially reduce Fc binding and thereby increase tumor localization. Similarly one or more constant region domains that control the effector function (e.g., complement C1Q binding) can be fully or partially deleted. Such partial deletions of the constant regions can improve selected characteristics of the antibody or antigen-binding fragment thereof (e.g., serum half-life) while leaving other desirable functions associated with the subject constant region domain intact. Moreover, the constant regions of the disclosed anti-IL-21 antibodies and antigen-binding fragments thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents that are substantially homologous to the murine, chimeric, humanized or human anti-IL-21 antibodies, or antigen-binding fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

An anti-IL-21 antibody or antigen-binding fragment thereof can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

VI. Polynucleotides Encoding IL-21-Binding Molecules and Expression Thereof

This disclosure provides polynucleotides comprising nucleic acid sequences that encode a polypeptide that specifically binds IL-21 or an antigen-binding fragment thereof. For example, the invention provides a polynucleotide comprising a nucleic acid sequence that encodes an anti-IL-21 antibody or encodes an antigen-binding fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, a polynucleotide can be isolated. In certain embodiments, a polynucleotide can be substantially pure. In certain embodiments a polynucleotide can be cDNA or are derived from cDNA. In certain embodiments a polynucleotide can be recombinantly produced. In certain embodiments a polynucleotide can comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for an IL-21-binding pro-protein which is the mature protein plus additional 5' amino acid residues.

In certain aspects this disclosure provides an isolated polynucleotide comprising a nucleic acid encoding an antibody VL, wherein the VL comprises VL-CDR1, VL-CDR2, and VL-CDR3 amino acid sequences identical to, or identical except for eight, seven, six, five, four, three, two, or one amino acid substitutions in one or more of the VL-CDRS to: SEQ ID NOs: 12, 13, and 14, SEQ ID NOs: 34, 35 and 36, SEQ ID NOs: 48, 49, and 50, or SEQ ID NOs: 58, 59, and 60, respectively.

The disclosure further provides an isolated polynucleotide comprising a nucleic acid encoding an antibody VH, wherein the VH comprises VH-CDR1, VH-CDR2, and VH-CDR3 amino acid sequences identical to, or identical except for eight, seven, six, five, four, three, two, or one amino acid substitutions in one or more of the VH-CDRS to: SEQ ID NOs: 7, 8, and 9, SEQ ID NOs: 29, 30 and 31, SEQ ID NOs: 43, 44, and 45, or SEQ ID NOs: 53, 54, and 55, respectively.

The disclosure further provides an isolated polynucleotide comprising a nucleic acid encoding an antibody VL, wherein the VL comprises an amino acid sequence at least 70%, 75%, 80%, 85%, 90%, 95%, or 100% identical to a reference amino acid sequence selected from the group consisting of SEQ ID NO: 11, SEQ ID NO: 17, SEQ ID NO: 21, SEQ ID NO: 25, SEQ ID NO: 33, SEQ ID NO: 39, SEQ ID NO: 40, SEQ ID NO: 47, and SEQ ID NO: 57.

Moreover, the disclosure provides an isolated polynucleotide comprising a nucleic acid encoding an antibody VH, wherein the VH comprises an amino acid sequence at least 70%, 75%, 80%, 85%, 90%, 95%, or 100% identical to a reference amino acid sequence selected from the group consisting of SEQ ID NO: 6, SEQ ID NO: 15, SEQ ID NO: 19, SEQ ID NO: 23, SEQ ID NO: 28, SEQ ID NO: 40, SEQ ID NO: 37, SEQ ID NO: 38, SEQ ID NO: 42 and SEQ ID NO: 52.

In certain aspects, an antibody or antigen-binding fragment thereof comprising a VH or VL encoded by a polynucleotide as described above, can specifically bind to IL-21, e.g., human or cynomolgus monkey IL-21. In certain cases such an antibody or antigen-binding fragment thereof can specifically bind to the same epitope as an antibody or antigen-binding fragment thereof comprising the VH and VL of 19E3, 9F11, 8B6, or 9H10. In certain aspects the disclosure provides a polynucleotide or combination of polynucleotides encoding a binding molecule, e.g., an antibody or antigen-binding fragment thereof, that specifically binds to IL-21.

Further provided is a vector comprising a polynucleotide as described above. Suitable vectors are described elsewhere herein, and are known to those of ordinary skill in the art.

In certain aspects, the disclosure provides a composition, e.g., a pharmaceutical composition, comprising a polynucleotide or vector of claim as described above, optionally further comprising one or more carriers, diluents, excipients, or other additives.

In certain aspects, the disclosure provides a polynucleotide composition comprising: a polynucleotide that comprises a nucleic acid encoding a VH, and polynucleotide that comprises a nucleic acid encoding a VL. According to this aspect, the VL and VH together can comprise VL-CDR1, VL-CRD2, VL-CDR3, VH-CDR1, VH-CDR2, and VH-CDR3 amino acid sequences identical or identical except for eight, seven, six, five, four, three, two, or one amino acid substitutions in one or more CDRs to: SEQ ID NOs: 12, 13, 14, 7, 8, and 9, SEQ ID NOs: 34, 35, 36, 29, 30, and 31, SEQ ID NOs: 48, 49, 50, 43, 44, and 45, or SEQ ID NOs: 58, 59, 60, 53, 54, and 55, respectively.

In further aspects the disclosure provides a polynucleotide composition comprising: a polynucleotide that comprises a nucleic acid encoding a VH and polynucleotide that comprises a nucleic acid encoding a VL, wherein the VL and VH comprise, respectively, amino acid sequences at least 70%, 75%, 80%, 85%, 90%, 95%, or 100% identical to reference amino acid sequences: SEQ ID NO: 6 and SEQ ID NO: 11, SEQ ID NO: 15 and SEQ ID NO: 17, SEQ ID NO: 19 and SEQ ID NO: 21, SEQ ID NO: 23 and SEQ ID NO: 25, SEQ ID NO: 28 and SEQ ID NO: 33, SEQ ID NO: 40 and SEQ ID NO: 39, SEQ ID NO: 37 and SEQ ID NO: 39, SEQ ID NO: 38 and SEQ ID NO: 39, SEQ ID NO: 37 and 40, SEQ ID NO: 42 and SEQ ID NO: 47, or SEQ ID NO: 52 and SEQ ID NO: 57, respectively.

In certain aspects, the VH and VL are encoded by nucleic acid sequences at least 70%, 75%, 80%, 85%, 90%, 95%, or 100% identical to reference nucleic acid sequences SEQ ID NO:5 and SEQ ID NO: 10, SEQ ID NO:27 and SEQ ID NO:32, SEQ ID NO: 41 and SEQ ID NO:46, or SEQ ID NO: 51 and SEQ ID NO:56, respectively.

In a polynucleotide composition as described above the polynucleotide comprising a nucleic acid encoding a VH and the polynucleotide comprising a nucleic acid encoding a VL can reside in a single vector, or can be on separate vectors. Accordingly the disclosure provides one or more vectors comprising the polynucleotide composition described above.

In some cases, a polynucleotide composition encoding a VH and VL as described above can encode an antibody or antigen-binding fragment thereof that can specifically bind to IL-21, e.g., human or cynomolgus monkey IL-21. In some aspects the polynucleotide composition encodes an antibody or antigen-binding fragment thereof that can specifically bind to the same epitope as an antibody or antigen-binding fragment thereof comprising the VH and VL of 19E3, 9F11, 8B6, or 9H10.

This disclosure further provides a host cell comprising a polynucleotide, polynucleotide composition, or vector as provided above, where host cell can, in some instances, express an antibody or antigen-binding fragment thereof that specifically binds to IL-21. Such a host cell can be utilized in a method of making an antibody or antigen-binding fragment thereof as provided herein, where the method includes (a) culturing the host cell and (b) isolating the antibody or antigen-binding fragment thereof expressed from the host cell.

In certain embodiments the polynucleotides comprise the coding sequence for the mature IL-21-binding polypeptide, e.g., an anti-IL-21 antibody or an antigen-binding fragment thereof fused in the same reading frame to a marker sequence that allows, for example, for purification of the encoded polypeptide. For example, the marker sequence can be a hexa-histidine tag (SEQ ID NO: 67) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Polynucleotide variants are also provided. Polynucleotide variants can contain alterations in the coding regions, non-coding regions, or both. In some embodiments polynucleotide variants contain alterations that produce silent substitutions, additions, or deletions, but do not alter the properties or activities of the encoded polypeptide. In some embodiments, polynucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli). Vectors and cells comprising the polynucleotides described herein are also provided.

In some embodiments a DNA sequence encoding an IL-21-binding molecule, e.g., an anti-IL-21 antibody or an antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest can be inserted into an expression vector and operatively linked to an expression control sequence appropriate for expression of the protein in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain embodiments, recombinant expression vectors are used to amplify and express DNA encoding anti-IL-21 antibodies or antigen-binding fragments thereof. Recombinant expression vectors are replicable DNA constructs which have synthetic or cDNA-derived DNA fragments encoding a polypeptide chain of an anti-IL-21 antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from E.

*coli*, including pCR 1, pBR322, pMB9 and their derivatives, wider host range plasmids, such as M13 and filamentous single-stranded DNA phages.

Suitable host cells for expression of an IL-21-binding molecule, e.g., an anti-IL-21 antibody or antigen-binding fragment thereof include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be advantageously employed to express recombinant IL-21-binding molecules, e.g., anti-IL-21 antibodies or antigen-binding fragments thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

IL-21-binding molecules, e.g., anti-IL-21 antibodies or antigen-binding fragments thereof produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 67), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an IL-21-binding molecule. Some or all of the foregoing purification steps, in various combinations, can also be employed to provide a homogeneous recombinant protein.

A recombinant IL-21-binding protein, e.g., an anti-IL-21 antibody or antigen-binding fragment thereof produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

VI. Treatment Methods Using Therapeutic Anti-IL-21 Antibodies

Methods are provided for the use of IL-21 binding molecules, e.g., anti-IL-21 antibodies, including antigen-binding fragments, variants, and derivatives thereof, to treat patients having a disease associated with IL-21 expression or IL-21-secreting cells. By "IL-21-secreting cells" is intended cells expressing IL-21, e.g., activated T-helper cells. Methods for detecting IL-21 expression are well known in the art and include, but are not limited to, PCR techniques, immunohistochemistry, flow cytometry, Western blot, ELISA, and the like.

The following discussion refers to diagnostic methods and methods of treatment of various diseases and disorders with an IL-21-binding molecule, e.g., an anti-IL-21 antibody or antigen-binding fragment, variant, or derivative that retains the desired properties of anti-IL-21 antibodies provided herein, e.g., capable of specifically binding IL-21 and antagonizing IL-21 activity. In some embodiments, IL-21-binding molecules are murine, human, or humanized antibodies. In some embodiments, the IL-21-antibody is identical to one of the murine monoclonal antibodies 19E3, 9F11, 9H10 or 8B6. In some embodiments, the IL-21-antibody is derived from one of the murine monoclonal antibodies 19E3, 9F11, 9H10 or 8B6. In certain embodiments the derived antibody is a humanized antibody. In other embodiments, the IL-21-binding molecule comprises a YTE-mutated human IgG1 constant region. In specific embodiments, the IL-21-binding molecule is K44VHa-N56Q.

In one embodiment, treatment includes the application or administration of an IL-21 binding molecules, e.g., an anti-IL-21 antibody or antigen-binding fragment, variant, or derivative thereof as provided herein to a subject or patient, or application or administration of the IL-21 binding molecule to an isolated tissue or cell line from a subject or patient, where the subject or patient has a disease, a symptom of a disease, or a predisposition toward a disease. In another embodiment, treatment can also include the application or administration of a pharmaceutical composition comprising an IL-21 binding molecule, e.g., an anti-IL-21 antibody or antigen-binding fragment, variant, or derivative thereof as provided herein to a subject or patient, or application or administration of a pharmaceutical composition comprising an IL-21 binding molecule to an isolated tissue or cell line from a subject or patient, who has a disease, a symptom of a disease, or a predisposition toward a disease.

IL-21 binding molecules, e.g., anti-IL-21 antibodies or antigen-binding fragments, variants, or derivatives thereof provided herein are useful for the treatment of various inflammatory, immune-mediated, or autoimmune diseases or disorders. Such inflammatory, immune-mediated, or autoimmune diseases or disorders may be a B-cell driven disease or a T-cell driven disease. In one embodiment, IL-21 binding molecules, e.g., anti-IL-21 antibodies or antigen-binding fragments, variants, or derivatives thereof are provided for use in the treatment or prophylaxis of inflammatory, immune-mediated, or autoimmune diseases or disorders. Examples of inflammatory, immune-mediated, or autoimmune disease or disorders include, but are not limited to vasculitis, e.g., Anti-neutrophil cytoplasm antibodies (ANCA), ANCA-associated vasculitis (AAV) or giant cell arteritis (GCA) vasculitis, Sjögren's syndrome, inflammatory bowel disease (IBD), Pemphigus vulgaris, lupus nephritis, psoriasis, thyroiditis, Type I Diabetes, Idiopathic thrombocytopenic purpura (ITP), Ankylosing spondylitis, Multiple sclerosis, systemic lupus erythematosus (SLE), rheumatoid arthritis, Crohn's disease, Myasthenia Gravis, neuromyelitis optica (NMO), IgG4-related disease, systemic sclerosis, insulin-dependent diabetes mellitus (IDDM), akylosing spondylitis, atopic dermatitis, uveitis, and Graft-versus-host disease (GVHD). In one embodiment, IL-21 binding molecules, e.g., anti-IL-21 antibodies or antigen-binding fragments, variants, or derivatives thereof are provided for use in the treatment or prophylaxis of B-cell driven diseases or malignancies. An example of a B-cell driven malignancy can include follicular lymphoma (FL), diffuse large B cell lymphoma (DLBCL), Hodgkins lymphoma (HL), chronic lymphocytic leukemia (CLL), mantle cell lymphoma, Burkitt's lymphoma, Waldenstrom macroglobulinemia and multiple myeloma (MM). In one embodiment, IL-21 binding molecules, e.g., anti-IL-21 antibodies or antigen-binding fragments, variants, or derivatives thereof are provided for use in the treatment or prophylaxis of T-cell driven diseases or malignancies. An example of a T-cell driven malignancy can include angioimmunoblastic T cell lymphoma which is a malignancy derived from follicular helper T Cells (Tfh), anaplastic large cell lymphoma, Adult T-cell leukemia, cutaneous T-cell lymphoma and Sezary syndrome In accordance with the methods of the present invention, at least one IL-21 binding molecule, e.g., an anti-IL-21 antibody or antigen-binding fragment, variant, or derivative thereof as defined elsewhere herein is used to promote a positive therapeutic response with respect to an autoimmune response. By "positive therapeutic response" with respect to autoimmune treatment is intended any improvement in the disease conditions associated with the activity of these binding molecules, e.g., anti-IL-21 antibodies or antigen-binding fragments, variants, or derivatives thereof, and/or an improvement in the symptoms associated with the disease. Thus, for example, an improvement in the disease can be characterized as a complete response. By "complete response" is intended an absence of clinically detectable disease with normalization of any previously test results. Such a response can in some cases persist, e.g., for at least one month following treatment according to the methods of the invention. Alternatively, an improvement in the disease can be categorized as being a partial response.

Clinical response can be assessed using screening techniques such as magnetic resonance imaging (MRI) scan, x-radiographic imaging, computed tomography (CT) scan, flow cytometry or fluorescence-activated cell sorter (FACS) analysis, histology, gross pathology, and blood chemistry, including but not limited to changes detectable by ELISA, ELISPOT, RIA, chromatography, and the like. In addition to these positive therapeutic responses, the subject undergoing therapy with the IL-21 binding molecule, e.g., an anti-IL-21 antibody or antigen-binding fragment, variant, or derivative thereof, can experience the beneficial effect of an improvement in the symptoms associated with the disease.

Also provided is the use of IL-21 binding molecules, e.g., anti-IL-21 antibodies or antigen-binding fragments, variants, or derivatives thereof, for diagnostic monitoring of protein levels (e.g., IL-21 levels) in blood or tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

VII. Pharmaceutical Compositions and Administration Methods

Methods of preparing and administering IL-21 binding molecules, e.g., anti-IL-21 antibodies, or antigen-binding fragments, variants, or derivatives thereof provided herein to a subject in need thereof are well known to or are readily determined by those skilled in the art. The route of administration of the IL-21 binding molecule, e.g., the anti-IL-21 antibody, or antigen-binding fragment, variant, or derivative thereof can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, another example of a form for administration would be a solution for injection, in particular for intravenous or intraarterial injection or drip. Usually, a suitable pharmaceutical composition can comprise a buffer (e.g. acetate, phosphate or citrate buffer), a surfactant (e.g. polysorbate), optionally a stabilizer agent (e.g. human albumin), etc. In other methods compatible with the teachings herein, IL-21 binding molecules, e.g., anti-IL-21 antibodies, or antigen-binding fragments, variants, or derivatives thereof as provided herein can be delivered directly to the site of the adverse cellular population thereby increasing the exposure of the diseased tissue to the therapeutic agent. In one embodiment, the administration is directly to the airway, e.g., by inhalation or intranasal administration.

As discussed herein, IL-21 binding molecules, e.g., anti-IL-21 antibodies, or antigen-binding fragments, variants, or derivatives thereof provided herein can be administered in a pharmaceutically effective amount for the in vivo treatment of IL-21-mediated diseases such as inflammatory, immune-mediated, or autoimmune diseases or disorders. In this regard, it will be appreciated that the disclosed binding molecules can be formulated so as to facilitate administration and promote stability of the active agent. Pharmaceutical compositions in accordance with the present invention can comprise a pharmaceutically acceptable, non-toxic, sterile carrier such as physiological saline, non-toxic buffers, preservatives and the like. For the purposes of the instant application, a pharmaceutically effective amount of an IL-21 binding molecule, e.g., an anti-IL-21 antibody, or antigen-binding fragment, variant, or derivative thereof, conjugated or unconjugated, means an amount sufficient to achieve effective binding to a target and to achieve a benefit, e.g., to ameliorate symptoms of a disease or condition or to detect a substance or a cell. Suitable formulations for use in the therapeutic methods disclosed herein are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an IL-21 binding molecule, e.g., an anti-IL-21 antibody, or fragment, variant, or derivative thereof, that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-IL-21 antibodies, or antigen-binding fragments, variants, or derivatives thereof can be administered to a human or other animal in accordance with the aforementioned methods of treatment in an amount sufficient to produce a therapeutic effect. The anti-IL-21 antibodies or antigen-binding fragments, variants, or derivatives thereof provided herein can be administered to such human or other animal in a conventional dosage form prepared by combining the antibody or antigen-binding fragment, variant, or derivative thereof of the invention with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables. A cocktail comprising one or more species of IL-21 binding molecules, e.g., anti-IL-21 antibodies, or antigen-binding fragments, variants, or derivatives thereof, of the invention can also be used.

By "therapeutically effective dose or amount" or "effective amount" is intended an amount of an IL-21 binding molecule, e.g., antibody or antigen-binding fragment, variant, or derivative thereof, that when administered brings about a positive therapeutic response with respect to treatment of a patient with a disease or condition to be treated.

Therapeutically effective doses of the compositions of the present invention, for treatment of IL-21-mediated diseases such as inflammatory, immune-mediated, or autoimmune disease or disorders vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of at least one IL-21 binding molecule, e.g., antibody or binding fragment, variant, or derivative thereof to be administered is readily determined by one of ordinary skill in the art without undue experimentation given this disclosure. Factors influencing the mode of administration and the respective amount of at least one IL-21 binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of an IL-21 binding molecule, e.g., antibody, or fragment, variant, or derivative thereof, to be administered will be dependent upon the mode of administration and whether the subject will undergo a single dose or multiple doses of this agent.

This disclosure also provides for the use of an IL-21 binding molecule, e.g., an anti-IL-21 antibody or antigen-binding fragment, variant, or derivative thereof, for use in the treatment of an inflammatory, immune-mediated, or autoimmune disease or disorder, e.g., vasculitis, e.g., ANCA or GCA vasculitis, Sjögren's syndrome, systemic lupus erythematosus and/or lupus nephritis, rheumatoid arthritis, Crohn's disease, Myasthenia Gravis, or GVHD.

This disclosure also provides for the use of an IL-21 binding molecule, e.g., an anti-IL-21 antibody or antigen-binding fragment, variant, or derivative thereof, in the manufacture of a medicament for treating an inflammatory, immune-mediated or autoimmune disease or disorder, e.g., vasculitis, e.g., ANCA or GCA vasculitis, Sjögren's syndrome, systemic lupus erythematosus and/or lupus nephritis, rheumatoid arthritis, Crohn's disease, Myasthenia Gravis, or GVHD.

VIII. Diagnostics

This disclosure further provides a diagnostic method useful during diagnosis of IL-21-mediated diseases such as certain inflammatory, immune-mediated, or autoimmune diseases or disorders, which involves measuring the expression level of IL-21 protein tissue or body fluid from an individual and comparing the measured expression level with a standard IL-21 expression level in normal tissue or body fluid, whereby an increase in the expression level compared to the standard is indicative of a disorder treatable by an IL-21 binding molecule, e.g., an anti-IL-21 antibody or antigen-binding fragment thereof as provided herein.

The anti-IL-21 antibodies and antigen-binding fragments, variants, and derivatives thereof provided herein can be used to assay IL-21 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting IL-21 protein expression include immunoassays, such as the enzyme linked immunosorbent assay (ELISA), immunoprecipitation, or Western blotting.

By "assaying the expression level of IL-21 polypeptide" is intended qualitatively or quantitatively measuring or estimating the level of IL-21 polypeptide in a first biological sample either directly (e.g., by determining or estimating absolute protein level) or relatively (e.g., by comparing to the disease associated polypeptide level in a second biological sample). The IL-21 polypeptide expression level in the first biological sample can be measured or estimated and compared to a standard IL-21 polypeptide level, the standard being taken from a second biological sample obtained from an individual not having the disorder or being determined by averaging levels from a population of individuals not having the disorder. As will be appreciated in the art, once the "standard" IL-21 polypeptide level is known, it can be used repeatedly as a standard for comparison.

By "biological sample" is intended any biological sample obtained from an individual, cell line, tissue culture, or other source of cells potentially expressing IL-21. Methods for obtaining tissue biopsies and body fluids from mammals are well known in the art.

IX. Kits Comprising IL-21-Binding Molecules

This disclosure further provides kits that comprise an IL-21 binding molecule, e.g., an anti-IL-21 antibody or antigen-binding fragment thereof described herein and that can be used to perform the methods described herein. In certain embodiments, a kit comprises at least one purified anti-IL-21 antibody or an antigen-binding fragment thereof in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed IL-21-binding molecules, e.g., anti-IL-21 antibodies or antigen-binding fragments thereof can be readily incorporated into one of the established kit formats which are well known in the art.

X. Immunoassays

IL-21 binding molecules provided herein, e.g., anti-IL-21 antibodies or antigen-binding fragments, variants, or derivatives thereof of the molecules provided herein can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), ELISPOT, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

IL-21-binding molecules, e.g., anti-IL-21 antibodies or antigen-binding fragments, variants, or derivatives thereof provided herein can be employed histologically, as in immunofluorescence, immunoelectron microscopy or non-immunological assays, for in situ detection of IL-21 or conserved variants or peptide fragments thereof. In situ detection can be accomplished by removing a histological specimen from a patient, and applying thereto a labeled IL-21-binding molecule, e.g., an anti-IL-21 antibody or antigen-binding fragment thereof, variant, or derivative thereof, e.g., applied by overlaying the labeled IL-21-binding molecule (e.g., and antibody or fragment) onto a biological sample. Through the use of such a procedure, it is possible to determine not only the presence of IL-21, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

The binding activity of a given lot of an IL-21-binding molecule, e.g., an anti-IL-21 antibody or antigen-binding fragment, variant, or derivative thereof can be determined according to well-known methods. Those skilled in the art will be able to determine operative and optimal assay conditions for each determination by employing routine experimentation.

Methods and reagents suitable for determination of binding characteristics of an isolated IL-21-binding molecule, e.g., an anti-IL-21 antibody or antigen-binding fragment, variant, or an altered/mutant derivative thereof, are known in the art and/or are commercially available. Equipment and software designed for such kinetic analyses are commercially available (e.g., BIAcore®, BIAevaluation® software, GE Healthcare; KINEXA® Software, Sapidyne Instruments).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

Example 1

Production and Humanization of Anti-IL-21 Murine Monoclonal Antibodies

Immunization of Mice and Anti-IL-21 Hybridoma Generation

Six-week old female Balb/c mice received 8 rounds of intra-peritoneal (IP) and metatarsal injections of purified recombinant human IL-21 alternating with cynomolgus monkey IL-21 protein conjugated to BSA (Imject Maleimide-Activated BSA Kit, Pierce). Briefly, starting on day 1 mice were immunized with 10 µg IP and 2.5 µg metatarsal of immunogen emulsified in Imject Alum (Thermo Scientific) as per manufacturer's instructions. Immunization lasted 28 days at intervals of 4 days. Test bleeds were collected on days 15 and 28 via retro-orbital bleeds in serum separation tubes. Sera were assayed by ELISA for direct binding to IL-21 and competition with IL-21R. Based on neutralizing titers in the competition ELISA, mice were selected to receive a pre-fusion boost with 10 µg of human IL-21 conjugated to BSA and sacrificed on day 30. Splenocytes and lymph node cells were harvested and fused to P3-X63-Ag8.653 myeloma using PEG to generate hybridomas. Anti-IL-21 specific hybridomas were identified by screening the hybridoma supernatants in direct binding and competition ELISA as described before. Positive hybridomas were further tested for neutralization activity in a cell based assay using down modulation of STAT3 phosphorylation as a read out (IL-21 signals through STAT3). Neutralizing hybridomas were then limited dilution cloned and expanded for antibody purification.

Competition ELISA was used throughout the hybridoma campaign to identify the good responders of mice after IL-21 immunization, followed by screening with the same method for neutralizing hybridomas. Briefly, Maxisorp ELISA plate (NUNC) was coated with 2 µg/ml of IL-21R-Fc in phosphate-buffered saline (PBS) at 4° C. overnight. The plate was then blocked with 3% BSA in PBST (PBS+0.1% Tween) at room temperature for one hour. In parallel, test bleeds were serially diluted (to screen for good responders) or IgG concentrations of hybridoma culture supernatants were normalized and pre-incubated with 2 nM biotinylated IL-21. After pre-incubation, the mixture was then added to each ELISA plate well and further incubated at room temperature for half an hour. After washing, streptavidin-HRP was added to each well to detect the level of bound IL-21 as a gauge of inhibition of IL-21/IL-21R-Fc interaction by test bleeds or hybridoma IgGs.

Isolation, Cloning, Sequencing, Expression, and Purification of Anti-IL-21 Murine mAbs Hybridoma culture supernatants were analyzed for their inhibitory ability against IL-21/IL-21R-Fc interaction following the procedure described in competition ELISA. Positive ones were put through limited dilution cloning (LDC) procedure to guarantee the clonality. After the functionalities of the subclones were confirmed, they were subjected to molecular cloning.

mRNA from hybridomas was isolated using the Dynabeads mRNA Direct Kit according to the manufacturer's instructions. The mRNA was then converted to cDNA by reverse transcriptase polymerase chain reaction using SuperScript III Reverse Transcriptase. Two sets of cDNA were synthesized to avoid PCR inaccuracies. The cDNAs were used as templates to amplify antibody variable regions of light chain and heavy chain (VL and VH). The PCR was performed using the Invitrogen high fidelity Taq polymerase and the Novagen mouse Ig primer set, which included six VH primer sets and seven VL primer sets. The amplified VL and VH PCR products were purified and cloned into Invitrogen pCR 2.1 Topo vectors, which readily ligate DNA sequences with T-A compatible ends. The transformed *E. coli* was plated on X-gal/Carb agar plates. The bacteria colonies containing PCR inserts appeared white. Random white colonies were selected for PCR to further verify the insertion.

Forty-eight white colonies from each transformation were selected for sequencing. Colonies were inoculated in 96-well plates with LB/Carb media and then stamped onto LB/Carb agar plates. The colonies which grew on the agar plates were sequenced using M13 forward primer. Based on the results of the sequences, primers were created that would allow PCR amplification of VL and VH adding restriction enzyme sites which are compatible to human IgG pOE expression vector. Restriction enzyme digestion and ligation were performed to clone VL and VH into the vector resulting in a chimeric antibody construct containing mouse variable region and human constant region. The plasmid DNA was transfected into 293F cells using 293 transfectin reagent. The IgG expression levels in the cell supernatants were estimated by Octet. IgG in the supernatant was purified using Protein-A columns. The purified IgG was analyzed on SDS-PAGE.

ELISA was used to test cross reactivity of lead clones. Cytokines tested include 11-2, IL-4, IL-7, IL-9, and IL-15. Maxisorp ELISA plate (NUNC) was coated with 2 µg/ml of different cytokines in PBS at 4° C. overnight. The plate was then blocked with 3% BSA in PBST (PBS+0.1% Tween) at room temperature for one hour. Purified lead clone IgGs were serially diluted in PBST+3% BSA and the mixture was then added to each ELISA plate well and further incubated at room temperature for half an hour. After washing, secondary antibody-HRP was added to each well for 1 hour. Wells were washed first with PBST and then with PBS and the TMB solution from Pierce was added to detect the secondary antibody. After 5' the reaction was stopped by the addition of 1N sulfuric acid. The plates were then read in an ELISA reader at 450 nm to detect the binding.

Humanization of Various Anti-IL-21 Murine mAbs

Murine mAb 9F11 was generated and characterized by MedImmune which shows desired biological activity with binding KD of 10 nM to IL-21. The humanization work was conducted at Shanghai ChemPartner Co. using the CDR grafting technology. Properties of the successfully humanized antibody candidates, 9F11-4, 9F11-6 and 9F11-11, were verified (results presented below). The V region sequences of 9F11 and the humanized 9F11 clones are shown in FIG. 1A.

The humanization of murine mAb 19E3 was done by grafting the CDRs of 19E3 onto selected human germline frameworks. The sequences of the heavy chain variable region (VH) and the light chain variable region (VL) of murine mAb 19E3 were compared with the human antibody germline sequences available in the public NCBI databases. Human acceptor frameworks were identified based on the highest sequence homology. When choosing an optimal acceptor framework, several other criteria were used, including matching of critical residues (Vernier zone, canonical class residues, and VH/VL interface residues), immunogenicity (germline frequency), stability, and expression. In this case, one germline family was identified as the acceptor framework for VH: VH1-46. The J-segment genes were compared to the parental sequences over Framework 4 and J-segments and JH4 was selected for the VH. This fully human germline acceptor template was named as Ha. To achieve the highest homology VL acceptor sequence, individual framework region from three different human germline were combined to design an optimal hybrid germline acceptor sequence. The human template chosen for the VL chain, named as K1, was a combination of O14 (Framework1), O18 (Framework2), L23 (Framework3) and JK1 (Framework 4). The framework homology between the murine sequence and human template was about 71% for VH and 79% for VL.

Critical mouse framework residues that were thought to affect CDR loops, stabilize structure of the variable regions and affect VH and VL inter-chain packing and/or interaction were identified and selectively introduced back into the human germline frameworks to best preserve the 19E3 binding epitope and affinity. In this case, mouse residues at 44V and 87F were mutated back in the VL chain human template as a second acceptor framework template, named K2. Alignment of the parental VL chain to these acceptor frameworks is shown in FIG. 1B.

Two additional human acceptor framework templates were designed for the VH chain as tools to identify the framework that could impact binding activity of 19E3 if the fully human acceptor template (Ha) lost binding affinity. One template, named Hb, was designed by fusing the murine framework 1 with the VH1-46/JH4 human template; another template, named Hc, was designed by fusing the murine framework 3 with the VH1-46/JH4 human template. Alignment of the parental VH chain to these acceptor frameworks is shown in FIG. 1B.

CDR residues as defined by Kabat were fused into the designed acceptor frameworks for both VH and VL for generating the humanized antibody. In total, three humanized VH genes (Ha, Hb and Hc) and two VL genes (K1 and K2) were synthesized by GeneART, then cloned into an IgG1 expression vector. A panel of humanized variants have been generated and characterized in biochemical and biological assays. HTRF epitope competition assay was developed to assess IL-21 binding activities of the humanized variants. Fully humanized VH template Ha exhibited comparable IL-21 binding activity to the murine 19E3 VH, as well as hybrid variants Hb and Hc. K2, the humanized VL template with two mouse residues at position 44V and 87F exhibited better binding activity than the fully humanized K1 variant. The resultant humanized variant (K2Ha) was shown to possess antigen-binding affinity and epitope specificity similar to 19E3. To minimize the mouse residue content in the best behaved humanized variant (K2Ha), mouse residue at 87F was replaced with the comparable human residue but not the 44V which was critical for retaining the binding activity to IL-21. A high risk N-linked glycosylation site (NYT) was identified in the 19E3 heavy chain at position 56 in CDR2 and was removed by replacing N with Q. The final humanized antibody (K44VHaN56Q) with only one mouse residue displayed indistinguishable binding activity comparing to mouse 19E3 and showed biological activities within 2-3 fold of 19E3 in all tested biological assays.

Murine mAb 9F11 showed desired biological activity with binding $K_D$ of 10 nM to IL-21. The humanization work was conducted at Shanghai ChemPartner Co. using the CDR grafting technology. Properties of the successfully humanized antibody candidates, 9F11-4, 9F11-6 and 9F11-11, were verified, showing that the antibodies fully retained binding affinity and biological activity to IL-21, compared to the parental murine 9F11. The V region sequences of 9F11 and the humanized 9F11 clones are shown in FIG. 1.

Properties of various anti-IL-21 antibodies provided herein are shown in Table 2.

TABLE 2

Exemplary Anti-IL-21 Antibodies

| Clone | Format | Description | Binding (ELISA) | Kd hu | Kd cy | Family X-reactivity |
|---|---|---|---|---|---|---|
| K44VHa-N56Q | hIgG1 | humanized variant of 19E3 | | 0.515 pM | 0.352 pM | IL-21 only |
| K44VHa6-N56Q | hIgG1 | humanized variant of 19E3 | | 0.245 pM | | IL-21 only |
| K2Ha-N56Q | hIgG1 | humanized variant of 19E3 | | 0.403 pM | | IL-21 only |
| 19E3 | mIgG1 | Murine Monoclonal Antibody | Yes | | | IL-21 only |
| 9F11 | hIgG1 | Murine Monoclonal Antibody | Yes | 9.99 pM | | IL-21 only |
| 9F11-4 | hIgG1 | humanized variant of 9F11 | | | | ND |
| 9F11-6 | hIgG1 | humanized variant of 9F11 | | | | ND |

TABLE 2-continued

Exemplary Anti-IL-21 Antibodies

| Clone | Format | Description | Binding (ELISA) | Kd hu | cy | Family X-reactivity |
|---|---|---|---|---|---|---|
| 9F11-11 | mIgG1 | humanized variant of 9F11 | | | | ND |
| 9H10 | mIgG1 | Murine Monoclonal Antibody | Yes | 108 pM | | IL-21 only |
| 8B6 | mIgG1 | Murine Monoclonal Antibody | Yes | | | IL-21 only |

ND: Not Done

Example 2

Binding Affinity of K44VHa-N56Q to Recombinant Human and Cynomolgus Monkey IL-21

This Example shows the determination of the solution-phase equilibrium binding constants ($K_D$) for the interaction of K44VHa-N56Q with human and cynomolgus monkey IL-21 proteins. The equilibrium dissociation constant ($K_D$) for the interaction of K44VHa-N56Q with recombinant human (hu) and cynomolgus monkey (cyno) IL-21 were measured using a KinExA (Kinetic Exclusion Assay) 3000 platform (Sapidyne, Boise, Id.). Separate 50 mg quantities of Azlactone beads (Thermo Scientific, Rockford, Ill.) were coated with huIL-21 (obtained from Protein Sciences/ADPE) or cynoIL-21 (obtained from Protein Sciences/ADPE) at concentrations of 75 or 150 µg/mL according to the instrument manufacturer's instructions. The beads were washed and blocked in 1 M Tris buffer, pH 8 (Invitrogen, Carlsbad, Calif.), containing 10 mg/mL bovine serum albumin (BSA, Sigma-Aldrich, St. Louis, MPO) and stored at 4° C. until used. Batch volumes of K44VHa-N56Q were prepared at concentrations of 500 fM and 50 pM (500 fM and 50 pM K44VHa-N56Q series, respectively) in sample buffer (phosphate-buffered saline (PBS, Invitrogen), pH 7.4, 0.1% BSA, 0.02% sodium azide ($NaN_3$, Sigma-Aldrich)); each was dispensed into 2 separate sets of 13 tubes (1 for each series). Human or cynomolgus monkey IL-21 was added into 1 tube from each series at a concentration of either 4 nM (50 pM K44VHa-N56Q) or 100 pM (500 fM K44VHa-N56Q series), then serially diluted across 11 of the remaining tubes, leaving 1 sample tube in each series as the K44VHa-N56Q, receptor-only control. The final human or cynomolgus monkey IL-21 concentrations in the individual sample mixtures ranged from 1.95 fM to 100 pM (500 fM K44VHa-N56Q), and 78.1 fM to 4 nM (50 pM K44VHa-N56Q). These sample mixtures were equilibrated at room temperature for 2 to 7 days, and analyzed on the KinExA platform. The IL-21-coated Azlactone bead slurries were diluted to 30 mL with instrument buffer (PBS, pH 7.4, 0.02% NaN3) in a bead vial and affixed to the KinExA instrument. A user-defined timing program was used to sequentially transfer the IL-21/Azlactone beads to a capillary flow cell in the instrument, and individual sample mixtures were injected over the IL-21-coated beads. Unbound sample solution was removed by washing the beads with instrument buffer. A 1- or 2-µg/mL solution of the DyLight649-labeled, goat-anti-huIgG(H+L) secondary reagent (Thermo Scientific) was passed over the beads to detect receptor (K44VHa-N56Q) that remained bound to the IL-21-coated beads. The beads were again washed with instrument buffer to remove excess (unbound) label. The amount of fluorescence that remained associated with the beads was measured, and the signal was converted to percent free receptor (K44VHa-N56Q). In between samples, the bead pack was flushed from the flow cell and replenished with fresh IL-21-coated Azlactone beads in preparation for the next sample. Once the data had been collected for all samples in each series (500 fM and 50 pM K44VHa-N56Q), an isotherm was generated, which plotted the amount of free K44VHa-N56Q detected at each concentration of IL-21. The resulting 2 binding curves were then evaluated in a dual curve analysis using the instrument's evaluation software (KinExA Pro Software, v. 2.0.1.26, Sapidyne) from which individual $K_D$S for each interaction were derived.

Figure 2A:
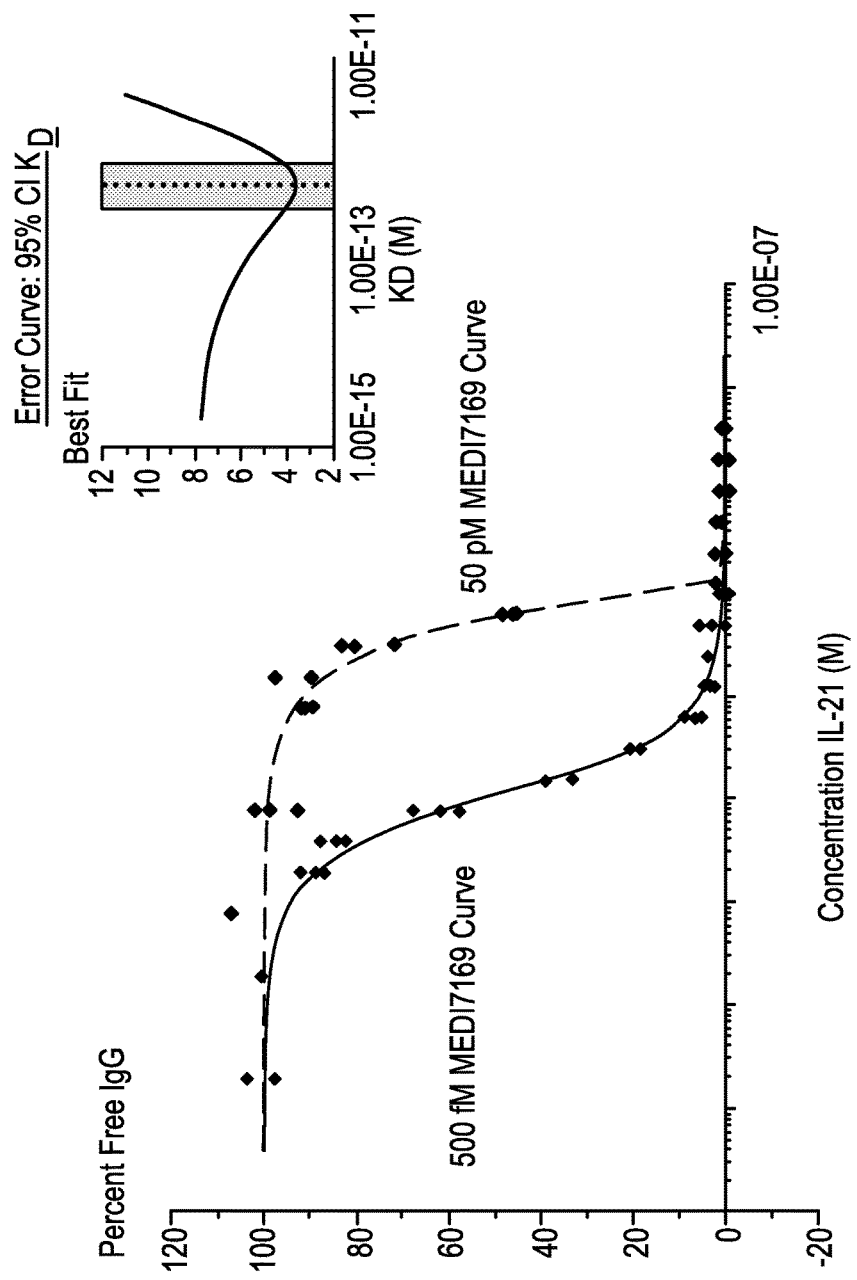

The binding of K44VHa-N56Q to human and cynomolgus monkey IL-21 was measured by KinExA. K44VHa-N56Q was prepared in 2 concentration series: 500 fM and 50 pM, and human IL-21 or cynomolgus monkey IL-21 protein were serially diluted across each series. Once equilibrium was reached, the KinExA instrument was used to measure the concentration of free K44VHa-N56Q that remained in each of the sample mixtures. This was done by recording the amount of fluorescence that remained associated with IL-21-coated beads after samples of each mixture were passed over the beads, and then exposed to a fluorescently labeled, anti-IgG reagent. A plot of the amount of free K44VHa-N56Q recorded versus huIL-21 or cynoIL-21 protein concentration was made, and the KinExA platform's evaluation software was used to fit each data set to a one-site affinity model. The KinExA software globally fit both binding curves (500 fM and 50 pM IgG) in a dual-curve analysis (FIGS. 2A and 2B, respectively, returning optimal solutions for several parameters simultaneously and calculating the true solution-phase binding constant. Under these conditions, the $K_D$ for the binding of K44VHa-N56Q to huIL-21 protein was calculated to be 515 fM (95% CI for $K_D$: 279 to 844 fM), while the binding or K44VHa-N56Q to cynoIL-21 protein was calculated to be 352 fM (95% CI for $K_D$: 134 to 685 fM).

K44VHa-N56Q was demonstrated to weakly bind to murine IL-21 with µM affinity, as measured on a KinExA platform.

Example 3

Mechanism of Action Studies for Anti-IL-21 Monoclonal Antibodies

Anti-IL-21 Clones Block IL-21 Induced Phosphorylation of STAT3

The ability of purified anti-IL-21 antibodies to inhibit human and cyno IL-21-induced phosphorylation of STAT3 (pSTAT3) was determined as described below.

Briefly, total human peripheral blood mononuclear cells (PBMCs) were isolated from CPT tubes (BD Vacutainer)

following centrifugation according to the manufacturer's instructions. Anti-IL-21 antibodies were pre-incubated with human or cyno IL-21 (20 pM) in 96-well round bottom plates for 60 minutes at 37 degrees. Following this incubation, PBMCs ($0.4 \times 10^6$ per well) were quickly added to each well and were incubated with the IL-21/IgG for 15 minutes at 37 degrees. After stimulation the cells were fixed for 10 minutes (at 37 degrees) with 100 µl/well pre-warmed Lyse/Fix Buffer (BD Phosflow) followed by permeabilization on ice for 30 minutes with 225 µl/well Perm Buffer III (BD Phosflow). Cells were washed twice (PBS/2% BSA) and stained with anti-pSTAT3 (pY705, BD Phosflow) for 30 minutes at room temperature. Cells were washed with stain buffer and were analyzed on an LSR II flow cytometer (BD Biosciences) using FACSDiva software.

Stimulation with human and cyno IL-21 as described induced a 3-5-fold increase in levels of pSTAT3 in total human PBMCs (FIG. 3A). Representative graphs demonstrating inhibition of IL-21-induced upregulation of pSTAT3 by anti-IL-21 antibodies are shown in FIG. 3B. All clones tested reached 100% inhibition in this assay. IC50 values of anti-IL-21 clones in the pSTAT3 assay are summarized in Table 3. These data show that the anti-IL-21 antibodies described are able to inhibit early signaling events downstream of the IL-21R.

TABLE 3

IC50 values of anti-IL-21 antibodies in the pSTAT3 assay
IC50 of indicated clones in pSTAT3 assay

| Clone | human IL-21 | cyno IL-21 |
|---|---|---|
| K2Ha-N56Q | 18.7 +/− 5.1 pM | 15.63 +/− 5.4 pM |
| K44VHa-N56Q | 17.2 +/− 7.8 pM | 19.28 +/− 7.8 pM |
| K44VHa6-N56Q | 5.5 +/− 1.7 pM | 9.75 +/− 3.14 pM |
| 19E3 | 3.15 +/− 1 pM | 5.99 +/− 1.8 pM |
| 9F11 | 21.73 +/− 6.03 pM | 83.17 +/− 335.1 pM |
| 9H10 | 328.2 +/− 101 pM | 160.5 +/− 141 pM |
| 8B6 | 114.9 +/− 71.2 pM | 228.2 +/− 223 pM |
| 9F11-4 | 12.05 pM | 52.18 pM |
| 9F11-6 | 13.17 pM | 50.77 pM |
| 9F11-11 | 13.57 pM | 45.88 pM |

K44VHa-N56Q has been shown to weakly bind to murine IL-21. Stimulation of mouse splenocytes with murine IL-21 induced a 4-fold increase in intracellular levels of phosphorylated STAT3. K44VHa-N56Q was not able to inhibit phosphorylation of STAT3 induced by murine IL-21. These data suggest that K44VHa-N56Q does not neutralize the bioactivity of murine IL-21.

IL-21 is a member of the $\gamma_c$ receptor cytokine family which utilizes the common gamma chain in concert with a specific receptor(s) to mediate biologic activity. Human blood lymphocytes were stimulated with $\gamma_c$ chain utilizing IL-2, IL-4, IL-7, IL-15, or IL-21 cytokines in the presence or absence of K44VHa-N56Q or a control human IgG1-YTE antibody. Downstream signaling was measured by assessing the phosphorylation of STAT molecules appropriate for each cytokine. K44VHa-N56Q had no effect on downstream signaling of related IL-2, IL-4, IL-7, or IL-15 cytokines. These data show that K44VHa-N56Q acts specifically to neutralize the IL-21 pathway in human cells.

IL-21 signaling through its cognate receptor leads to the activation and phosphorylation of STAT3. Data described herein demonstrate that K44VHa-N56Q can inhibit upregulation of pSTAT3 in response to both human and cyno IL-21, but not mouse IL-21. Furthermore, this inhibition is specific for IL-21, as K44VHa-N56Q did not affect activation of STAT molecules downstream of related $\gamma_c$ cytokine receptors such as receptors for IL-2, IL-4, IL-7, and IL-15. Accordingly, K44VHa-N56Q is a potent and specific inhibitor of IL-21R signaling events.

IL-21 Blockade Suppresses IFNγ Production by NK-92 Cells

The effect of purified anti-IL-21 antibodies on IL-21 induced IFNγ production by NK-92 cells was assessed as follows.

NK-92 cells were grown in complete growth media which consisted of MEM alpha Glutamax base media supplemented with sodium bicarbonate (1.5 g/L), inositol (0.2 mM, Sigma Aldrich), 2-mercaptoethanol (0.1 mM), folic acid (0.02 mM, Sigma Aldrich), recombinant IL-2 (100 U/ml, R&D Systems), horse serum (12.5%), and fetal bovine serum (12.5%). All reagents were purchased from Invitrogen unless otherwise indicated. Cells were washed and resuspended in media that did not contain IL-2 for 16-24 hours prior to stimulation with IL-21. To assess the potency of the anti-IL-21 clones, antibodies were pre-incubated with human or cyno IL-21 (200 pM) in 96-well flat bottom plates for 60 minutes at 37 degrees. $0.5 \times 10^5$ NK-92 cells were then added to the plate and incubated at 37 degrees for 24 hours. IFNγ production was quantified in the supernatant using an MSD human IFNγ single-plex assay according to the manufacturer's instructions (Meso Scale Discovery).

Figure 4A:
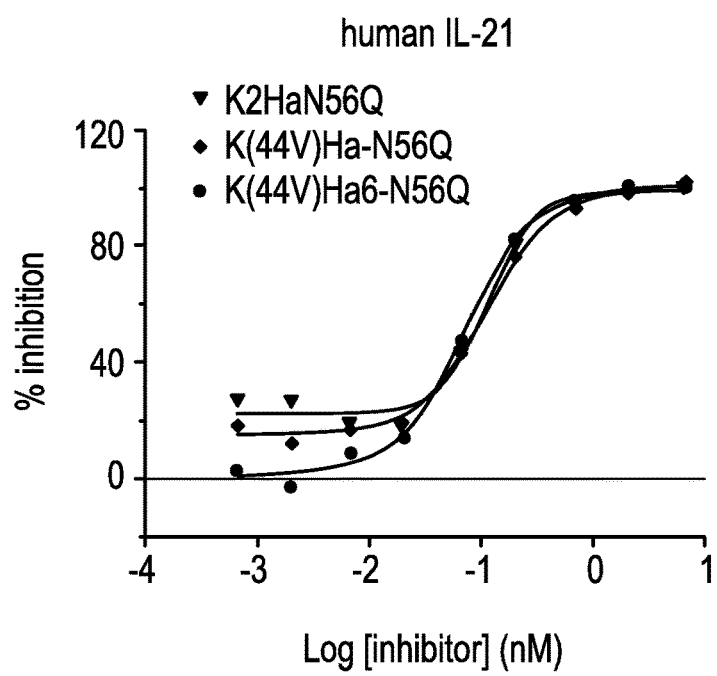
FIG. 4 shows the inhibition of human (FIG. 4A) and cynomolgus monkey IL-21 (FIG. 4B) induced IFNγ by NK-92 cells.
Figure 4B:
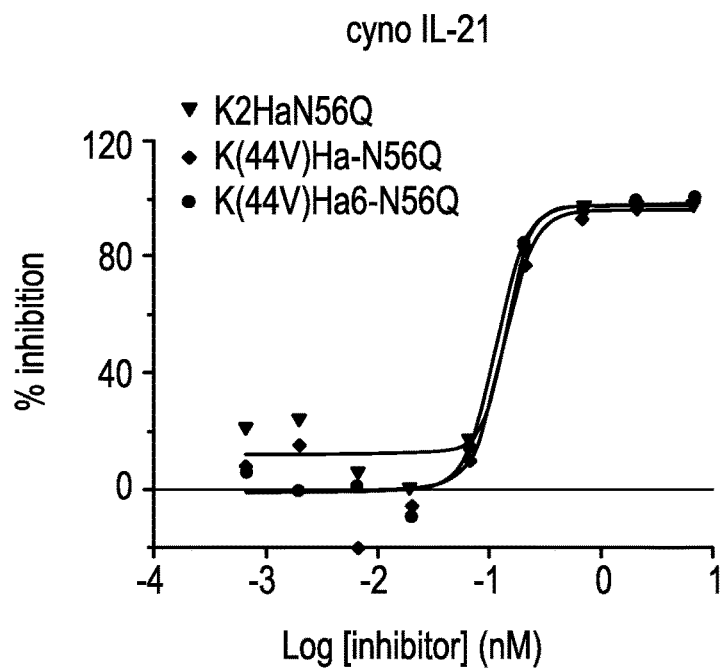

The ability of anti-IL-21 clones to inhibit human and cyno IL-21 induced IFNγ by NK-92 cells is represented in FIG. 4. Clones K2Ha-N56Q, K(44V)Ha-N56Q, and K(44V)Ha6-N56Q were able to completely inhibit IFNγ production in these cultures, with similar potency against human and cyno IL-21. A summary of IC50 values of clones assessed in the NK-92 cell assay is provided in Table 4. These data demonstrate that the anti-IL-21 antibodies tested modulate the activity of NK-92 cells as demonstrated by a complete block in IFNγ production at 24 hours.

TABLE 4

IC50 values of anti-IL-21 antibodies in the NK-92 assay
IC50 of indicated clones in NK-92 cell assay

| Clone | human IL-21 | cyno IL-21 |
|---|---|---|
| K2Ha-N56Q | 99 +/− 36.2 pM | 83.4 +/− 40 pM |
| K44VHa-N56Q | 92.7 +/− 38 pM | 80.8 +/− 37.8 pM |
| K44VHa6-N56Q | 54.8 +/− 14.9 pM | 60.3 +/− 38.1 pM |
| 19E3 | 41 +/− 2 pM | 37 +/− 6 pM |
| 9F11 | 462 +/− 1 pM | 867 +/− 66 pM |
| 9H10 | 20.21 nM | 3.43 nM |
| 8B6 | 943.9 pM | 770.7 pM |

Plasma Cell Differentiation Induced by Exogenous IL-21 is Inhibited by Anti-IL-21 Clones In order to determine the effect of the anti-IL-21 antibodies on B cell activity, a plasma cell differentiation assay was performed.

Human PBMCs were isolated from CPT tubes (BD Vacutainer) following centrifugation according to the manufacturer's instructions. B cells were negatively selected using MACS cell separation reagents (Human B cell isolation kit II, Miltenyi Biotec). Routine purity for B cells using this technique was >97%. Of note, total B cell preparations isolated using this method contain populations of both naïve and memory B cells, but PCs were excluded due to expression of CD43, which is targeted by the antibody selection cocktail of the MACS kit. Culture medium for these experiments was RPMI 1640 (Invitrogen) supplemented with 10% FCS, penicillin-streptomycin (100 units/ml penicillin, 100

µg/ml streptomycin), 2-mercaptoethanol (55 µM), L-glutamine (2 mM), and HEPES (5 mM). Anti-IL-21 antibodies were pre-incubated in 96-well round bottom plates with the stimulation cocktail which included human or cyno IL-21 (2 nM), anti-CD40 (0.1 µg/ml, goat IgG, R&D Systems), and anti-IgM F(ab')2 (5.0 µg/ml, Jackson ImmunoResearch Laboratories) for 60 minutes at 37 degrees. 0.5-1.0×10$^5$ B cells were then added to the plate for a final volume of 150 µl.

Following 6 days of stimulation, the cells were stained and analyzed using flow cytometry to quantify the frequency of plasma cells in culture. Cells were washed (PBS/2% FBS) and stained for 30 minutes at 4 degrees with anti-IgD (FITC or PE); anti-CD38 (allophycocyanin, clone HB7) (BD Pharmingen) and were analyzed on an LSRII flow cytometer using FACSDiva Software. Additionally, supernatants were harvested and Ig production was quantified by ELISA. Briefly, 96-well flat bottom plates were coated overnight at 4° C. with 5 µg/ml of goat anti-human IgG diluted in PBS (Bethyl Laboratories). Plates were washed and blocked with 0.2% BSA in PBS. Supernatants were diluted and incubated on plates overnight. Bound Ig was detected with goat anti-human IgG-alkaline phosphatase (0.2 µg/ml, Bethyl Laboratories) diluted in blocking buffer. Plates were developed with SigmaFast p-Nitrophenyl phosphate tablets (Sigma Aldrich) and specific absorbance was measured at 405 nm using a SpectraMax plate reader (Molecular Devices).

Stimulation of human B cells as described above with either human or cyno IL-21 resulted in the generation of an IgD$^-$ CD38$^{hi}$ PC population (FIGS. 5A and 5B). Several clones including 19E3.1, 9F11.1, and 9H10.1 were able to completely inhibit PC differentiation under these conditions (FIGS. 5A and 5B). Clone 8B6.1 inhibited PC differentiation induced by cyno but not human IL-21. IC50 values for anti-IL-21 clones are summarized in Table 5. Additionally, under control conditions, stimulation with IL-21, anti-CD40 and anti-IgM resulted in Ig production in the range of 30-40 µg/ml by day 6 (FIG. 5C). Clones 19E3.1 and 9F11.1 inhibit Ig secretion by human B cells in a dose dependent manner (FIG. 5C). Clone 19E3.1 was able to inhibit IgG production in response to both human and cyno IL-21 by >99%, while 9F11.1 inhibited IgG production by human and cyno IL-21 by 97% and 79% respectively. Cumulatively, these data suggest that the anti-IL-21 clones described are able to significantly inhibit human Plasma cell differentiation and Ig secretion induced by exogenous human and cyno IL-21.

TABLE 5

IC50 values for anti-IL-21 antibodies in the plasma cell differentiation assay
IC50 of indicated clones in PC differentiation assay

| Clone | human IL-21 | cyno IL-21 |
| --- | --- | --- |
| K2Ha-N56Q | 618 +/- 155 pM | 1.32 +/- 0.39 nM |
| K44VHa-N56Q | 777 +/- 201 pM | 1.06 +/- 0.15 nM |
| K44VHa6-N56Q | 573 +/- 385 pM | 659.3 +/- 124 pM |
| 19E3 | 1.53 nM | 775 pM |
| 9F11 | 47.3 +/- 32.6 nM | 74 +/- 81 nM |
| 9H10 | 115.5 nM | 29.8 nM |
| 8B6 | >200 nM | 8.9 nM |

Anti-IL-21 Clones Inhibit PC Differentiation Induced by Activated CD4+ T Cells

Anti-IL-21 clones were tested for their ability to block plasma cell differentiation induced by activated CD4+ T cells in a co-culture assay as described below.

Human PBMCs were isolated from CPT tubes (BD Biosciences) following centrifugation. B cells and CD4+ T cells were negatively selected using MACS cell separation reagents (Miltenyi Biotec). Routine purity for total B cells and CD4+ T cells was >97%. CD4+ T cells were mitomycin-C treated (30 µg/ml, Sigma Aldrich) for 30 minutes at 37° C. then washed and rested in complete media at 37° C. for an additional 30 minutes. 1.0×10$^5$ mitomycin-C treated CD4+ T cells and 0.5×10$^5$ purified B cells (per well) were co-cultured in a final volume of 200 µl with anti-CD3/anti-CD28 beads (5:1 T cell to bead ratio). Culture medium for all experiments was RPMI 1640 (Invitrogen) supplemented with 10% FCS, penicillin-streptomycin (100 units/ml penicillin, 100 µg/ml streptomycin), 2-mercaptoethanol (55 µM), L-glutamine (2 mM), and HEPES (5 mM). Anti-IL-21 antibodies were added to the cultures at a concentration of 0-200 nM. Following 7 days of culture, plasma cells were quantified using flow cytometry. Cells were washed (PBS/ 2% FBS) and stained for 30 minutes at 4 degrees with anti-IgD (FITC or PE); anti-CD38 (allophycocyanin, clone HB7) (BD Pharmingen) and were analyzed on an LSRII flow cytometer using FACSDiva Software. All conditions were collected for the same time, thus the number of events displayed is reflective of relative cell number. However, total cell numbers were determined using AccuCount Particles (Spherotech).

Co-culture of B cells with activated CD4+ T cells resulted in the emergence of an IgD$^-$ CD38$^{hi}$ PC population, with 68.5% of the CD19+ cells expressing this PC phenotype by day 7 (FIG. 6A). Addition of 19E3.1 or 9F11.1 inhibited PC differentiation in a dose dependent manner with each achieving a maximal inhibition of 80% and 78%, respectively (FIGS. 6B and 6C). These data suggest that anti-IL-21 clones can largely block plasma cell differentiation induced by de novo IL-21 production from activated T cells.

Anti IL-21 Clone Inhibits Naïve CD4+ T-cell Expansion

IL-21 has been shown to support CD4+ T-cell proliferation under suboptimal priming conditions. Human naive CD4+ T cells were purified and stimulated in vitro with anti-CD3 and IL-21 in the presence or absence of parental antibody 19E3.1. Proliferation was assessed by measuring the accumulation of ATP after four days in culture. As previously reported, the amount of ATP detected is directly proportional to the number of metabolically active cells in culture. 19E3.1 blunted IL-21-induced proliferation (average IC50=61.02 pM for two donors) in a dose-dependent manner. These data show that the K44VHa-N56Q (MEDI7169) parental antibody 19E3.1 inhibits IL-21-driven proliferation of human naive CD4+ T-cells (FIG. 7).

Pharmacokinetics

Pharmacokinetics (PK) of K44VHaN56Q, a YTE antibody, was evaluated in three studies using monkeys as an animal model, which can predict human PK with reasonable accuracy (Oitate et al, Drug Metab. Pharmacokinet. 26 (4): 423-430 (2011)). Clearance is a major PK parameter for human PK prediction scaled from animal data; a smaller CL value suggests that a molecule can stay longer in the body. CL values for K44VHaN56Q in monkeys range from 1.08 to 4.37 mL/d/kg. Typical therapeutic antibodies such as Bevacizumab (Avastin®), Daclizumab (Zenapax®), Infliximab (Remicade®), and Rituximab (Rituxan®) are associated with respective CL values as 5.78, 5.30, 11.5, and 17.0 (mL/d/kg) (Dong et al, Clin Pharmacokinet. 50(2):131-142 (2011). Monkey body weight was assumed to be 3 kg). These CL values are greater than the estimated for K44VHaN56Q. Therefore, K44VHaN56Q is expected to stay in body longer than a typical therapeutic antibody.

Example 4

Prevention of Graft-Versus-Host Disease (GVHD) Using Anti-IL-21 Monoclonal Antibodies Xenogeneic GVHD Mouse Model GVHD develops when transferred (donor) T cells perceive foreign antigens presented by host (recipient) MHC/HLA molecules. NOD/SCID/IL-2 receptor γ chain deficient (NSG) mice lack mature T and B cells, functional NK cells, and macrophages. These mice demonstrate decreased cytokine signaling due to loss of the γc receptor.

In a xenogenic model of GVHD, human PMBCs are transferred to NSG mouse recipients. Since the mice are immunocompromised, the human cells are not rejected by the mouse immune system. The human cells recognize the mouse environment as foreign and become activated and proliferate. The activated human cells produce a "cytokine storm," leading to a severe immunoreactive cascade, affecting liver, gastrointestinal tract, and skin, ultimately resulting in death of the animal. A large number of cells capable of producing IL-21 can be isolated from the blood of GVHD mice.

Thirty-five female NSG mice (NOD.Cg-Prkdcscid Il2rgtm1Wjl/SzJ; The Jackson Laboratories, Bar Harbor, Me.) were used in the prophylactic study. Mice were 5-7 weeks old and weighed 16.8-22.4 grams at the start of the study.

Isolation of Human Peripheral Blood

Human blood was collected from two healthy donors into Cell Preparation Tubes (CPT) (Becton Dickinson, San Jose, Calif.) containing sodium heparin. Mononuclear cells were isolated from CPT tubes according to the manufacturer's instructions. Briefly, tubes were centrifuged at room temperature for 25 minutes at 1700×g. Following centrifugation, mononuclear cells were harvested. Cells were washed twice in PBS by centrifuging for 10 minutes at a relative centrifugal force of 400×g. The cells were then counted and resuspended in the appropriate amount of PBS and kept at room temperature until injections (immediately following final wash).

Antibodies

A human IgG1κ-YTE (NIP-228-YTE; MedImmune, Cambridge, UK) was used as a Control mAb in this example. The control mAb was aliquoted and frozen as stock solution at −80° C. Formulation buffer was 25 mM histidine, 7% sucrose, 0.02% (w/v) polysorbate 80, at pH 6.0. The dosing solution was prepared by diluting an aliquot of the stock solution (60.6 mg/mL) with phosphate-buffered saline PBS to 1 mg/mL. Working preparations were stored at 4-8° C.

K44VHa-N56Q (MEDI7169) was stored at −80° C. as aliquoted and frozen stock solution. Formulation buffer was 25 mM histidine, 205 mM sucrose, 0.02% (w/v) polysorbate 80, at pH 6.0. The dosing solution was prepared by diluting an aliquot of the stock solution (47.6 mg/mL) with PBS to 1 mg/mL. Working preparations were stored at 4-8° C.

Injection of Human Cells, Treatments, and Assessment of GVHD

Dosing was performed as shown in Table 6. Briefly, $12.71 \times 10^6$ purified human PBMC's from Donor 1 or $13.46 \times 10^6$ purified human PBMC's from Donor 2 were injected IP into 5-7 week old female NSG mice on Day 0. Two hundred micrograms (in 200 μL volume) K44VHa-N56Q (MEDI7169), Control mAb, or an equal volume of PBS (vehicle) alone was administered IP, three times a week starting on Day −1, prior to injecting human PBMCs.

TABLE 6

Group Designation and Dose Levels in Prophylactic Study

| Group | # of animals | Donor PBMC and Treatment | Days of dosing | Dose (μg) | ROA |
|---|---|---|---|---|---|
| Naive | 5 F | None | N/A | N/A | N/A |
| Vehicle (Donor 1) | 1 F | Donor 1 ($12.71 \times 10^6$) and PBS | Mo, W, Fr Day −1 to Day 31 | 0 | IP |
| Control mAb (Donor 1) | 5 F | Donor 1 ($12.71 \times 10^6$) and Control mAb | Mo, W, Fr Day −1 to Day 31 | 200 | IP |
| K44VHa-N56Q (MEDI7169) (Donor 1) | 5 F | Donor 1 ($12.71 \times 10^6$) and K44VHa-N56Q (MEDI7169) | Mo, W, Fr Day −1 to Day 31 | 200 | IP |
| Vehicle (Donor 2) | 5 F | Donor 2 ($13.46 \times 10^6$) and PBS | Mo, W, Fr Day −1 to Day 44 | 0 | IP |
| Control mAb (Donor 2) | 5 F | Donor 2 ($13.46 \times 10^6$) and Control mAb | Mo, W, Fr Day −1 to Day 44 | 200 | IP |
| K44VHa-N56Q (MEDI7169) (Donor 2) | 5 F | Donor 2 ($13.46 \times 10^6$) and K44VHa-N56Q (MEDI7169) | Mo, W, Fr Day −1 to Day 44 | 200 | IP |

F = female;
Fr = Friday;
IP = intraperitoneal;
mAb = monoclonal antibody;
Mo = Monday;
N/A = not applicable, as animals were not dosed;
PBMC = peripheral blood mononuclear cells;
PBS = phosphate- buffered saline;
ROA = route of administration;
W = Wednesday;

Body weight was individually measured throughout the study, at least once weekly. Mice were euthanized when they were determined to have lost 20% body weight or if the mouse was emaciated/moribund or otherwise in pain or distress. Death and humane euthanasia were used synonymously for the purposes of tracking survival.

Assessment of T-cell Number and Phenotype by Flow Cytometry

Mice were bled from the retro-orbital sinus into heparin microtainer tubes. In all experiments at all time points, 100 μL of blood was utilized. A red blood cell lysis step was performed using ACK lysing buffer (Life Technologies, Grand Island, N.Y.), the remaining cells were incubated with TruStain Fc blocker (BioLegend, San Diego, Calif.), diluted 1:4, for 10 minutes, then stained for 30 minutes at 4° C. with the following antibody cocktail to visualize CD4 and CD8 T cells: V500-conjugated anti-human CD45 (clone HI130; BioLegend, San Diego, Calif.), AF700-conjugated anti-human CD4 (clone RPA-T4; BioLegend, CA), and BV711-conjugated anti-human CD8 (clone RPA-T8; BioLegend, San Diego, Calif.). Samples were washed, fixed in 2% paraformaldehyde, and run on a Becton Dickinson LSR II flow cytometer using FACSDiva software. Samples were analyzed using FlowJo software (version 9). Human cells were identified by those that expressed the human CD45 antigen. Stained blood (100 μL) for all conditions were collected on LSRII for the same volume, thus the number of events displayed is reflective of relative cell number for the different treatments.

Assessment of Human Cytokines in Serum from Treated Mice by Multiplex ELISA

Longitudinal serum samples were collected and analyzed using a human Th17 multiplex kit (magnetic bead, premixed) (Merck Millipore, Billerica, Mass.) with a Luminex 200 analyzer; manufacturer's instructions were followed.

GraphPad Prism (version 6.0d for Mac OS X) was utilized. Serum cytokine results from K44VHa-N56Q (MEDI7169) treated mice were compared to that of Control mAb treated mice (Donor 1) or that of Control mAb and PBS (vehicle) treated mice combined (Donor 2). These data were analyzed using unpaired t-tests with Welch's correction, unless the variances were determined to be significantly different by F-test, and then Mann Whitney tests were performed. P<0.05 for all significant differences.

Figure 8A:
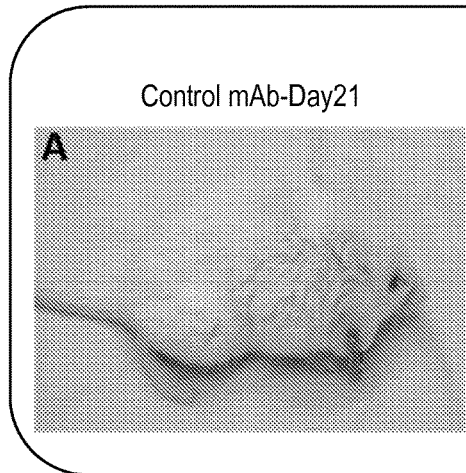
Figure 8C:
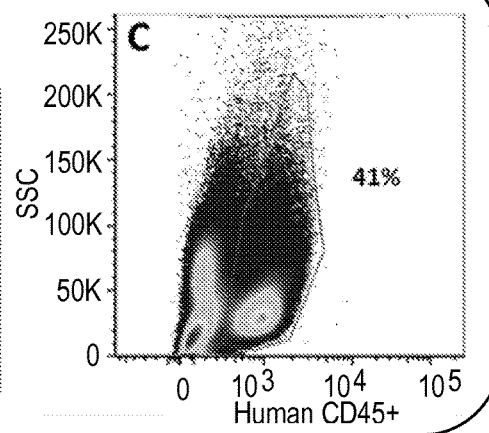
Figure 8B:
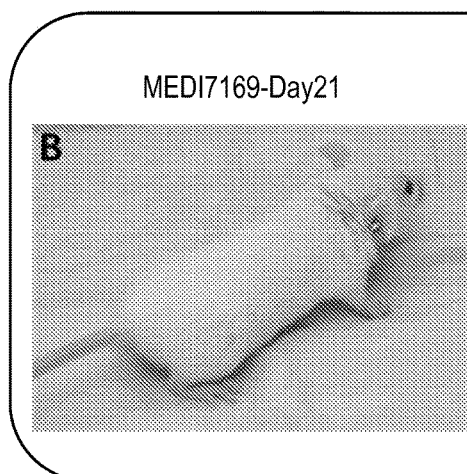
Figure 8D:
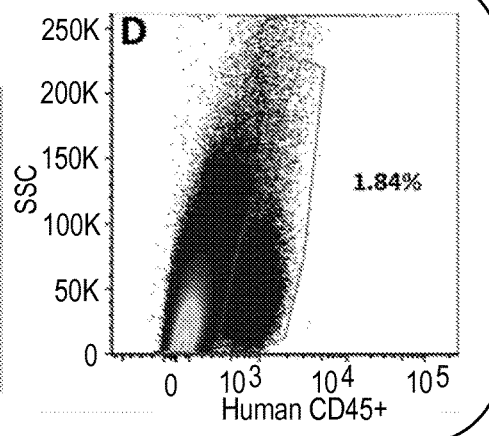
Figure 8E:
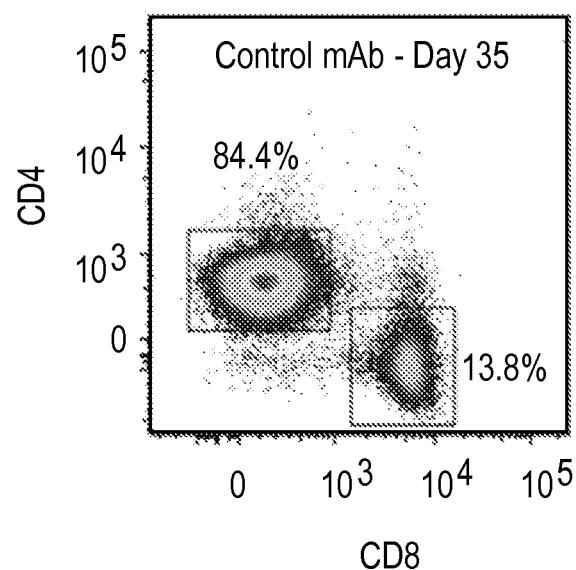
Figure 8F:
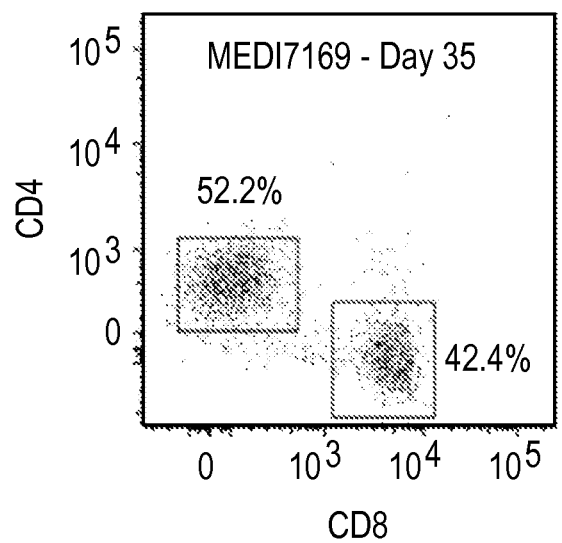

K44VHa-N56Q (MEDI7169) Inhibits Xenogeneic GVHD-induced Wasting and T-cell Expansion IL-21 has been reported to impact T-cell function. Thus, the ability of K44VHa-N56Q (MEDI7169) to inhibit xenogeneic GVHD, which is largely mediated by CD4+ T cells was investigated. Human PBMCs were injected into immunocompromised NSG mice, as described above, and a wasting disease was noted by Day 21 in mice that received Control mAb (human IgG1 mAb) (FIG. 8A) or PBS Vehicle. Mice that received 200 µg of K44VHa-N56Q (MEDI7169) three times a week starting at Day −1 appeared healthy (FIG. 8B) and could not be distinguished from control mice that received no human cells. Analysis of the blood revealed that in mice who received Control mAb (or PBS), human CD45+ cells had expanded (FIG. 8C). In comparison, mice that received K44VHa-N56Q (MEDI7169) had significantly reduced human CD45+ cells present in the blood (FIG. 8D). In Control mAb (and PBS) treated mice, this expansion of human CD45+ cells consisted mostly of CD4 positive cells (FIG. 8E), whereas the percent of CD4 positive cells was greatly reduced in K44VHa-N56Q (MEDI7169) treated mice, such as noted on Day 35 (FIG. 8F). These results are consistent with K44VHa-N56Q (MEDI7169) inhibition of expansion of human CD4+ T cells following transplantation of human PBMCs into immunocompromised mice.

When mice were followed over time, animals that received PBS vehicle or Control mAb were found to have a steady increase in the numbers of human CD45+ cells. However, these cells did not expand in mice that received K44VHa-N56Q (MEDI7169) (FIG. 9). Importantly, approximately 3 weeks following K44VHa-N56Q (MEDI7169) withdrawal, human CD45+ cells were found to initiate expansion, which then again declined upon resuming treatment (FIG. 9). These data demonstrate that K44VHa-N56Q (MEDI7169) can significantly inhibit T-cell expansion, which is reversible upon withdrawal.

GVHD-Induced Weight Loss and Death are Prevented by K44VHa-N56O (MEDI7169)

Body weight loss and survival were monitored in mice that received either no human cells (naive), or that received human PBMCs with PBS vehicle, Control mAb, or K44VHa-N56Q (MEDI7169) started one day (Day −1) before the mice received human PBMCs. Mice that received PBS or Control mAb were found to rapidly lose weight (FIG. 10A) and either died or were euthanized when body weight declined by 20%. All mice (n=16) that were injected with PBS or Control mAb in two separate studies either died or were euthanized by study day 37 after receiving human PBMCs (FIG. 10B). In contrast, all mice (n=10) that received K44VHa-N56Q (MEDI7169) survived and remained healthy until K44VHa-N56Q (MEDI7169) was withdrawn (FIG. 10B). In one experiment, mice remained healthy for approximately 20 days after K44VHa-N56Q (MEDI7169) was withdrawn, and then rapidly declined and died or were euthanized shortly after study Day 31 (FIG. 10B). In a separate study utilizing a second donor's human PBMCs, mice remained viable for approximately 40 days after K44VHa-N56Q (MEDI7169) was stopped. These data demonstrate that K44VHa-N56Q (MEDI7169) protects against lethality, which is reversible when K44VHa-N56Q (MEDI7169) is withdrawn.

K44VHa-N56O (MEDI7169) Inhibits Production of Several Cytokines and is Reversible Sera from mice injected with Donor 2 (FIG. 11) or Donor 1 (FIG. 12) cells, was collected at various time points, and analyzed for expression of 25 cytokines using Millipore's MILLIPLEX MAP system. Over half of the cytokines examined were below the level of detection. For the cytokines that were detectable, K44VHa-N56Q (MEDI7169) induced a significant decrease in GM-CSF, IL-10, and TNF in two separate experiments. In one experiment IFNγ was significantly decreased and trended down in a second experiment. IL-17A and IL-9 were found to be significantly decreased in one of two experiments. In both experiments, IL-5 was found to be significantly increased (FIG. 11). Complete blood counts (CBC) were performed using the Sysmex XT-2000iv hematology analyzer, and importantly, an increase of eosinophils was not noted in the mice with increased IL-5. IL-21 was found to be increased in both experiments. Increased IL-21 is consistent with that obtained in a toxicity study in cynomolgus monkeys in which the increased IL-21 was a reflection of the amount of circulating drug that was binding to and neutralizing the cytokine.

As shown in FIG. 9, K44VHa-N56Q (MEDI7169) inhibited CD4+ T cell expansion, which was reversible when drug was withdrawn. This was confirmed in a second study (FIG. 12). It is noteworthy that following cell expansion, several cytokines also increased, including TNF, IFNγ, and IL-10 (FIG. 12). These data show that and anti-IL-21 antibody, namely, K44VHa-N56Q (MEDI7169) inhibits T-cell expansion and cytokine production, which are both reversible when K44VHa-N56Q (MEDI7169) is stopped.

Example 5

Treatment of Graft-Versus-Host Disease (GVHD) Using Anti-IL-21 Monoclonal Antibodies Experimental Design Twenty female NSG mice (NOD.Cg-Prkdcscid Il2rgtm1Wjl/SzJ; The Jackson Laboratories, Bar Harbor, Me.) were used in the therapeutic study. Mice were 8 weeks old and weighed 18.0-22.3 grams at the start of the study.

Human blood was collected and prepared as described above in Example 4.

Control and test mAbs were obtained, handled, and stored as described above in Example 4.

Dosing was performed as shown in Table 7. Briefly, 12×10$^6$ purified human PBMC's from Donor 1 were injected IP into 8 week old female NSG mice on Day 0. Two hundred micrograms (in 200 µL volume) K44VHa-N56Q (MEDI7169) or control mAb were injected IP three times a week starting on Day 7. Another group was injected with K44VHa-N56Q (MEDI7169) (200 µg in 200 µL) IP three times a week starting on Day 14.

TABLE 7

Group Designation and Dose Levels in Therapeutic Study

| Group | # of animals | Donor PBMC and Treatment | Days of dosing | Dose (µg) | ROA |
|---|---|---|---|---|---|
| Naive | 5 F | None | N/A | N/A | N/A |
| Control mAb | 5 F | Donor 1 | Mo, W, Fr | 200 | IP |

TABLE 7-continued

Group Designation and Dose Levels in Therapeutic Study

| Group | # of animals | Donor PBMC and Treatment | Days of dosing | Dose (μg) | ROA |
|---|---|---|---|---|---|
| (Day 7) | | (12.00 × 10$^6$) and Control mAb | Day 7 to at least Day 33 | | |
| K44VHa-N56Q (MEDI7169) (Day 7) | 5 F | Donor 1 (12.00 × 10$^6$) and K44VHa-N56Q (MEDI7169) | Mo, W, Fr Day 7 to at least Day 33 | 200 | IP |
| K44VHa-N56Q (MEDI7169) (Day 14) | 5 F | Donor 1 (12.00 × 10$^6$) and K44VHa-N56Q (MEDI7169) | Mo, W, Fr Day 7 to at least Day 33 | 200 | IP |

F = female;
Fr = Friday;
IP = intraperitoneal;
mAb = monoclonal antibody;
Mo = Monday;
N/A = not applicable, as animals were not dosed;
PBMC = peripheral blood mononuclear cells;
PBS = phosphate- buffered saline;
ROA = route of administration;
W = Wednesday Assessment of GVHD, T-cell number and phenotype, and human cytokines in serum were performed as described above in Example 4.

Automated Assessment of Complete Blood Counts

An Sysmex XT-2000iv automated hematology analyzer (Sysmex America, Mundelein, Ill.) was utilized to assess total white blood cell numbers, as well as red blood cell numbers, hematocrit and hemoglobin values. On Days 7, 14, and 21, mice were bled from the retro-orbital sinus into heparin microtainer tubes. A 1:10 dilution was made (20 μL of each whole blood sample were diluted in 180 μL PBS), the samples were then entered into the analyzer and the resulting data was multiplied by a dilution factor of ten.

Therapeutic Treatment with K44VHa-N56O (MEDI7169) Protects Mice from GVHD

To determine whether K44VHa-N56Q (MEDI7169) given therapeutically had the ability to protect the mice from GVHD, human PBMC's were injected as described above, and K44VHa-N56Q (MEDI7169) was given either after 7 or 14 days following injection of human cells. As shown in FIG. 13, mice that received Control mAb started to die within two weeks after receiving human cells, and all died by Day 26. Mice that received K44VHa-N56Q (MEDI7169) on Day 7 were completely protected from GVHD-induced death. Mice that received K44VHa-N56Q (MEDI7169) on Day 14 (after the control mice started to die) were partially protected; 2 of the 5 mice in the Day 14 group survived past Day 26, when all the control mice had died. Mice that received human cells and Control mAb on Day 7 developed severe GVHD-induced anemia. Mice that received K44VHa-N56Q (MEDI7169) starting on Day 7 were able to maintain higher normal red blood cells, hematocrit, and hemoglobin values, which were closer to those of the naive animals that received no cells (FIG. 14).

These data show that an anti-IL-21 antibody, namely, K44VHa-N56Q, protected mice from GVHD by reducing or eliminating symptoms associated with the disease.

\* \* \*

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. An antibody or an antigen binding fragment thereof comprising a heavy chain variable region (VH) and a light chain variable region (VL), wherein
   (a) CDR1, CDR2, and CDR3 of the VH comprise the amino acid sequences of DYWMH (SEQ ID NO: 7), TIDPSDQYTIYSQNFKG (SEQ ID NO: 66), and YGFAMDY (SEQ ID NO: 9), respectively; and
   (b) CDR1, CDR2, and CDR3 of the VL comprise the amino acid sequences of RASQDISNFLN (SEQ ID NO: 12), YTSRLHS (SEQ ID NO: 13), and QQGHTLPRT (SEQ ID NO: 14) respectively;
   wherein the antibody or the antigen binding fragment thereof specifically binds to IL-21.

2. The antibody of claim 1, wherein the antibody is a murine antibody, a humanized antibody, a chimeric antibody, or a recombinant antibody.

3. The antigen binding fragment of claim 1, wherein the antigen binding fragment is Fv, Fab, F(ab')2, Fab', dsFv, scFv, and sc(Fv)2.

4. The antibody or antigen binding fragment of claim 1, wherein
   (a) the VH comprises the amino acid sequence of SEQ ID NO: 19; and
   (b) the VL comprises the amino acid sequence of SEQ ID NO: 21.

5. A pharmaceutical composition comprising the antibody or antigen-binding fragment of claim 4, and one or more of a pharmaceutically acceptable carrier, or a diluent.

6. The antibody or antigen binding fragment of claim 1, wherein the antibody or antigen binding fragment comprises an IgG constant domain.

7. The antibody or antigen binding fragment of claim 6, wherein the IgG constant domain is human IgG1.

8. The antibody or antigen binding fragment of claim 6, wherein the IgG constant domain comprises one or more amino acid substitutions that increase the antibody or antigen binding fragment half-life compared to that observed in the antibody or antigen binding fragment having a wild-type IgG constant domain.

9. The antibody or antigen binding fragment of claim 1, comprising a heavy chain amino acid sequence comprising SEQ ID NO: 16, SEQ ID NO: 20, or SEQ ID NO: 24.

10. The antibody or antigen binding fragment of claim 1, comprising a light chain amino acid sequence comprising SEQ ID NO: 18, SEQ ID NO: 22, or SEQ ID NO: 26.

11. The antibody or antigen binding fragment of claim 1, comprising (a) a heavy chain amino acid sequence comprising SEQ ID NO: 20; and (b) a light chain amino acid sequence comprising SEQ ID NO: 22.

12. The antibody or antigen binding fragment of claim 1, wherein the antibody or antigen binding fragment is conjugated to an agent selected from the group consisting of an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), and any combination thereof.

13. A method of treating an autoimmune disease or disorder in a subject in need thereof, comprising administering to the subject an effective amount of the antibody or antigen-binding fragment of claim 1, wherein the autoimmune disease is Sjögren's syndrome (SS), ANCA-associated vasculitis (AAV), giant cell arteritis (GCA) vasculitis, systemic lupus erythematosus, lupus nephritis, rheumatoid arthritis (RA), Crohn's disease, myasthenia gravis, Pemphigus vulgaris, Idiopathic thrombocytopenic purpura (ITP), Type I Diabetes, IgG4-related disease, or any combination thereof.

14. The method of claim 13, wherein the autoimmune disease is systemic lupus erythematosus.

15. A method of treating Graft-versus-host disease in a subject in need thereof, comprising administering to the subject an effective amount of the antibody or antigen-binding fragment of claim 1.

16. A method of preventing Graft-versus-host disease in a subject in need thereof, comprising administering to the subject an effective amount of the antibody or antigen-binding fragment of claim 1.

17. A method for detecting IL-21 expression levels in a sample comprising (a) contacting said sample with the antibody or antigen-binding fragment of claim 1; and (b) detecting binding of the antibody to IL-21 in said sample.

* * * * *